· US012303510B2

United States Patent
Shiota et al.

(10) Patent No.: US 12,303,510 B2
(45) Date of Patent: *May 20, 2025

(54) INHIBITORY EFFECT OF LOW MOLECULAR WEIGHT COMPOUND ON CANCER AND FIBROSIS

(71) Applicants: National University Corporation Tottori University, Tottori (JP); KanonCure, Inc., Yonago (JP)

(72) Inventors: Goshi Shiota, Yonago (JP); Noriko Itaba, Yonago (JP); Keita Kanki, Yonago (JP); Kenzo Seto, Yonago (JP); Hiroki Shimizu, Yonago (JP); Yohei Kouno, Yonago (JP); Shinya Kunita, Yonago (JP); Zyunya Adumi, Yonago (JP); Tomohiko Sakabe, Yonago (JP); Kenichiro Abe, Yonago (JP); Minoru Morimoto, Tottori (JP); Hiroyuki Oka, Tottori (JP)

(73) Assignees: National University Corporation Tottori University, Tottori (JP); KanonCure, Inc., Yonago (JP)

( * ) Notice: Subject to any disclaimer, the term of this patent is extended or adjusted under 35 U.S.C. 154(b) by 897 days.

This patent is subject to a terminal disclaimer.

(21) Appl. No.: 17/459,117

(22) Filed: Aug. 27, 2021

(65) Prior Publication Data

US 2021/0386747 A1    Dec. 16, 2021

Related U.S. Application Data

(62) Division of application No. 15/128,608, filed as application No. PCT/JP2015/059257 on Mar. 25, 2015, now Pat. No. 11,213,527.

(30) Foreign Application Priority Data

Mar. 28, 2014 (JP) ................................ 2014-070245

(51) Int. Cl.
    *A61K 31/519* (2006.01)
    *A61K 31/09* (2006.01)
    *A61K 31/16* (2006.01)
    *A61K 31/166* (2006.01)

(52) U.S. Cl.
    CPC ............ *A61K 31/519* (2013.01); *A61K 31/09* (2013.01); *A61K 31/16* (2013.01); *A61K 31/166* (2013.01)

(58) Field of Classification Search
    None
    See application file for complete search history.

(56) References Cited

U.S. PATENT DOCUMENTS

| 2003/0013743 A1 | 1/2003 | Cai et al. |
| 2004/0186078 A1 | 9/2004 | Cai et al. |
| 2004/0204477 A1 | 10/2004 | Moll et al. |
| 2007/0129353 A1 | 6/2007 | Kahn |
| 2008/0153743 A1 | 6/2008 | Henderson et al. |
| 2008/0171745 A1 | 7/2008 | Henderson et al. |
| 2009/0215781 A1 | 8/2009 | Kahn et al. |
| 2010/0069333 A1 | 3/2010 | Kahn |
| 2012/0059010 A1 | 3/2012 | Kahn et al. |
| 2013/0288248 A1 | 10/2013 | Yamazaki et al. |
| 2014/0112892 A1* | 4/2014 | Shiota ............. A61P 1/16 564/150 |
| 2018/0028536 A1 | 2/2018 | Shiota et al. |

FOREIGN PATENT DOCUMENTS

| EP | 2698365 A1 | 2/2014 |
| JP | 2004-534097 A | 11/2004 |
| JP | 2008-533155 A | 8/2008 |
| JP | 2009-515890 A | 4/2009 |
| JP | 2011-219435 A | 11/2011 |
| JP | 2012-031076 A | 2/2012 |
| WO | WO-02/089745 A2 | 11/2002 |
| WO | WO-2006/101858 A1 | 9/2006 |
| WO | WO-2007/139346 A1 | 12/2007 |
| WO | WO-2012/046797 A1 | 4/2012 |
| WO | WO-2012141038 A1 * | 10/2012 ........... A61K 35/407 |

OTHER PUBLICATIONS

Lachenmayer et al. "Wnt-Pathway Activation in Two Molecular Classes of Hepatocellular Carcinoma and Experimental Modulation by Sorafenib," Clin Cancer Res; 18(18); 4997-5007, 2012 (Year: 2012).*
Casas-Selves et al., "Tankyrase and the canonical Wnt pathway protect lung cancer cells from EGFR inhibition," Cancer Res. 72(16):4154-4164 (2012).
Cheng et al., "Wnt antagonism inhibits hepatic stellate cell activation and liver fibrosis," Am. J. Physiol. Gastrointest. Liver Physiol. 294(1):G39-G49 (2008).
Emami et al., "A small molecule inhibitor of beta-catenin/CREB-binding protein transcription," Proc. Natl. Acad. Sci. U.S.A. 101(34):12682-12687 (2004).
Guo et al., "Wnt/beta-catenin signaling: a promising new target for fibrosis diseases," Physiol. Res. 61(4):337-346 (2012).
International Search Report for International Application No. PCT/JP2015/059257, Shiota et al., "Inhibitory Effect of Low Molecular Weight Compound on Cancer and Fibrosis," mailed Jun. 23, 2015 (6 pages).

(Continued)

*Primary Examiner* — Jeffrey S Lundgren
*Assistant Examiner* — Michael J Schmitt
(74) *Attorney, Agent, or Firm* — Clark & Elbing LLP

(57) ABSTRACT

A novel therapeutic drug for malignant tumors, cancer stem cells, or fibrosis is obtained. A therapeutic drug for malignant tumors or cancer stem cells is used that includes at least one compound selected from the group consisting of compounds represented by formulas (1), (2), and (5), a salt thereof, or a solvate thereof. Alternatively, a therapeutic drug for fibrosis can be used that includes at least one compound selected from the group consisting of compounds represented by formulas (1), (2), and (5), a salt thereof, or a solvate thereof.

6 Claims, 44 Drawing Sheets

(56) References Cited

OTHER PUBLICATIONS

Noble et al., "Pirfenidone in Patients With Idiopathic Pulmonary Fibrosis (CAPACITY): Two Randomised Trials," Lancet. 377(9779):1760-1769 (2011).
Office Action dated Oct. 23, 2018 for Japanese Patent Application No. 2016-510450, Shiota et al., "Inhibitory effect of low molecular weight compound on cancer and fibrosis," filed Mar. 25, 2015 (12 pages).
Office Action dated Oct. 25, 2018 for Chinese Patent Application No. 201580017338.0, Shiota et al., "Inhibitory effect of low molecular weight compound on cancer and fibrosis," filed Mar. 25, 2015 (16 pages).
Partial Supplementary European Search Report dated Jan. 18, 2018 for European Patent Application No. 15769676.6, Shiota et al., "Inhibitory effect of low molecular weight compound on cancer and fibrosis," filed Mar. 25, 2015 (10 pages).
Patani et al., "Bioisosterism: A Rational Approach in Drug Design," Chem. Rev. 96(8):3147-3176 (1996).
Sakabe et al., Acta Hepatologica Japonica 53(Supplemental 1): A226, WS-54 (2012) (1 page).
Seto et al., Acta Hepatologica Japonica 54(Supplement 1): P-12 (2013) (3 pages).
Takahashi-Yanaga et al., "Targeting Wnt signaling: can we safely eradicate cancer stem cells?" Clin. Cancer Res. 16(12):3153-3162 (2010).
Takeishi et al., "Ablation of Fbxw7 eliminates leukemia-initiating cells by preventing quiescence," Cancer Cell 23(3):347-361 (2013).
Trosset et al., "Inhibition of protein-protein interactions: the discovery of druglike beta-catenin inhibitors by combining virtual and biophysical screening," Proteins 64(1):60-67 (2006).

\* cited by examiner

Fig. 20
HCT 116 48h luciferase assay
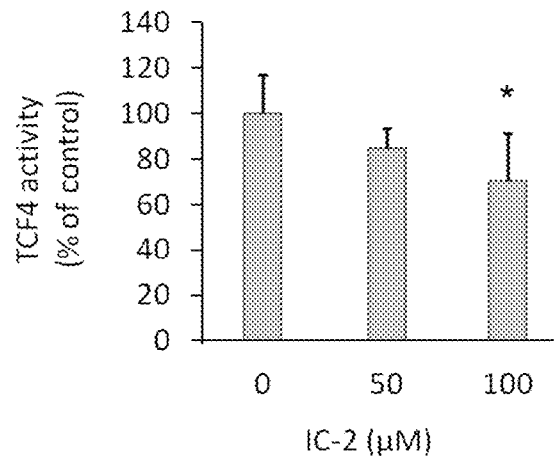
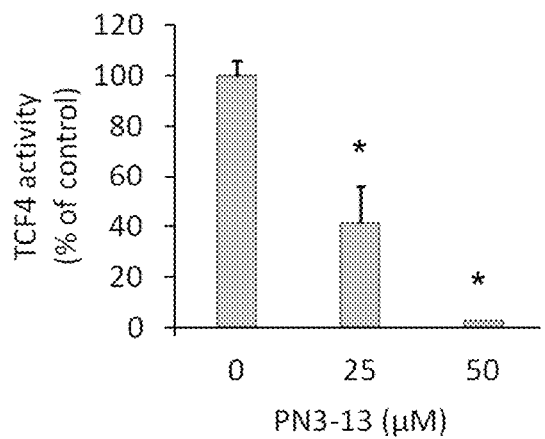
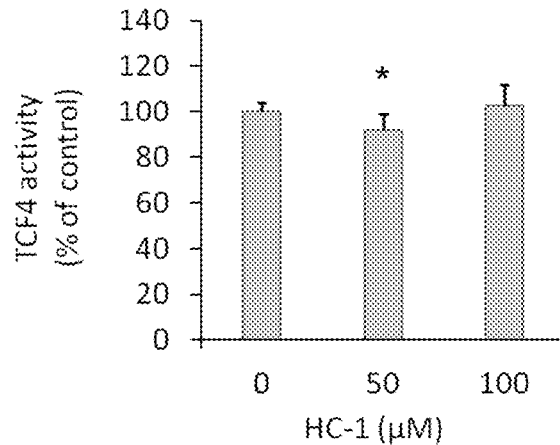

Fig. 21
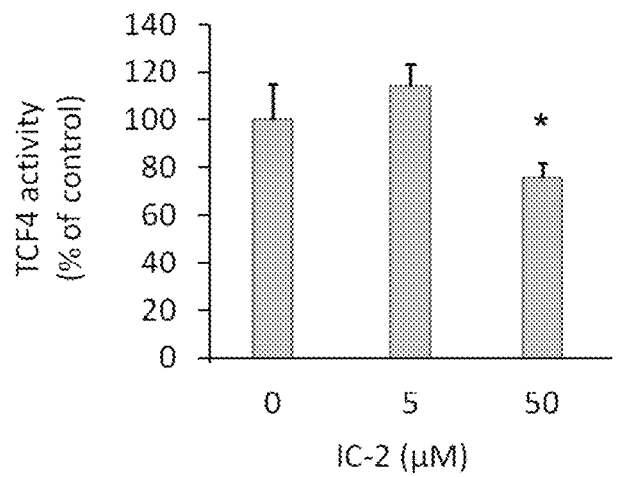
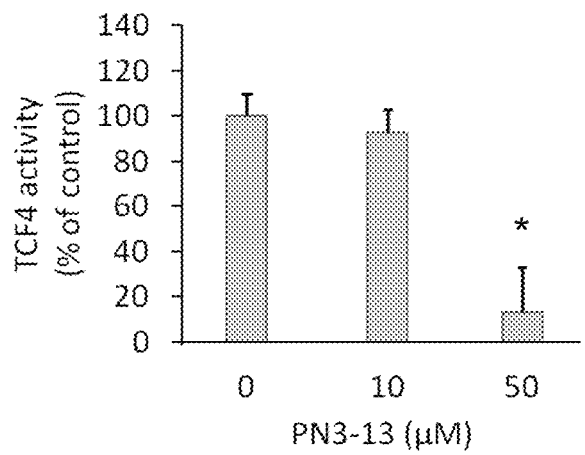
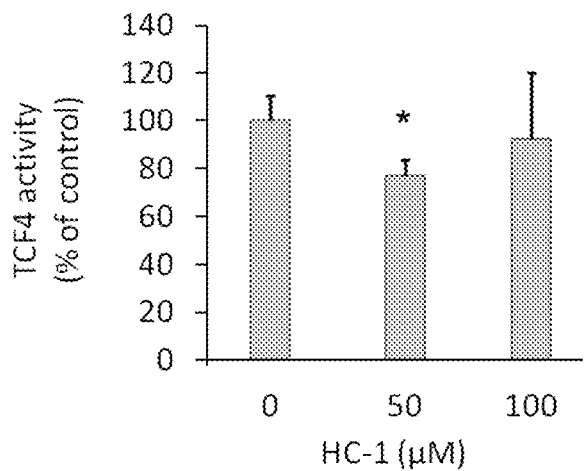

Fig. 36

| Compound | NMR and MS data |
|---|---|
| IC-2-OMe, MW: 562.67 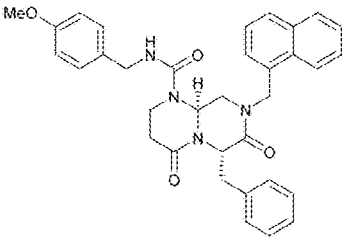 | $^1$H-NMR (600 MHz, CDCl$_3$) $\delta$ = 2.24–2.32 (m, 1H), 2.34–2.43 (m, 1H), 2.92–3.01 (m, 2H), 3.13 (t, $J$ = 11.2 Hz, 1H), 3.31 (dd, $J$ = 13.6, 5.6 Hz, 1H), 3.54 (dd, $J$ = 13.7, 5.4 Hz, 1H), 3.82 (s, 3H), 3.88 (dd, $J$ = 14.0, 5.7 Hz, 1H), 3.97 (br t, 1H), 4.07 (dd, $J$ = 14.2, 4.8 Hz, 1H), 4.15 (dd, $J$ = 14.3, 5.7 Hz, 1H), 4.67 (d, $J$ = 10.4 Hz, 1H), 5.05 (d, $J$ = 14.7 Hz, 1H), 5.15 (d, $J$ = 14.6 Hz, 1H), 5.43 (t, $J$ = 5.5 Hz, 1H), 6.83 (d, $J$ = 8.7 Hz, 2H), 6.96 (t, $J$ = 7.4 Hz, 1H), 6.98 (d, $J$ = 8.7 Hz, 2H), 7.08 (t, $J$ = 7.7 Hz, 2H), 7.21 (d, $J$ = 7.7 Hz, 2H), 7.25 (d, $J$ = 7.3 Hz, 1H), 7.38 (t, $J$ = 8.2 Hz, 1H), 7.55 (t, $J$ = 7.4 Hz, 1H), 7.59 (t, $J$ = 7.6 Hz, 1H), 7.84 (d, $J$ = 8.2 Hz, 1H), 7.90 (d, $J$ = 8.0 Hz, 1H), 8.11 (d, $J$ = 8.3 Hz, 1H). ESI-HRMS $m/z$ calcd for C$_{34}$H$_{34}$N$_4$NaO$_4$ [M+Na]$^+$ 585.248, found 585.246. |
| IC-2-F, MW: 550.63 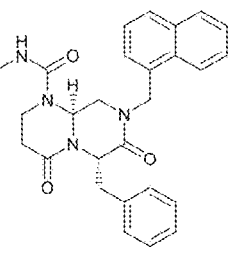 | $^1$H-NMR (600 MHz, CDCl$_3$) $\delta$ = 2.26–2.39 (m, 1H), 2.35–2.45 (m, 1H), 2.93 (dd, $J$ = 11.8, 3.6 Hz, 1H), 2.98 (td, $J$ = 13.2, 3.5 Hz, 1H), 3.14 (t, $J$ = 11.2 Hz, 1H), 3.31 (dd, $J$ = 13.7, 5.6 Hz, 1H), 3.56 (dd, $J$ = 13.7, 5.2 Hz, 1H), 3.91 (dd, $J$ = 14.0, 5.8 Hz, 1H), 3.99 (br t, 1H), 4.07 (dd, $J$ = 14.6, 5.0 Hz, 1H), 4.17 (dd, $J$ = 14.5, 5.9 Hz, 1H), 4.62 (d, $J$ = 10.3 Hz, 1H), 4.99 (d, $J$ = 14.7 Hz, 1H), 5.22 (d, $J$ = 14.7 Hz, 1H), 5.43 (t, $J$ = 5.4 Hz, 1H), 6.95–7.03 (m, 5H), 7.08 (t, $J$ = 7.6 Hz, 2H), 7.21 (d, $J$ = 7.5 Hz, 2H), 7.26 (d, $J$ = 6.6 Hz, 1H), 7.38 (t, $J$ = 7.6 Hz, 1H), 7.55 (t, $J$ = 7.4 Hz, 2H), 7.59 (t, $J$ = 7.5 Hz, 2H), 7.84 (d, $J$ = 8.3 Hz, 1H), 7.90 (d, $J$ = 8.0 Hz, 1H), 8.11 (d, $J$ = 8.2 Hz, 1H). ESI-HRMS $m/z$ calcd for C$_{33}$H$_{31}$FN$_4$NaO$_3$ [M+Na]$^+$ 573.228, found 573.226. |
| IC-2-Cl, MW: 567.09 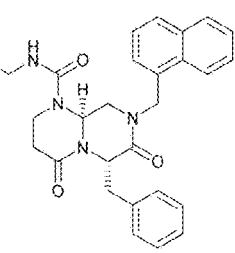 | $^1$H-NMR (600 MHz, CDCl$_3$) $\delta$ = 2.26–2.34 (m, 1H), 2.34–2.44 (m, 1H), 2.91 (dd, $J$ = 11.8, 3.7 Hz, 1H), 2.98 (td, $J$ = 13.1, 3.5 Hz, 1H), 3.15 (t, $J$ = 11.2 Hz, 1H), 3.31 (dd, $J$ = 13.7, 5.6 Hz, 1H), 3.57 (dd, $J$ = 13.6, 5.1 Hz, 1H), 3.92 (dd, $J$ = 14.0, 5.9 Hz, 1H), 3.97 (br t, 1H), 4.05 (dd, $J$ = 14.7, 5.1 Hz, 1H), 4.17 (dd, $J$ = 14.7, 5.9 Hz, 1H), 4.60 (d, $J$ = 10.3 Hz, 1H), 4.98 (d, $J$ = 14.6 Hz, 1H), 5.23 (d, $J$ = 14.6 Hz, 1H), 5.43 (t, $J$ = 5.3 Hz, 1H), 6.96 (d, $J$ = 8.4 Hz, 2H), 7.00 (t, $J$ = 7.3 Hz, 1H), 7.09 (t, $J$ = 7.6 Hz, 2H), 7.21 (d, $J$ = 7.6 Hz, 2H), 7.24–7.27 (m, 3H), 7.38 (t, $J$ = 7.6 Hz, 1H), 7.55 (t, $J$ = 7.4 Hz, 2H), 7.59 (t, $J$ = 7.5 Hz, 2H), 7.84 (d, $J$ = 8.3 Hz, 1H), 7.90 (d, $J$ = 8.0 Hz, 1H), 8.10 (d, $J$ = 8.3 Hz, 1H). ESI-HRMS $m/z$ calcd for C$_{33}$H$_{31}$ClN$_4$NaO$_3$ [M+Na]$^+$ 589.198, found 589.197. |
| IC-2-OMOM, MW: 592.70 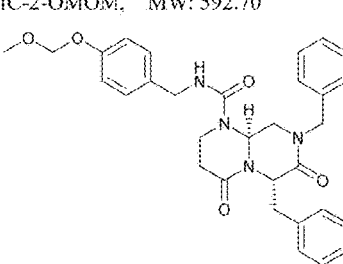 | $^1$H-NMR (600 MHz, CDCl$_3$) $\delta$ = 2.24–2.32 (m, 1H), 2.33–2.43 (m, 1H), 2.91–3.02 (m, 2H), 3.13 (t, $J$ = 11.2 Hz, 1H), 3.31 (dd, $J$ = 13.7, 5.6 Hz, 1H), 3.50 (s, 3H), 3.54 (dd, $J$ = 13.7, 5.3 Hz, 1H), 3.89 (dd, $J$ = 14.0, 5.9 Hz, 1H), 3.97 (br t, 1H), 4.06 (dd, $J$ = 14.2, 4.8 Hz, 1H), 4.16 (dd, $J$ = 14.2, 5.7 Hz, 1H), 4.66 (d, $J$ = 10.4 Hz, 1H), 5.03 (d, $J$ = 14.6 Hz, 1H), 5.17 (d, $J$ = 14.7 Hz, 1H), 5.19 (s, 2H) 5.43 (t, $J$ = 5.4 Hz, 1H), 6.92–6.99 (m, 5H), 7.07 (t, $J$ = 7.6 Hz, 2H), 7.20 (d, $J$ = 6.9 Hz, 2H), 7.26 (d, $J$ = 6.5 Hz, 1H), 7.39 (t, $J$ = 7.6 Hz, 1H), 7.55 (t, $J$ = 7.4 Hz, 1H), 7.58 (t, $J$ = 7.5 Hz, 1H), 7.85 (d, $J$ = 8.2 Hz, 1H), 7.90 (d, $J$ = 8.0 Hz, 1H), 8.11 (d, $J$ = 8.4 Hz, 1H). ESI-HRMS $m/z$ calcd for C$_{35}$H$_{37}$N$_4$O$_5$ [M+H]$^+$ 593.276, found 593.275. |
| IC-2-NO2, MW: 577.64 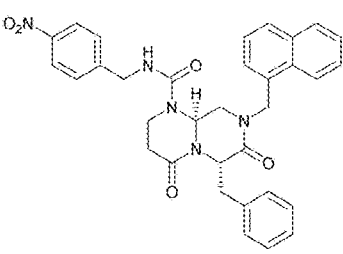 | $^1$H-NMR (600 MHz, CDCl$_3$) $\delta$ = 2.30–2.38 (m, 1H), 2.38–2.49 (m, 1H), 2.91 (dd, $J$ = 11.8, 3.7 Hz, 1H), 3.02 (td, $J$ = 13.1, 3.5 Hz, 1H), 3.19 (t, $J$ = 11.2 Hz, 1H), 3.31 (dd, $J$ = 13.7, 5.7 Hz, 1H), 3.60 (dd, $J$ = 13.7, 4.9 Hz, 1H), 3.97 (dd, $J$ = 14.0, 5.8 Hz, 1H), 4.06–4.18 (m, 2H), 4.32 (dd, $J$ = 16.9, 7.5 Hz, 1H), 4.58 (d, $J$ = 10.0 Hz, 1H), 4.91 (d, $J$ = 14.7 Hz, 1H), 5.33 (d, $J$ = 14.7 Hz, 1H), 5.45 (t, $J$ = 5.3 Hz, 1H), 7.05 (t, $J$ = 7.4 Hz, 1H), 7.09–7.15 (m, 4H), 7.24 (d, $J$ = 7.5 Hz, 2H), 7.28 (d, $J$ = 7.0 Hz, 1H), 7.40 (t, $J$ = 7.6 Hz, 1H), 7.55 (t, $J$ = 7.5 Hz, 1H), 7.59 (t, $J$ = 7.6 Hz, 1H), 7.85 (d, $J$ = 8.3 Hz, 1H), 7.89 (d, $J$ = 8.0 Hz, 1H), 8.08–8.14 (m, 3H). ESI-HRMS $m/z$ calcd for C$_{33}$H$_{31}$N$_5$NaO$_5$ [M+Na]$^+$ 600.222, found 600.221. |

Fig. 37

| IC-2-OPMB, MW: 668.79 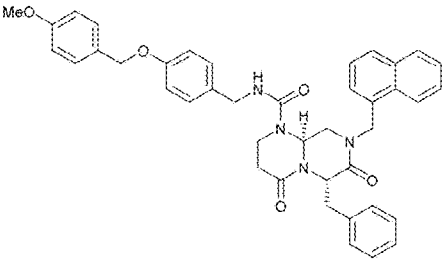 | $^1$H-NMR (600 MHz, CDCl$_3$) $\delta$ = 2.24–2.31 (m, 1H), 2.32–2.43 (m, 1H), 2.90–3.01 (m, 2H), 3.12 (t, $J$= 11.2 Hz, 1H), 3.31 (dd, $J$= 13.7, 5.6 Hz, 1H), 3.53 (dd, $J$= 13.6, 5.4 Hz, 1H), 3.80 (s, 3H), 3.87 (dd, $J$= 14.0, 5.8 Hz, 1H), 3.98 (br t, 1H), 4.07 (dd, $J$= 14.2, 4.9 Hz, 1H), 4.14 (dd, $J$= 14.2, 5.7 Hz, 1H), 4.67 (d, $J$= 10.4 Hz, 1H), 5.00 (s, 2H), 5.04 (d, $J$= 14.7 Hz, 1H), 5.15 (d, $J$= 14.7 Hz, 1H), 5.42 (t, $J$= 5.4 Hz, 1H), 6.87–6.96 (m, 5H), 6.97 (d, $J$= 8.6 Hz, 2H), 7.06 (t, $J$= 7.6 Hz, 2H), 7.20 (d, $J$= 7.7 Hz, 2H), 7.24 (d, $J$= 7.0 Hz, 1H), 7.34–7.40 (m, 3H), 7.54 (t, $J$= 7.4 Hz, 1H), 7.57 (t, $J$= 7.6 Hz, 1H), 7.83 (d, $J$= 8.2 Hz, 1H), 7.88 (d, $J$= 8.0 Hz, 1H), 8.10 (d, $J$= 8.3 Hz, 1H). ESI-HRMS $m/z$ calcd for C$_{41}$H$_{40}$N$_4$NaO$_5$ [M+Na]$^+$ 691.290, found 691.289. |
| --- | --- |
| IC-2-MOTBS, MW: 676.93 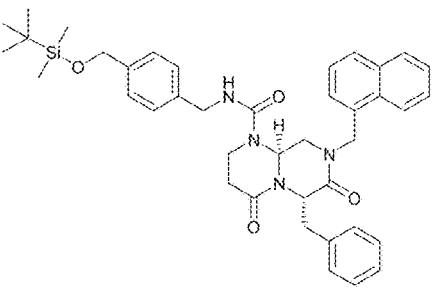 | $^1$H-NMR (600 MHz, CDCl$_3$) $\delta$ = 0.12 (s, 6H), 0.96 (s, 9H), 2.23–2.32 (m, 1H), 2.33–2.45 (m, 1H), 2.91–3.04 (m, 2H), 3.13 (t, $J$ = 11.2 Hz, 1H), 3.31 (dd, $J$ = 13.6, 5.5 Hz, 1H), 3.54 (dd, $J$ = 13.7, 5.4 Hz, 1H), 3.88 (dd, $J$ = 13.9, 5.7 Hz, 1H), 4.01 (br t, 1H), 4.12 (dd, $J$ = 14.4, 4.9 Hz, 1H), 4.21 (dd, $J$ = 14.4, 5.7 Hz, 1H), 4.70 (d, $J$ = 10.4 Hz, 1H), 4.75 (s, 2H), 5.08 (d, $J$ = 14.6 Hz, 1H), 5.14 (d, $J$ = 14.7 Hz, 1H), 5.43 (t, $J$ = 5.4 Hz, 1H), 6.96 (t, $J$ = 7.4 Hz, 1H), 7.03 (d, $J$ = 8.0 Hz, 2H), 7.08 (t, $J$ = 7.7 Hz, 2H), 7.21 (d, $J$ = 7.5 Hz, 2H), 7.23–7.30 (m, 3H), 7.38 (t, $J$ = 7.6 Hz, 1H), 7.54 (t, $J$ = 7.4 Hz, 1H), 7.58 (t, $J$ = 7.6 Hz, 1H), 7.84 (d, $J$ = 8.2 Hz, 1H), 7.89 (d, $J$ = 8.0 Hz, 1H), 8.10 (d, $J$ = 8.3 Hz, 1H). ESI-HRMS $m/z$ calcd for C$_{40}$H$_{48}$N$_4$NaO$_4$Si [M+Na]$^+$ 699.334, found 699.333. |
| IC-2-OH, MW: 548.64 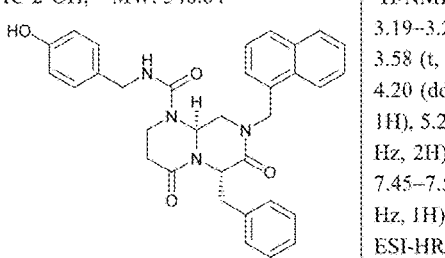 | $^1$H-NMR (600 MHz, DMSO-$d_6$) $\delta$ = 2.00–2.07 (m, 2H), 3.09–3.18 (m, 2H), 3.19–3.29 (m, 2H), 3.58 (t, $J$ = 11.2 Hz, 1H), 3.84 (d, $J$ = 13.7, 1H), 4.07 (dd, $J$ = 14.9, 5.4 Hz, 1H), 4.20 (dd, $J$ = 14.9, 5.9 Hz, 1H), 4.92 (d, $J$ = 15.0 Hz, 1H), 5.15 (d, $J$ = 15.0 Hz, 1H), 5.22 (dd, $J$ = 9.3, 4.7 Hz, 1H), 5.78 (dd, $J$ = 10.7, 4.1 Hz, 1H), 6.70 (d, $J$= 8.6 Hz, 2H), 7.34 (d, $J$ = 8.5 Hz, 2H), 7.11–7.20 (m, 5H), 7.41 (d, $J$ = 6.9 Hz, 1H), 7.45–7.53 (m, 2H), 7.54–7.62 (m, 2H), 7.91 (d, $J$ = 8.3 Hz, 1H), 7.98 (d, $J$ = 7.9 Hz, 1H), 8.16 (d, $J$ = 8.1 Hz, 1H), 9.31 (s, 1H). ESI-HRMS $m/z$ calcd for C$_{33}$H$_{32}$N$_4$NaO$_4$ [M+Na]$^+$ 571.232, found 571.231. |
| IC-2-MOH, MW: 562.67 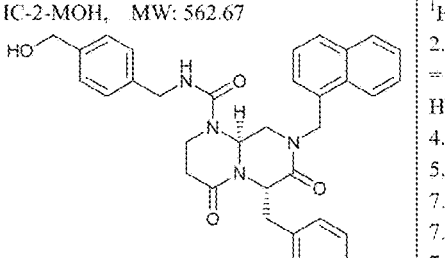 | $^1$H-NMR (600 MHz, CDCl$_3$) $\delta$ = 2.08 (br s, 1H), 2.17–2.24 (m, 1H), 2.24–2.34 (m, 1H), 2.89–3.01 (m, 2H), 3.11 (t, $J$ = 11.2 Hz, 1H), 3.30 (dd, $J$ = 13.7, 5.4 Hz, 1H), 3.48 (dd, $J$ = 13.7, 5.7 Hz, 1H), 3.82 (dd, $J$ = 14.0, 5.7 Hz, 1H), 4.12 (dd, $J$ = 14.5, 5.1 Hz, 1H), 4.23 (dd, $J$ = 14.5, 5.7 Hz, 1H), 4.30 (br t, 1H), 4.68 (s, 2H), 4.81 (d, $J$ = 10.2 Hz, 1H), 5.04–5.13 (m, 2H), 5.39 (t, $J$ = 5.7 Hz, 1H), 7.01 (t, $J$ = 7.4 Hz, 1H), 7.06 (d, $J$= 8.1 Hz, 2H), 7.10 (t, $J$ = 7.6 Hz, 2H), 7.20 (d, $J$ = 7.5 Hz, 2H), 7.25 (d, $J$ = 7.1 Hz, 1H), 7.29 (d, $J$ = 8.0 Hz, 2H), 7.38 (t, $J$ = 7.6 Hz, 1H), 7.53 (t, $J$ = 7.4 Hz, 1H), 7.57 (t, $J$ = 7.5 Hz, 1H), 7.83 (d, $J$ = 8.2 Hz, 1H), 7.88 (d, $J$ = 8.0 Hz, 1H), 8.08 (d, $J$ = 8.3 Hz, 1H). ESI-HRMS $m/z$ calcd for C$_{34}$H$_{34}$N$_4$NaO$_4$ [M+Na]$^+$ 585.248, found 585.247. |

- Cell density: $2.0 \times 10^4$ cells/cm$^2$
- Cell seeding: 1% FBS DMEM
- TGF-$\beta$ concentration: 2.5 ng/ml
- Examined HSCs activation marker: $\alpha$-SMA, COL1A1, TGF-$\beta$
- Compound・TGF-$\beta$ application: at the same time・every 24 h
- Analysis was performed using a 384-well plate

INHIBITORY EFFECT OF LOW MOLECULAR WEIGHT COMPOUND ON CANCER AND FIBROSIS

TECHNICAL FIELD

The present invention relates to therapeutic drugs for malignant tumors or fibrosis.

BACKGROUND ART

Examples of the leading causes of human death include malignant tumors, heart disease, and cerebrovascular disease. Among them, the mechanism of causing malignant tumors is complicated, so that the malignant tumors, in particular, can be said to be a hard-to-prevent and hard-to-treat disease.

Recently, the presence of a cancer stem cell has been elucidated in the research field of such malignant tumors. This cancer stem cell has received attention in order to establish a new therapeutic strategy. The cancer stem cell is considered to differentiate into cancer cells. In some patients, cancer may relapse after cancer cells have been removed and a certain period has then passed. This seems to be due to a very small number of surviving cancer stem cells.

This cancer stem cell is characterized in that many conventional anti-cancer drugs are ineffective. With regard to this point, Prof. Nakayama of Kyushu Univ. has reported research results in which when Fbxw7-deficient model mice were treated with imatinib (anti-cancer drug), cancer stem cells were killed (Non-Patent Literature 1). In this connection, however, no compound has been obtained that directly inhibits proliferation of cancer stem cells.

Meanwhile, examples of a symptom that causes malignant tumors include tissue fibrosis. For instance, when liver fibrosis advances, this causes hepatic cirrhosis, leading to liver cancer. In addition, fibrosis occurs in the lung, kidney, heart, skin, etc. Non-Patent Literature 2 describes the outcome of a clinical trial on pirfenidone involved with fibrosis treatment.

Here, the present inventors have reported low-molecular-weight compounds in three publications (Non-Patent Literatures 3 and 4 and Patent Literature 1). Non-Patent Literatures 3 and 4 describe low-molecular-weight compounds that exert an inhibitory effect on proliferation of liver cancer cells and an inhibitory effect on a Wnt/β-catenin signal. In addition, it is described that the low-molecular-weight compound disclosed in Non-Patent Literature 4 increased expression of CD44. However, neither Non-Patent Literature 3 nor 4 describes what kinds of the structure and function of a compound cause the compound to exert a growth inhibitory effect on liver cancer cells.

Patent Literature 1 describes that PN-1-2, PN-3-4, PN-3-13, HC-1, and IC-2 inhibit a Wnt/β-catenin signal in a mesenchymal stem cell, thereby inducing differentiation of the mesenchymal stem cell into hepatocytes. This literature, however, discloses nothing about inhibition of proliferation of cancer cells or cancer stem cells.

CITATION LIST

Patent Literature

[Patent Literature 1] WO2012/141038

Non-Patent Literature

[Non-Patent Literature 1] Takeishi et al., Cancer Cell, 2013 March 18; 23 (3): 347-61.

[Non-Patent Literature 2] Noble et al., Lancet, 2011 May 21; 377 (9779): 1760-9.

[Non-Patent Literature 3] Sakabe et al., "Kanzo (Liver)", vol. 53, Supplement 1, 2012, A226, WS-54.

[Non-Patent Literature 4] Seto et al., "Kanzo (Liver)", vol. 54, Supplement 1, 2013, P-12.

SUMMARY OF INVENTION

Technical Problem

As described above, the treatment strategy against malignant tumors advance gradually. Nevertheless, the malignant tumors are one of the current leading causes of human death. Hence, conventional treatment strategies are simply insufficient.

In the field of treatment of malignant tumors, it is known that the pharmacological effect of a low-molecular-weight compound administered largely varies depending on characteristics of the structure of the individual compound. Also, this field involves considerable uncertainty. Whether or not a desirable pharmacological effect can be achieved is difficult to predict during development of a novel treatment protocol. Because of this, it has been uneasy to identify a novel low-molecular-weight compound that exerts an effect of treating malignant tumors.

Further, it is uneasy to identify a novel low-molecular-weight compound that inhibits proliferation of not only malignant tumor cells, but also cancer stem cells.

Furthermore, as described above, there is an increasing number of reports on research regarding fibrosis treatment. However, there are only a few therapeutic drugs effective in treating fibrosis. Besides, an adverse effect may cause a problem to some patients. Hence, conventional anti-fibrosis agents are simply insufficient.

The present invention has been made in view of the above situations. The purpose of the present invention is to provide a novel therapeutic drug for malignant tumors, cancer stem cells, or fibrosis.

Solution to Problem

The present inventors have conducted intensive research. As a result, the present inventors have successfully identified low-molecular-weight compounds that exert an anti-malignant tumor effect as described in Examples below. Further, these low-molecular weight compounds have been found to exert an inhibitory effect on proliferation of not only tumor cells, but also cancer stem cells. Cancer stem cells are known to cause relapse and metastasis of malignant tumors. The above low-molecular-weight compounds that can inhibit proliferation of cancer stem cells can thus be said to be very promising compounds as an active ingredient in a therapeutic drug for malignant tumors. Besides, the above compounds have also been found to exert an inhibitory effect on fibrosis. Then, the present inventors have completed the present invention on the basis of these findings.

Specifically, an aspect of the present invention provides a therapeutic drug for a malignant tumor, which drug includes at least one compound selected from the group consisting of compounds represented by formulas (1), (2), and (5), a salt thereof, or a solvate thereof.

[Chemical Formula 1]

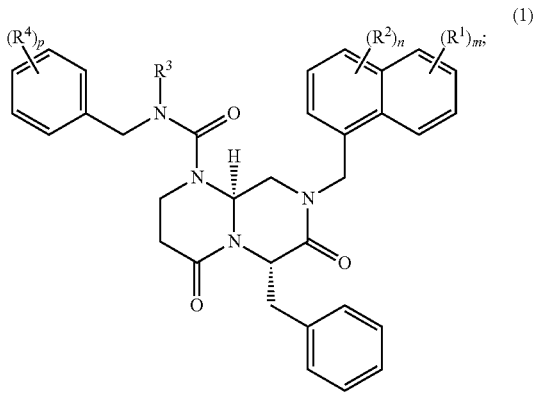

[Chemical Formula 2]

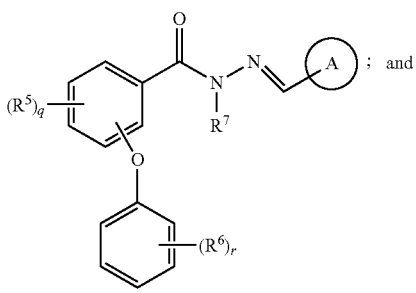

[Chemical Formula 5]

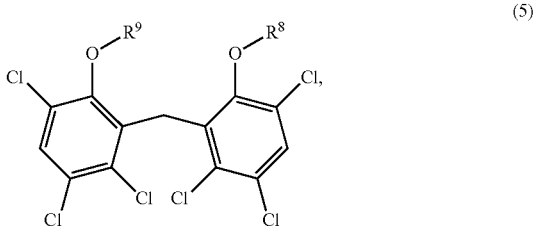

wherein $R^1$, $R^2$, $R^4$, $R^5$, and $R^6$ are the same or different and each represent H, halogen, nitro, cyano, OH, optionally substituted $C_{1-6}$ alkyl, optionally substituted $C_{2-6}$ alkenyl, optionally substituted $C_{1-6}$ alkoxy, aryl, or heteroaryl;

$R^3$ and $R^7$ are the same or different and each represent H, optionally substituted $C_{1-6}$ alkyl, or optionally substituted $C_{2-6}$ alkenyl;

ring A is optionally substituted aryl or optionally substituted heteroaryl;

$R^8$ and $R^9$ are the same or different and each represent optionally substituted $C_{1-6}$ alkyl or optionally substituted $C_{2-6}$ alkenyl;

m and q are the same or different and each represent an integer of any of 1 to 4;

n is an integer of any of 1 to 3; and p and r are the same or different and each represent an integer of any of 1 to 5.

In addition, another aspect of the present invention provides a therapeutic drug for a cancer stem cell, which drug includes at least one compound selected from the group consisting of compounds represented by the above formulas (1), (2), and (5), a salt thereof, or a solvate thereof, wherein $R^1$, $R^2$, $R^4$, $R^5$, and $R^6$ are the same or different and each represent H, halogen, nitro, cyano, OH, optionally substituted $C_{1-6}$ alkyl, optionally substituted $C_{2-6}$ alkenyl, optionally substituted $C_{1-6}$ alkoxy, aryl, or heteroaryl;

$R^3$ and $R^7$ are the same or different and each represent H, optionally substituted $C_{1-6}$ alkyl, or optionally substituted $C_{2-6}$ alkenyl;

ring A is optionally substituted aryl or optionally substituted heteroaryl;

$R^8$ and $R^9$ are the same or different and each represent optionally substituted $C_{1-6}$ alkyl or optionally substituted $C_{2-6}$ alkenyl;

m and q are the same or different and each represent an integer of any of 1 to 4;

n is an integer of any of 1 to 3; and p and r are the same or different and each represent an integer of any of 1 to 5.

Further, another aspect of the present invention provides a therapeutic drug for fibrosis, which drug includes at least one compound selected from the group consisting of compounds represented by the above formulas (1), (2), and (5), a salt thereof, or a solvate thereof, wherein $R^1$, $R^2$, $R^4$, $R^5$, and $R^6$ are the same or different and each represent H, halogen, nitro, cyano, OH, optionally substituted $C_{1-6}$ alkyl, optionally substituted $C_{2-6}$ alkenyl, optionally substituted $C_{1-6}$ alkoxy, aryl, or heteroaryl;

$R^3$ and $R^7$ are the same or different and each represent H, optionally substituted $C_{1-6}$ alkyl, or optionally substituted $C_{2-6}$ alkenyl;

ring A is optionally substituted aryl or optionally substituted heteroaryl;

$R^8$ and $R^9$ are the same or different and each represent optionally substituted $C_{1-6}$ alkyl or optionally substituted $C_{2-6}$ alkenyl;

m and q are the same or different and each represent an integer of any of 1 to 4;

n is an integer of any of 1 to 3; and p and r are the same or different and each represent an integer of any of 1 to 5.

Furthermore, a preferable embodiment of the present invention provides the above therapeutic drug for a malignant tumor, a cancer stem cell, or fibrosis, wherein the above $R^1$, $R^2$, $R^4$, $R^5$, and $R^6$ are the same or different and each represent H, halogen, nitro, cyano, OH, $C_{1-6}$ alkyl, $C_{1-6}$ halogenoalkyl, $C_{1-6}$ hydroxyalkyl, $C_{1-6}$ alkylamino, $C_{1-6}$ alkoxy, $C_{1-6}$ halogenoalkoxy, $C_{1-6}$ hydroxyalkoxy, $C_{1-6}$ alkoxyamino, $C_{1-6}$ alkoxy-substituted $C_{1-6}$ alkoxy, $C_{1-6}$ alkoxyphenyl-substituted $C_{1-6}$ alkoxy, (trialkylsiloxy) $C_{1-6}$ alkyl, or (alkyl diphenyl siloxy) $C_{1-6}$ alkyl; the above $R^3$ and $R^7$ are H; the above ring A is naphthyl, phenyl substituted by five halogens, or furyl substituted by one methyl; and $R^8$ and $R^9$ are the same or different and each represent $C_{1-6}$ alkyl.

Advantages

According to the present invention, a novel therapeutic drug can be used to treat malignant tumors, cancer stem cells, or fibrosis.

BRIEF DESCRIPTION OF THE DRAWINGS

FIG. 20 is graphs showing the results of examining an inhibitory effect on a Wnt/β-catenin signal in colon cancer.

FIG. 21 is graphs showing the results of examining an inhibitory effect on a Wnt/β-catenin signal in colon cancer.

FIG. 36 is a table listing the structural formula and spectrum data of each of IC-2 derivatives according to Example 8.

FIG. 37 is a table listing the structural formula and spectrum data of each of IC-2 derivatives according to Example 8.

FIG. 43 is a graph showing the results of a luciferase assay performed at 24 h after liver stellate cells were treated with IC-2+Wnt3a.

FIG. 46 is a graph showing the results of a luciferase assay performed at 48 h after liver stellate cells were treated with IC-2+Wnt3a.

FIG. 50 is a graph showing the results of a luciferase assay performed at 24 h after liver stellate cells were treated with HC-1+Wnt3a.

FIG. 53 is a graph showing the results of a luciferase assay performed at 48 h after liver stellate cells were treated with HC-1+Wnt3a.

DESCRIPTION OF EMBODIMENTS

Figure 1:
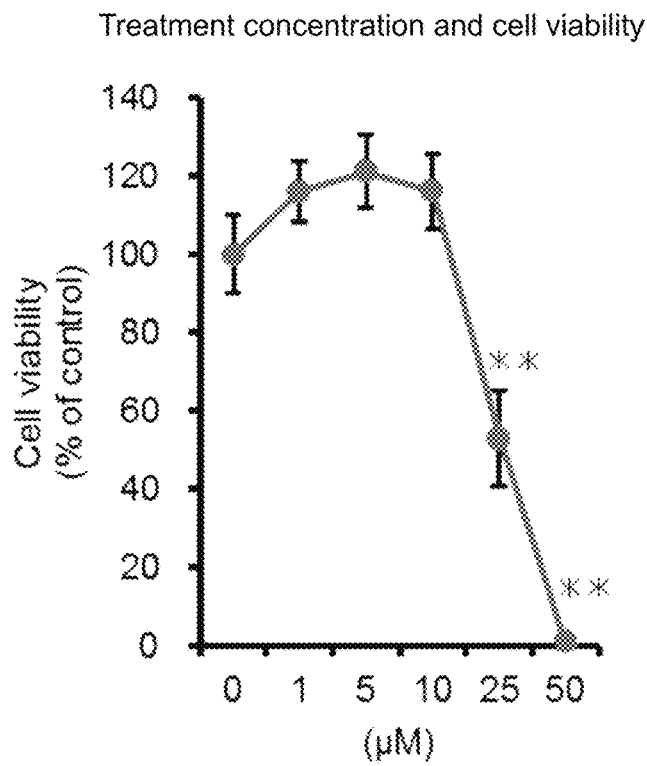
FIG. 1 is a graph showing the results of checking the (concentration-dependent) cell viability of liver cancer cells after IC-2 treatment.

Hereinafter, embodiments of the present invention will be described in detail. Note that descriptions are not repeated so as to avoid redundancy.

An embodiment of the present invention provides a therapeutic drug for a malignant tumor, which drug includes at least one compound selected from the group consisting of compounds represented by formulas (1), (2), and (5), a salt thereof, or a solvate thereof. This drug may be used to treat malignant tumors.

An embodiment of the present invention provides a therapeutic drug for a cancer stem cell, which drug includes at least one compound selected from the group consisting of compounds represented by formulas (1), (2), and (5), a salt thereof, or a solvate thereof. This drug may be used to treat cancer stem cells.

An embodiment of the present invention provides a growth-inhibiting drug for a malignant tumor cell or a cancer stem cell, which drug includes at least one compound selected from the group consisting of compounds represented by formulas (1), (2), and (5), a salt thereof, or a solvate thereof. This drug may be used to inhibit proliferation of malignant tumor cells or cancer stem cells.

An embodiment of the present invention provides a drug for inhibiting the relapse of a malignant tumor, which drug includes at least one compound selected from the group consisting of compounds represented by formulas (1), (2), and (5), a salt thereof, or a solvate thereof. This inhibitory drug may be used to inhibit the relapse of a malignant tumor.

An embodiment of the present invention provides a therapeutic drug for fibrosis, which drug includes at least one compound selected from the group consisting of compounds represented by formulas (1), (2), and (5), a salt thereof, or a solvate thereof. This drug may be used to treat fibrosis.

An embodiment of the present invention provides a drug for treating a disease accompanied by fibrosis, which drug includes at least one compound selected from the group consisting of compounds represented by the above formulas (1), (2), and (5), a salt thereof, or a solvate thereof. This drug may be used to treat a disease accompanied by fibrosis.

In the formulas (1), (2), and (5), $R^1$, $R^2$, $R^4$, $R^5$, and $R^6$ are the same or different and each represent H, halogen, nitro, cyano, OH, optionally substituted $C_{1-6}$ alkyl, optionally substituted $C_{2-6}$ alkenyl, optionally substituted $C_{1-6}$ alkoxy, aryl, or heteroaryl. In addition, $R^3$ and $R^7$ each represent H, optionally substituted $C_{1-6}$ alkyl, or optionally substituted $C_{2-6}$ alkenyl. In addition, ring A is optionally substituted aryl or optionally substituted heteroaryl. In addition, $R^8$ and $R^9$ are the same or different and each represent optionally substituted $C_{1-6}$ alkyl or optionally substituted $C_{2-6}$ alkenyl. In addition, m and q are the same or different and each represent an integer of any of 1 to 4. In addition, n is an integer of any of 1 to 3. In addition, p and r are the same or different and each represent an integer of any of 1 to 5.

Preferably, the above $R^1$, $R^2$, $R^4$, $R^5$, and $R^6$ are the same or different and may each represent H, halogen, nitro, cyano, OH, $C_{1-6}$ alkyl, $C_{1-6}$ halogenoalkyl, $C_{1-6}$ hydroxyalkyl, $C_{1-6}$ alkylamino, $C_{1-6}$ alkoxy, $C_{1-6}$ halogenoalkoxy, $C_{1-6}$ hydroxyalkoxy, or $C_{1-6}$ alkoxyamino, or $C_{1-6}$ alkoxy-substituted $C_{1-6}$ alkoxy, $C_{1-6}$ alkoxyphenyl-substituted $C_{1-6}$ alkoxy, (trialkylsiloxy) $C_{1-6}$ alkyl, or (alkyl diphenyl siloxy) $C_{1-6}$ alkyl. In addition, the above $R^3$ and $R^7$ are preferably H. In addition, the above ring A is preferably naphthyl, phenyl substituted by five halogens, or furyl substituted by one methyl. The compound represented by formula (2) in this case may be synthesized by a process disclosed in, for example, WO2012/141038. Preferably, $R^8$ and $R^9$ are the same or different and each represent $C_{1-6}$ alkyl.

As used herein, the term "halogen" means F, Cl, Br, or I.

As used herein, unless otherwise indicated, the terms "alkyl" and "alkenyl" mean a linear or branched hydrocarbon chain.

As used herein, the term "$C_{1-6}$" refers to hydrocarbon containing 1, 2, 3, 4, 5, or 6 carbon atoms. That is, the term "$C_{1-6}$ alkyl" refers to alkyl containing 1, 2, 3, 4, 5, or 6 carbon atoms. Examples of $C_{1-6}$ alkyl include methyl, ethyl, n-propyl, isopropyl, n-butyl, isobutyl, sec-butyl, tert-butyl, n-pentyl, and n-hexyl.

As used herein, examples of "alkenyl" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, and 5-hexenyl.

As used herein, examples of "alkoxy" include methoxy, ethoxy, propoxy, isopropoxy, butoxy, isobutoxy, sec-butoxy, tert-butxy, pentoxy, isopentoxy, and hexoxy.

As used herein, the term "optionally substituted" means that a compound is unsubstituted or has 1, 2, 3, 4, or 5 substituents at substitutable positions. Note that when a plurality of substituents are included, these substituents may be the same or different. In addition, the position of each substitution may be position 1, 2, 3, 4, 5, 6, 7, 8, or 9. Here, examples of the substituents include H, halogen, nitro, cyano, OH, $C_1$-6 alkyl, $C_{1-6}$ halogenoalkyl, $C_{1-6}$ hydroxyalkyl, $C_{1-6}$ alkylamino, $C_{3-6}$ cycloalkyl, $C_{2-6}$ alkenyl, $C_{2-6}$ halogenoalkenyl, $C_{2-6}$ hydroxyalkenyl, $C_{2-6}$ alkenylamino, $C_{3-6}$ cycloalkenyl, $C_{2-6}$ alkynyl, $C_{2-6}$ halogenoalkynyl, $C_{2-6}$ hydroxyalkynyl, $C_{2-6}$ alkynylamino, $C_{1-6}$ alkoxy, $C_{1-6}$ halogenoalkoxy, $C_{1-6}$ hydroxyalkoxy, $C_{1-6}$ alkoxyamino, $C_{1-6}$ alkoxyphenyl, trialkylsiloxy, alkyl diphenyl siloxy, aryl, and heteroaryl.

As used herein, the "$C_{1-6}$ halogenoalkyl" refers to $C_{1-6}$ alkyl that is substituted by one or more halogens. The number of halogens may be, for example, 1, 2, 3, 4, 5, 6, or 13. Also, the number may be between any two of the numbers indicated above. In addition, when two or more halogens are included, the kind of each halogen may be the same or different. Examples of $C_{1-6}$ halogenoalkyl include, chloromethyl, dichloromethyl, trichloromethyl, fluoromethyl, difluoromethyl, trifluoromethyl, bromomethyl, dibromomethyl, tribromomethyl, chloroethyl, dichloroethyl, trichloroethyl, fluoroethyl, difluoroethyl, and trifluoroehtyl.

As used herein, the "$C_{1-6}$ hydroxyalkyl" refers to $C_{1-6}$ alkyl that is substituted by one or more hydroxy groups. The number of the hydroxy groups may be, for example, 1, 2, 3, 4, 5, 6, or 13. Also, the number may be between any two of the numbers indicated above. Examples of $C_{1-6}$ hydroxyalkyl include hydroxymethyl, 1-hydroxyethyl, 2-hydroxyethyl, 2-hydroxy-n-propyl, and 2,3-dihydroxy-n-propyl.

As used herein, the "$C_{1-6}$ alkylamino" refers to $C_{1-6}$ alkyl that is substituted by one or more amino groups. The number of the amino groups may be, for example, 1, 2, 3, 4, 5, 6, or 13. Also, the number may be between any two of the numbers indicated above. Examples of $C_{1-6}$ alkylamino include methylamino and ethylamino.

As used herein, the "$C_{1-6}$ halogenoalkoxy" is equivalent to $C_{1-6}$ halogenoalkyl, the alkyl of which is replaced by alkoxy. Examples of $C_{1-6}$ halogenoalkoxy include fluoromethoxy, difluoromethoxy, trifluoromethoxy, 1-fluoroethoxy, 2-fluoroethoxy, 2-chloroethoxy, 2-bromoethoxy, (1,1-difluoro) ethoxy, (1,2-difluoro) ethoxy, (2,2,2-trifluoro) ethoxy, (1,1,2,2-tetrafluoro) ethoxy, (1,1,2,2,2-pentafluoro) ethoxy, 1-fluoron-n-propoxy, 1,1-difluoro-n-propoxy, 2,2-difluoro-n-propoxy, 3-fluoro-n-propoxy, (3,3,3-trifluoro)-n-propoxy, (2,2,3,3,3-pentafluoro)-n-propoxy, 4-fluoro-n-butoxy, (4,4,4-trifluoro)-n-butoxy, 5-fluoro-n-pentyloxy, (5,5,5-trifluoro)-n-pentyloxy, 6-fluoro-n-hexyloxy, (6,6,6-trifluoro)-n-hexyloxy, 2-fluorocyclopropoxy, and 2-fluorocyclobutoxy.

As used herein, the "$C_{1-6}$ hydroxyalkoxy" is equivalent to $C_{1-6}$ hydroxyalkyl, the alkyl of which is replaced by alkoxy. Examples of $C_{1-6}$ hydroxyalkoxy include 2-hydroxyethoxy, 2-hydroxy-n-propoxy, 3-hydroxy-n-propoxy, 2,3-dihydroxy-n-propoxy, and 2-hydroxycyclopropyl.

As used herein, the "$C_{1-6}$ alkoxyamino" is equivalent to $C_{1-6}$ alkylamino, the alkyl of which is replaced by alkoxy. Examples of $C_{1-6}$ alkoxyamino include methoxyamino and ethoxyamino.

As used herein, the term "aryl" refers to a $C_{6-14}$ monocyclic, dicyclic, or tricyclic aromatic hydrocarbon ring group. Examples of aryl include phenyl, naphthyl (e.g., 1-naphthyl, 2-naphthyl), tetrahydronaphthalenyl, indenyl, and fluorenyl. Particularly preferred are naphthyl or phenyl substituted with five halogens. Also, the aryl includes a ring group that is condensed with $C_{5-8}$ cycloalkene at its double bond position.

As used herein, the "heteroaryl" includes groups having 5 to 14 ring atoms within their rings, having a shared π electron system, and having 1 to 4 heteroatoms selected from the group consisting of N, S, and O. Examples of heteroaryl include thienyl, benzothienyl, furyl, benzofuryl, dibenzofuryl, pyrrolyl, imidazolyl, pyrazolyl, pyridyl, pyrazinyl, pyrimidinyl, pyridazinyl, tetrazolyl, oxazolyl, thiazolyl, and isooxazolyl. Particularly preferred is furyl that is substituted by one methyl group.

According to an embodiment of the present invention, the structure of a compound represented by the formula (1) preferably involves a configuration in which $R^1$, $R^2$, and $R^3$ are each H; and $R^4$ is at position 4 and represents H, F, Cl, nitro, OH, $CH_2OH$, methoxy, methoxymethoxy, or tert-butyl dimethyl siloxymethyl. It is particularly preferable that the structure of a compound represented by the formula (1) is as close as the structure of a compound represented by the formula (3) in view of an effect of treating malignant tumors or fibrosis. According to an embodiment of the present invention, it is preferable that the structure of a compound represented by the formula (2) is as close as the structure of a compound represented by the formula (4) in view of an effect of treating malignant tumors or fibrosis. According to an embodiment of the present invention, it is preferable that the structure of a compound represented by the formula (5) is as close as the structure of a compound represented by the formula (6) in view of an effect of treating malignant tumors or fibrosis. Note that the compounds represented by the formulas (3), (4), and (6) are sometimes referred to as IC-2, PN3-13, and HC-1, respectively. As used herein, the meaning of PN3-13 is same as of PN-3-13.

[Chemical Formula 3]

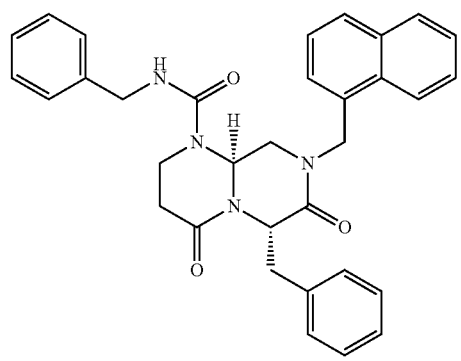

(3)

[Chemical Formula 4]

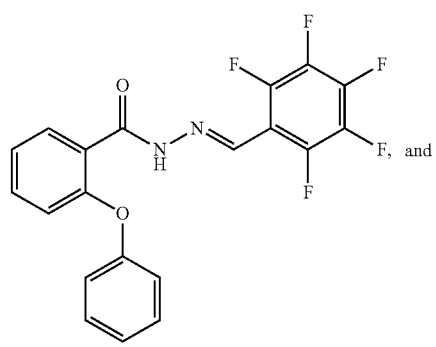

(4)

[Chemical Formula 6]

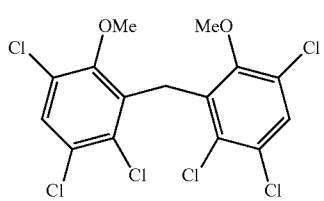

(6)

As used herein, examples of the "salt" include, but are not particularly limited to, anionic salts that are formed by using any acidic group (e.g., carboxyl) and cationic salts that are formed by using any basic group (e.g., amino). Examples of the salts include inorganic salts, organic salts, and salts disclosed in the article (Berge, Bighley, and Monkhouse, J. Pharm. Sci., 1977, 66, 1-19). The examples further include metal salts, ammonium salts, salts of an organic base, salts of an inorganic acid, salts of an organic acid, and salts of a basic or acidic amino acid. Examples of the metal salts include alkali metal salts (e.g., sodium salts, potassium salts), alkali earth metal salts (e.g., calcium salts, magnesium salts, barium salts), and aluminum salts. Examples of the salts of an organic base include salts of trimethylamine, triethylamine, pyridine, picoline, 2,6-lutidine, ethanolamine, diethanolamine, triethanolamine, cyclohexylamine, dicyclohexylamine, or N,N'-dibenzylethylenediamine. Examples of the salts of an inorganic acid include salts of hydrochloric acid, hydrobromic acid, nitric acid, sulfuric acid, or phosphoric acid. Examples of the salts of an organic acid include salts of formic acid, acetic acid, trifluoro acetic acid, phthalic acid, fumaric acid, oxalic acid, tartaric acid, maleic acid, citric acid, succinic acid, malic acid, methanesulfonic acid, benzenesulfonic acid, or p-toluenesulfonic acid. Examples of the salts of a basic amino acid include salts of arginine, lysine, or ornithine. Examples of the salts of an acidic amino acid include salts of aspartic acid or glutamic acid.

As use herein, the term "solvate" refers to a compound formed by using a solute and a solvent. J. Honig et al., The Van Nostrand Chemist's Dictionary P650 (1953) can be consulted regarding the solvate. If the solvent is water, the solvate formed is a hydrate. Preferably, the solvent does not interfere with the biological activity of the solute. Examples of such a preferable solvent include, but are not limited to, water, ethanol, and acetic acid. The most preferred solvent is water. A compound or a salt thereof according to an embodiment of the present invention absorbs moisture when contacting the air or recrystallized. They may have hygroscopic moisture or become a hydrate. As used herein, the term "isomer" includes a molecule, the molecular formula of which is identical, but the structure of which is different. Examples of the isomer include enantiomers, geometric (cis/trans) isomers, and isomers (diastereomers) having one or more chiral centers that are not mirror images of one another. As used herein, the term "prodrug" includes a precursor compound in which when the above compound is administered to a subject, a chemical change occurs due to metabolic processes or various chemical reactions to give rise to a compound, a salt thereof, or a solvate thereof according to the present invention. With regard to the prodrug, the article (T. Higuchi and V. Stella, "Pro-Drugs as Novel Delivery Systems", A.C.S. Symposium Series, Volume 14) can be referred to.

As used herein, examples of a "malignant tumor" include tumors caused by a mutation in a normal cell. The malignant tumors occur in all the organs and tissues in the body. The malignant tumor is, for example, at least one kind selected from the group consisting of lung cancer, esophagus cancer, gastric cancer, liver cancer, pancreatic cancer, renal cancer, adrenal cancer, biliary tract cancer, breast cancer, colon cancer, small intestinal cancer, ovarian cancer, uterine cancer, bladder cancer, prostate cancer, ureteral cancer, renal pelvis cancer, ureteral cancer, penile cancer, testicular cancer, brain tumor, cancer in central nervous system, cancer in peripheral nervous system, head and neck carcinoma, glioma, glioblastoma multiforme, skin cancer, melanoma, thyroid cancer, salivary gland cancer, malignant lymphoma, carcinoma, sarcoma, and hematological malignancies. The above liver cancer may be, for example, an epithelial tumor or nonepithelial tumor, and may be hepatocyte carcinoma or cholangiocellular carcinoma. Examples of the above skin cancer include basal cell carcinoma, squamous cell carcinoma, and malignant melanoma.

As used herein, the term "cancer stem cell" includes a cell that generates cancer cells. This cancer stem cell includes a cell expressing a cancer stem cell marker. Examples of the cancer stem cell marker include CD44, CD90, CD133, and EpCAM.

The "fibrosis" has been known as a symptom caused by loss of normal function due to tissue sclerosis in which the volume of a connective tissue mass including tissue components such as collagen is increased and a normal tissue is replaced by the connective tissue. Fibrosis occurs in, for example, respective tissues such as the liver, lung, kidney, heart, and skin. Also, occurrence of a large amount of fibrosis in a hepatic tissue, for example, may result in hepatic cirrhosis, leading to liver cancer. Each tissue, other than a liver tissue, may harbor a malignant tumor while fibrosis progresses. The term "fibrosis" include a disease accompanied by fibrosis. Examples of the disease accompanied by fibrosis include the above tissue fibrosis, cirrhosis, and malignant tumors accompanied by fibrosis.

As used herein, the term "treatment" includes exerting a prophylactic effect, an inhibitory effect, or a symptom-improving effect on a disease of a subject or on one or more symptoms involving the disease. As used herein, the "therapeutic drug" may be a pharmaceutical composition containing an active ingredient and at least one pharmacologically acceptable carrier. The pharmaceutical composition can be produced by any process known in the art of drug formulation. Examples of the process include: mixing an active ingredient with the above carrier. In addition, the dosage form of the drug is not limited as long as the drug can be used for treatment. The drug may be an active ingredient alone or a mixture of an active ingredient and any component. Further, examples of the dosage form of the above carrier include, but are not particularly limited to, a solid and liquid (e.g., a buffer). Note that examples of a therapeutic drug for malignant tumors include: a drug (prophylactic) used for preventing a malignant tumor; a drug for inhibiting relapse of a malignant tumor; and a drug for inhibiting proliferation of a malignant tumor cell. Examples of a therapeutic drug for cancer stem cells include: an agent for treating a cancer stem cell as a target; a therapeutic drug for malignant tumors derived from a cancer stem cell; and an inhibitor for cancer stem cells.

A drug administration route effective in treatment is preferably used. Examples of the administration route include intravenous, subcutaneous, intramuscular, intraperitoneal, and oral administration. Examples of the dosage form may include an injection, a capsule, a tablet, and granules. In addition, an aqueous solution for an injection may be combined with, for example, a saline solution, sugar (e.g., trehalose), NaCl, or NaOH. Further, the drug may be formulated with, for example, a buffer (e.g., a phosphate buffer) and/or a stabilizer.

A dosage is not particularly limited, and may be, for example, 0.001, 1, 10, 100, or 1000 mg/kg body weight per administration. The dosage may be between any two of the above values. An administration interval is not particularly limited, and the drug may be dosed, for example, once or twice per 1, 7, 14, 21, or 28 days. The drug may be dosed once or twice per period between any two of the above values. In addition, the dosage, the administration interval, and the administration method can be appropriately selected depending on the age, body weight, symptom, affected organ, etc., of a patient. Further, the drug preferably contains a therapeutically effective amount or a dose, which is effective in exerting a desired effect, of an active ingredient.

The effect of treating malignant tumors may be evaluated by imaging, endoscopic examination, biopsy, or detection of a malignant tumor marker. In addition, the effect of treating cancer stem cells may be evaluated by imaging, endoscopic examination, biopsy, or detection of a cancer stem cell marker. In addition, the effect of treating fibrosis may be evaluated by imaging, endoscopic examination, biopsy, or detection of a fibrosis marker. One may make such a judgment that when the level of a marker in a patient or a patient-derived sample (e.g., a tissue, cells, a cell population, or blood) is significantly decreased after administration of a therapeutic drug, there is a therapeutic effect. At this time, the level of a marker after administration of a therapeutic drug may be 0.7, 0.5, 0.3, or 0.1 times the level before the administration (or of a control). Alternatively, one may make such a judgment that when the number of marker-positive cells in the patient-derived sample is significantly decreased after administration of the therapeutic drug, there is a therapeutic effect. At this time, the number of marker-positive cells after administration of the therapeutic drug may be 0.7, 0.5, 0.3, or 0.1 times the number before the administration (or of a control). Note that in Example 2 below, the therapeutic effect was evaluated by using mice in which CD44-positive HuH7 cells had been subcutaneously transplanted. The present inventors also replaced the above CD44-positive HuH7 cells by unsorted HuH7 cells. This experiment has demonstrated that IC-2 exhibits an effect of treating a malignant tumor.

In addition, with regard to the therapeutic effect of treating a malignant tumor, one may make such a judgment that when the growth rate of patient-derived test cells is significantly decreased after administration of the therapeutic drug, there is a therapeutic effect. At this time, the growth rate of patient-derived test cells after administration of the therapeutic drug may be reduced to 0.7, 0.5, 0.3, or 0.1 times of the rate before the administration (or of a control). In addition, as used herein, the term "significantly" may include a case of $p<0.05$ or $p<0.01$ when Student's t test (one-sided or two-sided), for example, is used to evaluate a statistically significant difference. Also, the term may include a state in which there is a substantial difference.

As used herein, examples of the "patient" include human and non-human mammals (e.g., at least one of a mouse, guinea pig, hamster, rat, mouse, rabbit, pig, sheep, goat, cow, horse, cat, dog, marmoset, monkey, and chimpanzee). Meanwhile, the patient may be a patient who is determined or diagnosed as having the onset of a malignant tumor or fibrosis. In addition, the patient may be a patient who needs treatment of a malignant tumor or fibrosis. Also, the patient may be a patient who is determined or diagnosed as having a significantly larger number of cancer stem cells in a tissue than healthy individuals. Note that the determination or diagnosis may be performed by imaging, endoscopic examination, biopsy, or detection of various markers.

As used herein, the wording "a state in which cell proliferation is inhibited" includes a state in which the growth rate of test cells is significantly less than that before drug treatment. The growth rate can be evaluated by measuring the level of proliferation of cells during a given period of time. The level of proliferation may be measured, for example, visually or by using absorbance as an index. Alternatively, the level of proliferation may be measured by using, as an index, the level of a malignant tumor marker in a patient or a patient-derived sample. As used herein, the wording "inhibiting a cancer stem cell" includes, for example, inhibiting proliferation of a cancer stem cell and inhibiting the function of a cancer stem cell (e.g., inhibiting sphere formation, inhibiting marker expression).

An embodiment of the present invention provides a drug for inhibiting expression of a marker for a malignant tumor cell, a cancer stem cell, or fibrosis, which drug includes at least one compound selected from the group consisting of compounds represented by formulas (1), (2), and (5), a salt thereof, or a solvate thereof. An embodiment of the present invention provides a drug for inhibiting formation of a sphere from a malignant tumor or of cancer stem cells, which drug includes at least one compound selected from the group consisting of compounds represented by formulas (1), (2), and (5), a salt thereof, or a solvate thereof. This drug for inhibiting formation of a sphere may be used for treatment of malignant tumors or cancer stem cells.

An embodiment of the present invention provides a treatment method comprising the step of administering to a patient a low-molecular weight compound contained in a therapeutic drug according to any of the above embodiments. An embodiment of the present invention provides use of a low-molecular weight compound contained in the therapeutic drug according to any of the above embodiments in the manufacture of the therapeutic drug. An embodiment of the present invention provides a growth-inhibiting method comprising the step of administering to a patient a low-molecular-weight compound contained in the drug for inhibiting proliferation according to any of the above embodiments. An embodiment of the present invention provides use of a low-molecular-weight compound contained in the drug for inhibiting proliferation according to any of the above embodiments in the manufacture of the drug. An embodiment of the present invention provides a method for inhibiting relapse of a malignant tumor, the method comprising the step of administering to a patient a low-molecular weight compound contained in the drug for inhibiting relapse according to any of the above embodiments. An embodiment of the present invention provides use of a low-molecular-weight compound contained in the drug for inhibiting relapse according to any of the above embodiments in the manufacture of the drug.

An embodiment of the present invention provides at least one compound selected from the group consisting of compounds represented by the formula (1), a salt thereof, or a solvate thereof, wherein $R^1$, $R^2$, and $R^3$ are each H; and $R^4$ is at position 4 and represents F, $C_1$, nitro, OH, $CH_2OH$, methoxy, methoxymethoxy, or tert-butyl dimethyl siloxymethyl. This compound, a salt thereof, or a solvate thereof may be used to treat malignant tumors, cancer stem cells, and/or fibrosis.

An embodiment of the present invention provides a drug for inhibiting a Wnt/8-catenin signal, which drug includes at least one compound selected from the group consisting of compounds represented by the formula (1), a salt thereof, or a solvate thereof, wherein $R^1$, $R^2$, and $R^3$ are each H; and $R^4$ is at position 4 and represents F, $C_1$, nitro, OH, $CH_2OH$, methoxy, methoxymethoxy, or tert-butyl dimethyl siloxymethyl. This compound, a salt thereof, or a solvate thereof may be used to inhibit a Wnt/β-catenin signal. The drug for inhibiting a Wnt/β-catenin signal may be used for various applications in vitro or in vivo. The drug for inhibiting a Wnt/β-catenin signal may be used for treatment of disease that can be ameliorated by, for example, an inhibitory effect on a Wnt/β-catenin signal.

Any document and (patent or patent application) publication, which are cited herein, are incorporated by reference in its entirety.

As used herein, the term "or" may be used when "at least one" matter listed in the text of specification can be employed. The same applies to the term "or". As used herein, when the wording "between any two of the above values" is indicated, the two values are inclusive in the range. As used herein, the phrase "from A to B" means "A or more and B or less".

As described above, the embodiments of the present invention have been illustrated. These embodiments are examples of the present invention. Accordingly, various configurations other than the above embodiments can be adopted. In addition, combinations among the above-described embodiments can also be employed.

EXAMPLES

Hereinafter, the present invention is further illustrated by referring to Examples. The present invention, however, is not limited to them.

<Example 1> Experiment of Inhibiting Cancer Cells and Cancer Stem Cells 1.1 Reagents Used DMEM: Dulbecco's Modified Eagle's Medium Powder (Nissui, Hiroshima, Japan), 10 mL of 10% $NaHCO_3$, 5 mL of 100× glucose, 10 mL of 50× glutamine, 10% fetal bovine serum (FBS) (EQUITECH-BIO, Texas, USA)

PBS (−): 137 mM NaCl, 8.10 mM $Na_2HPO_4·12H_2O$, 2.68 mM KCl, 1.47 mM $KH_2PO_4$

Trypsin/EDTA solution: (Nacalai Tesque) 0.25% Trypsin, 1 mM EDTA

Low-molecular-weight compounds: IC-2 (formula (3)), PN3-13 (formula (4)), HC-1 (formula (6)), and ICG-001 were synthesized in accordance with a process described in WO2012/141038.

1.2 Cell Culture

HuH7 cells (a liver cancer cell line) were cultured in a DMEM on a 10-cm cell culture dish (TPP Techno Plastic Products AG, Trasadingen, Switzerland) at 5% $CO_2$, 37° C., and a humidity of 100%. After the cells were grown to 70 to 90% confluency, 200 μL of a Trypsin/EDTA solution was added thereto to detach the cells. The cells were centrifuged at 1000 rpm for 5 min at room temperature for recovery. Then, the cells in one dish were divided into four dishes and subcultured.

1.3 Inhibitory Effect on Cancer Cells (WST Assay)

When a concentration-dependent anti-tumor effect was examined, HuH7 cells at 70 to 90% confluency were collected, and $1 \times 10^4$ cells were seeded in each well of a 96-well plate (FALCON). When a time-dependent anti-tumor effect was examined, $5 \times 10^3$ cells were seeded. Twenty-four hours after the seeding, the cells were treated with IC-2, PN3-13, or HC-1, and further incubated at 37° C. DMSO was used as a control.

The concentration of each low-molecular-weight compound was provided below. IC-2:0, 1, 5, 10, 25, 50 μM; PN3-13:0, 1, 5, 10, 25, 50 μM; and HC-1:0, 1, 5, 10, 25, 50 μM. When the concentration-dependent anti-tumor effect was examined, 100 μL of 10% TetraColor ONE (SEIKAGAKU CORPORATION, Tokyo, Japan) was added at 4 days after the chemical treatment. When the time-dependent anti-tumor effect was examined, 100 μL of 10% TetraColor ONE was added at 0, 1, 2, and 4 days after the chemical treatment. Then, the cells were incubated at 37° C. for 45 min. After that, absorbance (at a measurement wavelength of 450 nm/a control wavelength of 600 nm) was measured by a 96-well microplate reader (TECAN, Zurich, Switzerland). The absorbance of cells was calculated by subtracting the absorbance of reagent blank from the measured result, and was then converted to the viable cell count. Also, the $IC_{50}$ of each low-molecular-weight compound was determined by using an equation:

$IC_{50} = 10^{\{LOG(A/B) \times (50-C)/(D)-C)+LOG(B)\}}$, wherein A denotes a concentration higher than 50%; B denotes a concentration lower than 50%; C denotes the rate of inhibition at B; and D denotes the rate of inhibition at A.

Figure 2:
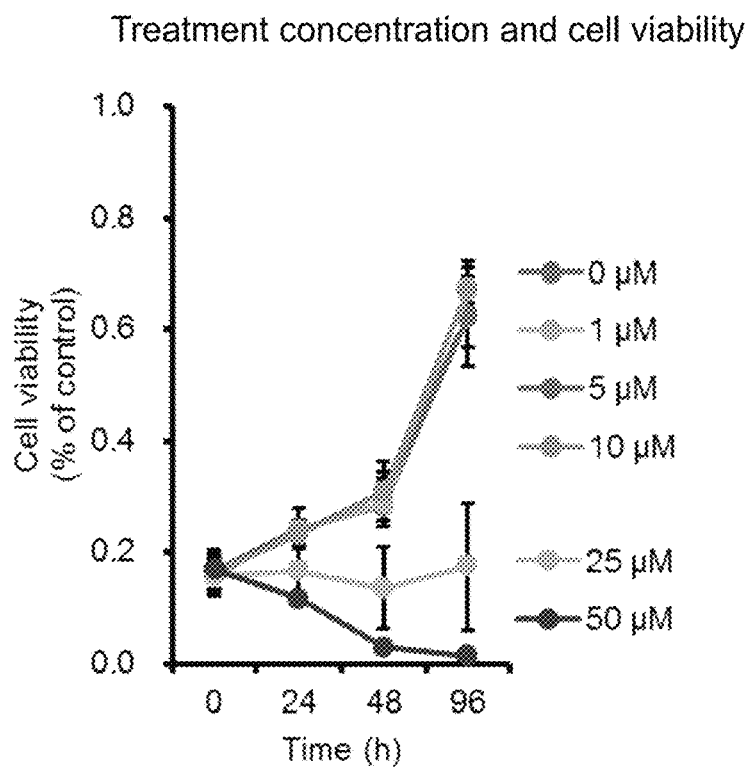
FIG. 2 is a graph showing the results of checking the (time-dependent) cell viability of liver cancer cells after IC-2 treatment.
Figure 3:
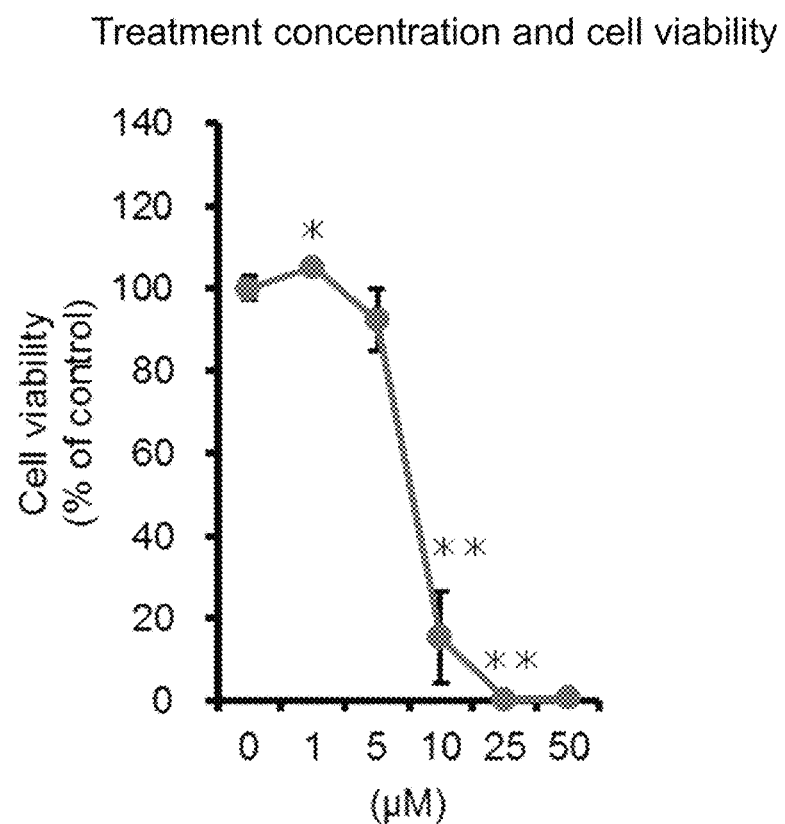
FIG. 3 is a graph showing the results of checking the (concentration-dependent) cell viability of liver cancer cells after PN3-13 treatment.
Figure 4:
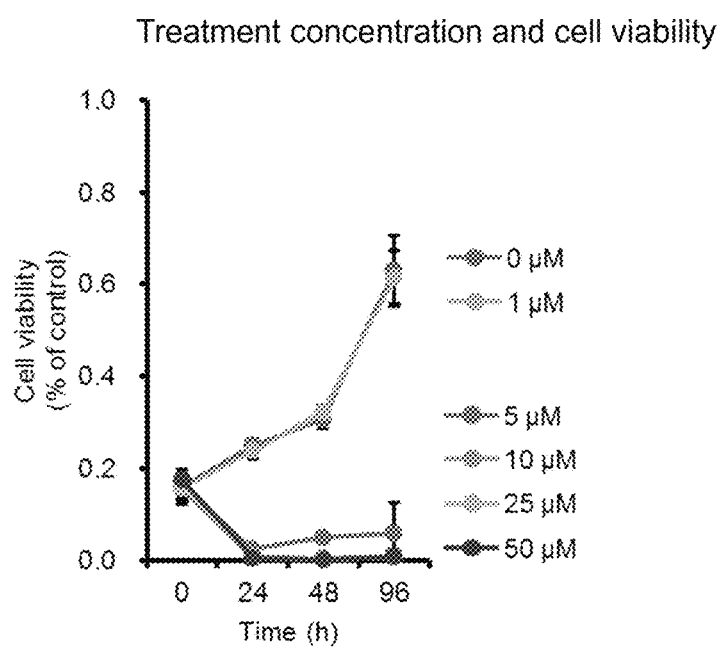
FIG. 4 is a graph showing the results of checking the (time-dependent) cell viability of liver cancer cells after PN3-13 treatment.
Figure 5:
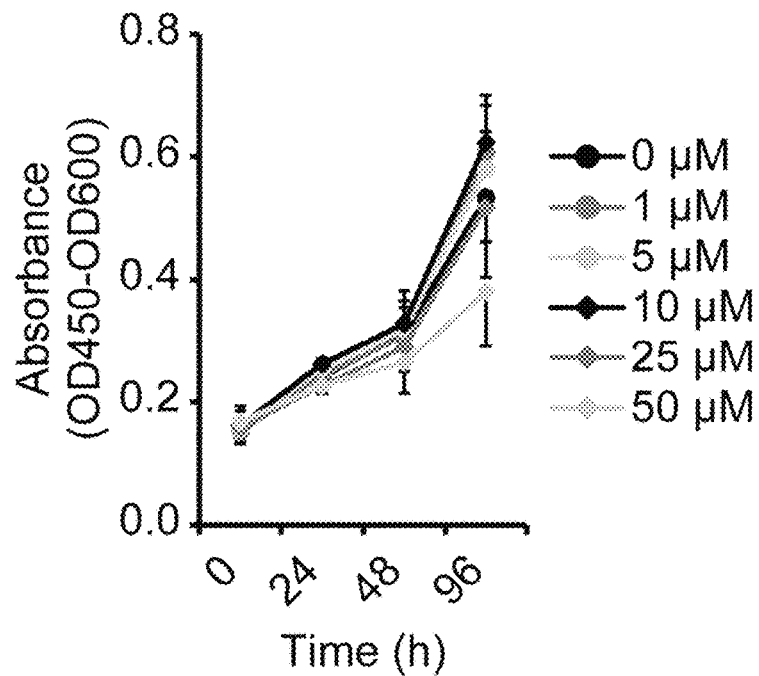
FIG. 5 is a graph showing the results of checking the (time-dependent) cell viability of liver cancer cells after HC-1 treatment.

The results demonstrate that the IC-2 treatment significantly inhibited proliferation of HuH7 cells (FIGS. 1 and 2). In addition, the PN3-13 treatment also significantly inhibited proliferation of HuH7 cells (FIGS. 3 and 4). Further, the HC-1 treatment also inhibited proliferation of HuH7 cells (FIG. 5).

1.5 Inhibitory Effect on Cancer Stem Cells (FACS Analysis)

The following protocol was used to investigate an inhibitory effect of each low-molecular-weight compound on cancer stem cells. CD44, a cancer stem cell marker, was used as an index. HuH7 cells at 70 to 90% confluency were collected and $1.5 \times 10^6$ cells were seeded on a 10-cm dish (TPP Techno Plastic Products AG, Trasadingen, Switzerland). After 15 hours, the cells were treated with each of Hexachlorophene (15 μM), ICG-001 (15 μM), PKF118-310 (5 μM), IC-2 (50 M), PN3-13 (10 μM), and 5-FU (0.5 μM) and were incubated at 37° C. DMSO, which was a solvent for each of the low-molecular-weight compounds and anticancer drugs, was used as a control. Two days after the chemical treatment, the cells on a dish were collected. Next, the cells were centrifuged at 1000 rpm for 5 min at 4° C. to remove a supernatant. Then, the cells were washed twice with 1 mL of 0.5% FBS/2 mM EDTA/PBS. After that, the cells were suspended in 500 μL of 5% BSA/0.5% FBS/2 mM EDTA/PBS and blocked once for 15 min at 4° C.

Next, 5 μL of an anti-human CD44 monoclonal antibody (Cell Signaling Technology Inc., Danvers, MA, USA) was added. Then, the cells were suspended and a primary antibody reaction was performed in a dark room for 10 min at 4° C. After that, the cells were washed 3 times with 1 mL of PBS. After 1.0 μg of an Alexa 488-labeled goat anti-mouse IgG antibody (Life Technologies Corp., Carlsbad, CA, USA) was added, the mixture was resuspended and a secondary antibody reaction was performed in a dark room for 10 min at 4° C. Subsequently, the cells were washed 3 times with 1 mL of PBS, and further washed once with 5%

FBS/2 mM EDTA/DMEM. Afterwards, the cells were resuspended in 500 μL of 5% FBS/2 mM EDTA/PBS and the mixture was made to pass through a tube with a 40-μm mesh filter (Becton, Dickinson and Company, Franklin, Lakes NJ, USA). A Beckman Coulter-MoFlo XDP (Beckman Coulter Inc., Fullerton, CA, USA) was used to conduct analysis. Note that a significant difference was evaluated by using Student's t-test (two-tailed). In the graphs, * means $p<0.05$ and ** means $p<0.01$ (this applies to all the graphs in the Examples) (n=5).

Figure 6:
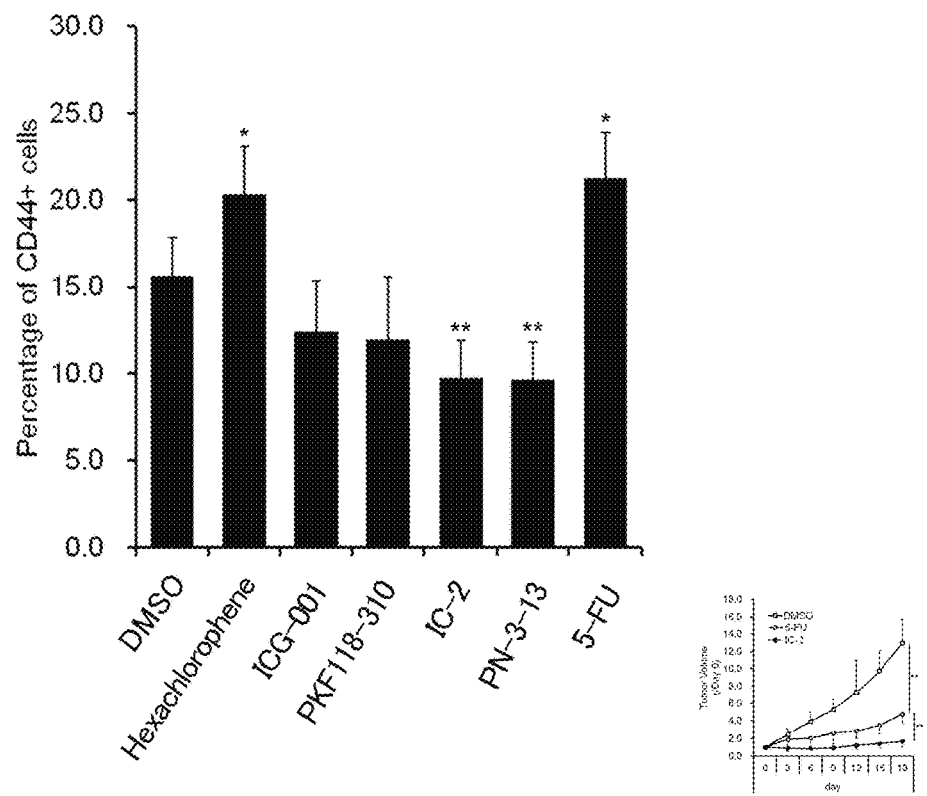
FIG. 6 is a graph showing the results of counting the number of CD44-positive cells after cancer stem cells were treated with low-molecular weight compounds.

The results demonstrate that when IC-2 and PN3-13 were used, the number of cancer stem cells was significantly less than that of the control (FIG. 6). However, use of 5-FU, a representative anti-cancer drug, rather increased the number of cancer stem cells.

<Example 2> Liver Cancer Model Mice Were Used to Evaluate Therapeutic Effect of Treating Malignant Tumor CD44-positive HuH7 cells were subcutaneously transplanted into mice. The mice were then divided into 3 groups (DMSO group: 5 mice; 5-FU group: 4 mice; and IC-2 group: 4 mice). Subsequently, 30 mg/kg of 5-FU, 50 mg/kg of IC-2, or DMSO (as a control), which was a solvent for each chemical, was intraperitoneally administered every 3 days. The body weight and the tumor length and width of each mouse were measured every 3 days. The tumor volume was calculated by using the following equation: Tumor volume=Length×(Width) 2×0.5. The volume at Day 0 was used to normalize each tumor volume, and then a graph was created. To sufficiently evaluate an effect of 5-FU, the dosage that was usually 25 mg/kg in research articles was doubled to set a 5-FU dose. The IC-2 concentration corresponding to a concentration at which a Wnt/β-catenin signal was inhibited in vitro was calculated. Then, the concentration was doubled to set an IC-2 dose.

Figure 7:
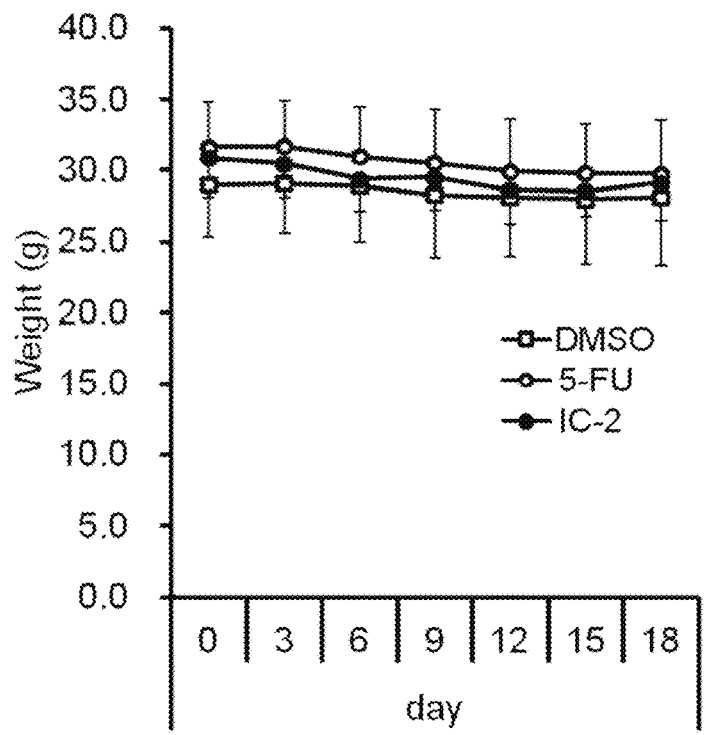
FIG. 7 is a graph showing the time-course of the change in the body weight of each of liver cancer model mice.
Figure 8:
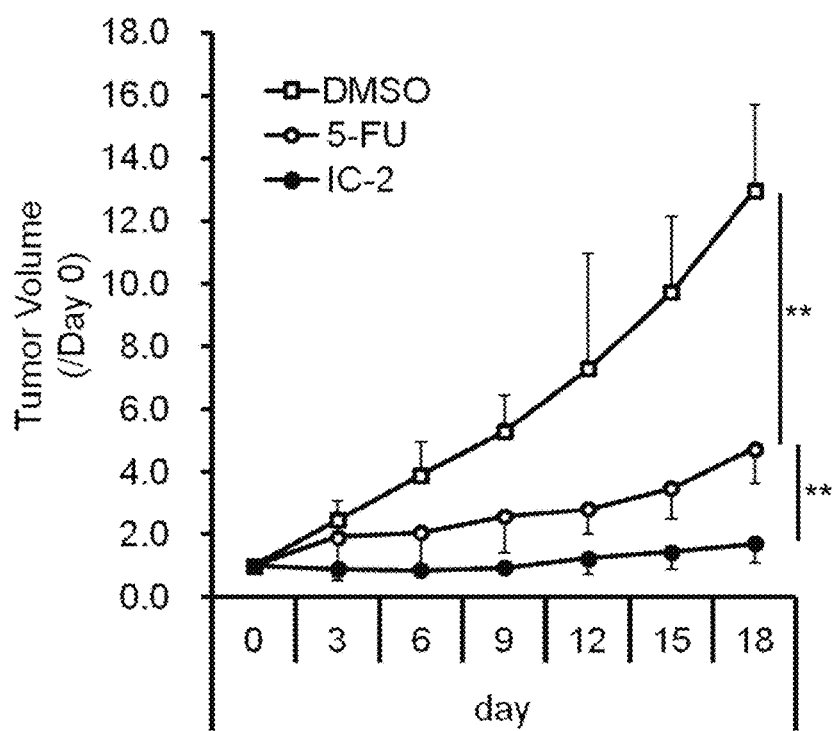
FIG. 8 is a graph showing the treatment efficacy when liver cancer model mice were treated.

The above resulted in no observable change in the body weight in the case of administration of any of IC-2 and 5-FU (FIG. 7). This means that it is possible to safely administer any of IC-2 and 5-FU. Further, IC-2 gave a significantly higher therapeutic effect of treating a malignant tumor than that of 5-FU (FIG. 8).

<Example 3> Effect on Sphere Formation Capability

First, HuH7 cells were collected. Next, the cells were stained with an anti-human CD44 monoclonal antibody (Cell Signaling Technology Inc., Danvers, MA, USA)), and then with an Alexa 488-labeled goat anti-mouse IgG antibody. After that, a Beckman Coulter-MoFlo XDP (Beckman Coulter Inc., Fullerton, CA, USA) was used to sort the cells into a CD44-negative fraction and a CD44-positive fraction. The sorted cells were seeded at $5×10^4$ cells/well on a 24-well ultra-low-attachment multiwell plate (Corning, NY, USA). Subsequently, the cells were cultured at 37° C. in the presence of 5% $CO_2$ in a DMEM/Nutrient Mixture F-12 Ham (Sigma-Aldrich, St. Louis, MO, USA) containing 20 ng/ml of recombinant human epidermal growth factor, 20 ng/mL of human basic fibroblast growth factor, 1× B27, and L-glutamine. Twenty-four hours after the plating, 1% DSMO, 50 μM IC-2, and 10 μM PN-3-13 were each added to the corresponding well and the cells were further cultured. One week after the chemical treatment, the number of spheres (with a size of 100 μm or larger) in 15 visual fields/well was counted.

Figure 9:
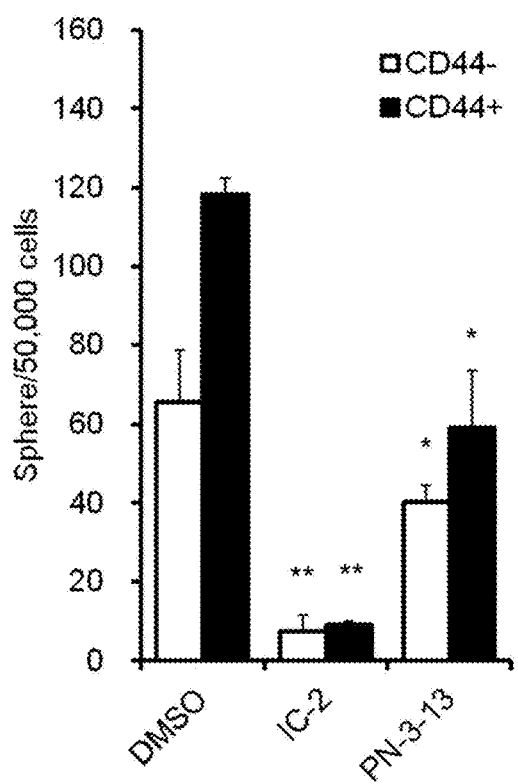
FIG. 9 is a graph showing the results of testing an effect of each low-molecular-weight compound on sphere formation capability.

The results demonstrated that IC-2 and PN-3-13 inhibited formation of spheres of the CD44-negative and CD-44 positive HuH7 cells (FIG. 9). This means that IC-2 and PN-3-13 inhibited a function of cancer cells and cancer stem cells.

<Example 4> FACS Analysis of Cancer Stem Cells 4.1 CD90 (Cancer Stem Cell Marker)

A liver cancer cell line HLF was seeded at $1.5×10^6$ cells/dish on 10-cm dishes. Next, the cells were cultured at 37° C. and 5% $CO_2$. After 24 hours, 1% DSMO, 0.5 μM 5-FU, or 50 M IC-2 was added thereto and the cells were further incubated. Two days after the chemical treatment, the cells were harvested. Then, the cells were blocked in 0.5% BSA/0.5% FBS/2 mM EDTA/PBS. Subsequently, 5 μL, of an APC-labeled mouse anti-human CD90 antibody (BD Biosciences, San Jose, CA, USA) was added to 500 μL of a cell suspension and the resulting mixture was resuspended and incubated at 4° C. for 10 min to carry out a primary antibody reaction. After the antibody reaction, the cells were washed twice with 0.5% FBS/2 mM EDTA/PBS and once with 5% FBS/2 mM EDTA/DMEM. Next, the cells were resuspended in 500 μL of 5% FBS/2 mM EDTA/PBS. Then, 1 μg/mL of propidium iodide was added thereto. After that, the mixture was made to pass through a tube with a 40-μm mesh filter. Finally, a Beckman Coulter-MoFlo XDP was used to analyze CD90-expressing cells. The concentration of 5-FU was determined on the basis of the $IC_{50}$ concentration at 24 hours in a WST assay. The concentration of IC-2 was determined on the basis of a concentration at which a Wnt/β-catenin signal was inhibited.

Figure 10:
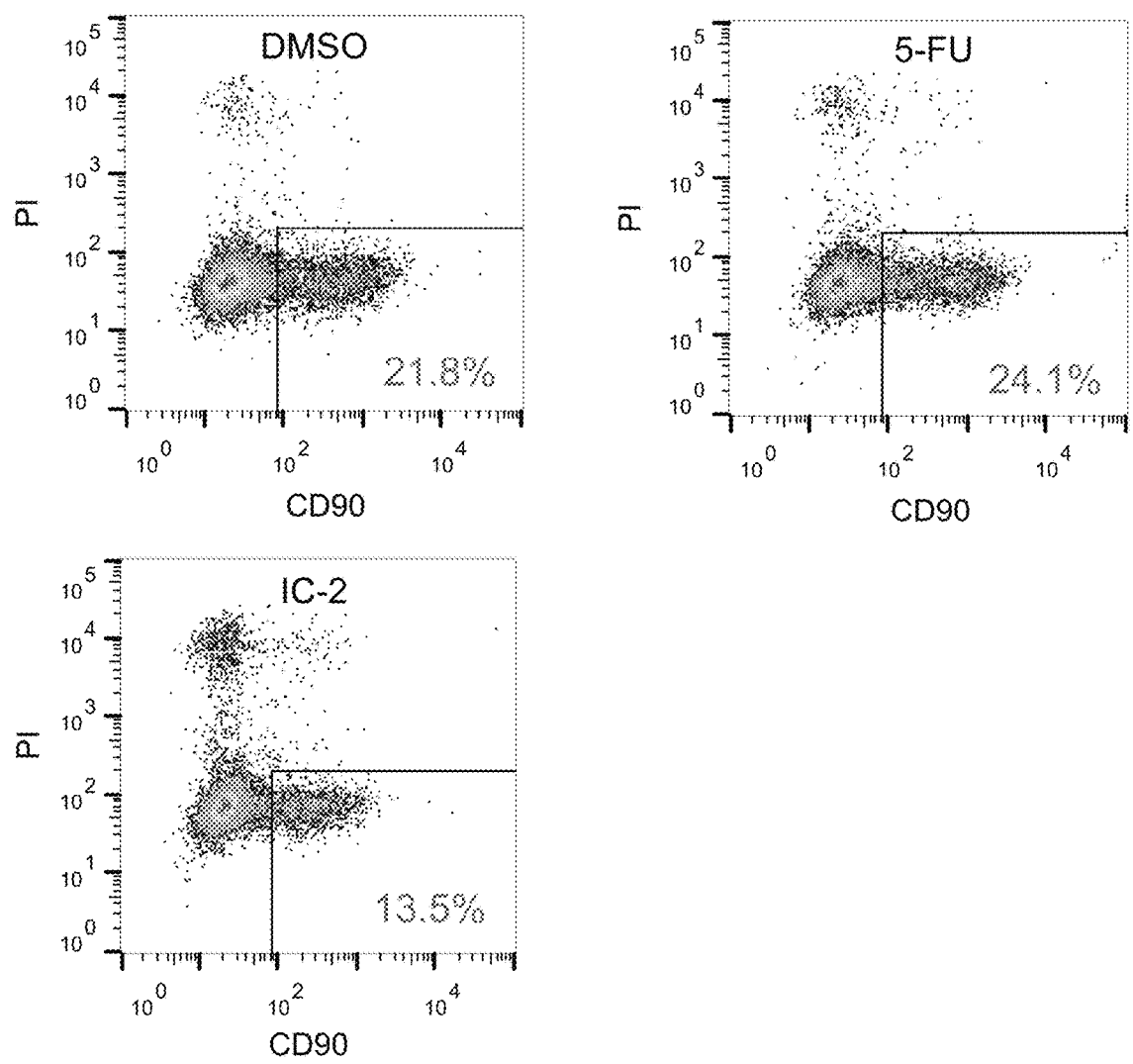
FIG. 10 is graphs showing the results of counting the number of CD90-positive cells after cancer stem cells were treated with low-molecular-weight compounds.

The results demonstrated that the proportion of the CD90-expressing cells was 21.8% for DMSO, 24.1% for 5-FU, and 13.5% for IC-2 (FIG. 10). That is, IC-2 exerted a superior inhibitory effect on liver cancer stem cells.

4.2 CD133 (Cancer Stem Cell Marker)

A liver cancer cell line HepG2 was seeded at $1.5×10^6$ cells/dish on 10-cm dishes. Next, the cells were cultured at 37° C. and 5% $CO_2$. After 24 hours, 1% DSMO, 0.5 μM 5-FU, or 50 μM IC-2 was added thereto and the cells were further incubated. Then, the cells were harvested at two days after the chemical treatment. Meanwhile, the cells were blocked in 0.5% BSA/0.5% FBS/2 mM EDTA/PBS. Subsequently, 50 μL of an anti-human CD133 monoclonal antibody (Miltenyi Biotec) was added to 500 μL of a cell suspension and the resulting mixture was resuspended and incubated at 4° C. for 10 min to carry out a primary antibody reaction. After the primary antibody reaction, the cells were washed 3 times with 1 mL of PBS. After 1.0 μg of an Alexa 488-labeled goat anti-mouse IgG antibody (Life Technologies Corp., Carlsbad, CA, USA) was added, the mixture was resuspended and a secondary antibody reaction was performed in a dark room for 10 min at 4° C. Thereafter, the cells were washed twice with 5% FBS/2 mM EDTA/PBS and once with 5% FBS/2 mM EDTA/DEME. Next, the cells were resuspended in 500 μL of 5% FBS/2 mM EDTA/PBS. Then, 1 g/mL of propidium iodide was added thereto. After that, the mixture was made to pass through a tube with a 40-μm mesh filter. Finally, a Beckman Coulter-MoFlo XDP was used to analyze CD133-expressing cells.

Figure 11:
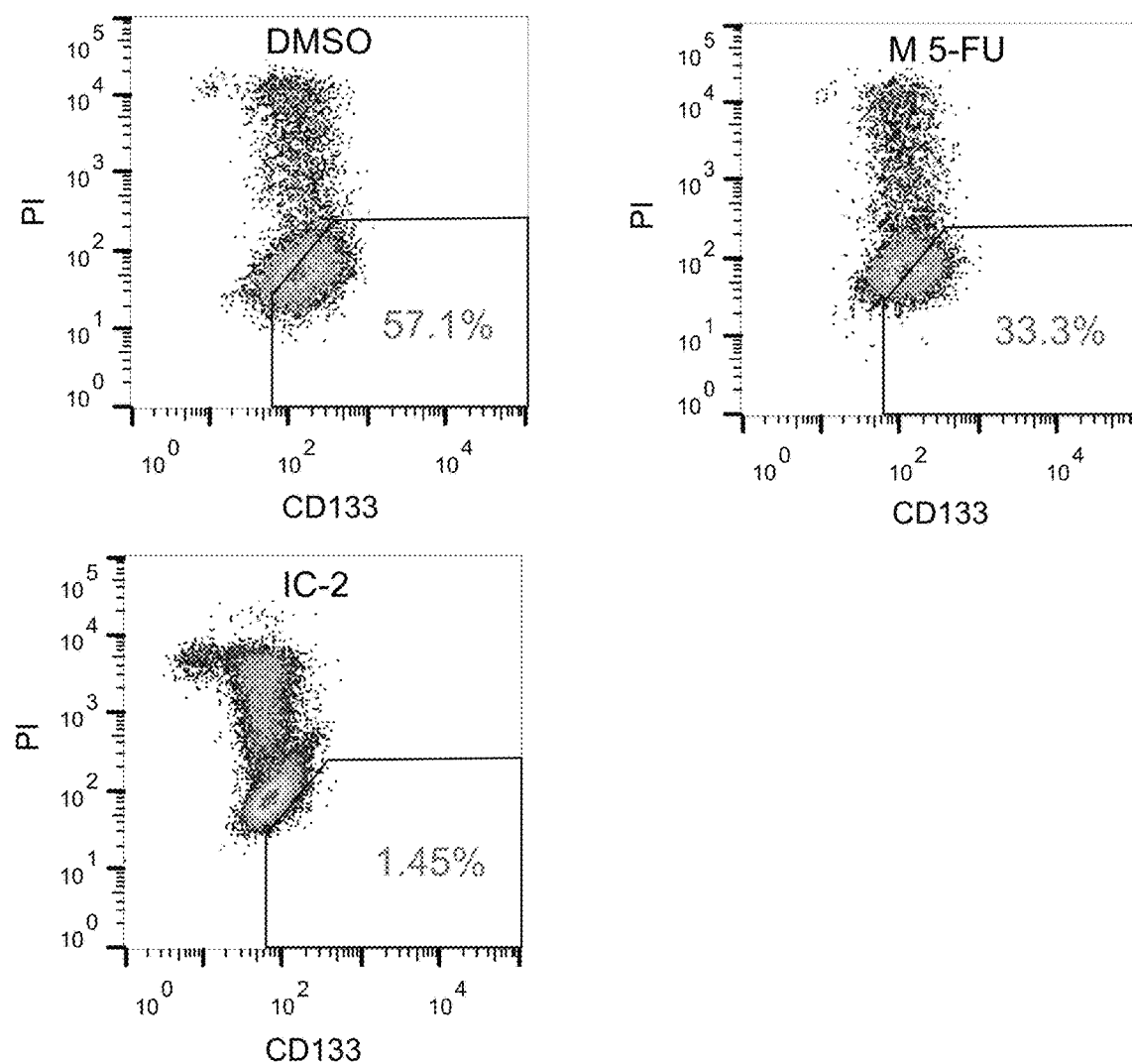
FIG. 11 is graphs showing the results of counting the number of CD133-positive cells after cancer stem cells were treated with low-molecular-weight compounds.

The results demonstrated that the proportion of the CD133-expressing cells was 57.1% for DMSO, 33.3% for 5-FU, and 1.45% for IC-2 (FIG. 11). That is, IC-2 exerted a superior inhibitory effect on liver cancer stem cells.

4.3 EpCAM (Cancer Stem Cell Marker)

A liver cancer cell line HepG2 was seeded at $1.5 \times 10^6$ cells/dish on 10-cm dishes. Next, the cells were cultured at 37° C. and 5% $CO_2$. After 24 hours, 1% DSMO, 0.5 µM 5-FU, or 50 µM IC-2 was added thereto and the cells were further incubated. Then, the cells were harvested at two days after the chemical treatment. Meanwhile, the cells were blocked in 0.5% BSA/0.5% FBS/2 mM EDTA/PBS. Subsequently, 0.3 µL of an anti-human EpCAM monoclonal antibody (Cell Signaling Technology Inc., Danvers, MA, USA) was added to 500 µL of a cell suspension and the resulting mixture was resuspended and incubated at 4° C. for 10 min to carry out a primary antibody reaction. After the primary antibody reaction, the cells were washed 3 times with 1 mL of PBS. After 1.0 µg of an Alexa 488-labeled goat anti-mouse IgG antibody (Life Technologies Corp., Carlsbad, CA, USA) was added, the mixture was resuspended and a secondary antibody reaction was performed in a dark room for 10 min at 4° C. Thereafter, the cells were washed twice with 5% FBS/2 mM EDTA/PBS and once with 5% FBS/2 mM EDTA/DEME. Next, the cells were resuspended in 500 µL of 5% FBS/2 mM EDTA/PBS. Then, 1 µg/mL of propidium iodide was added thereto. After that, the mixture was made to pass through a tube with a 40-µm mesh filter. Finally, a Beckman Coulter-MoFlo XDP was used to analyze EpCAM-expressing cells.

Figure 12:
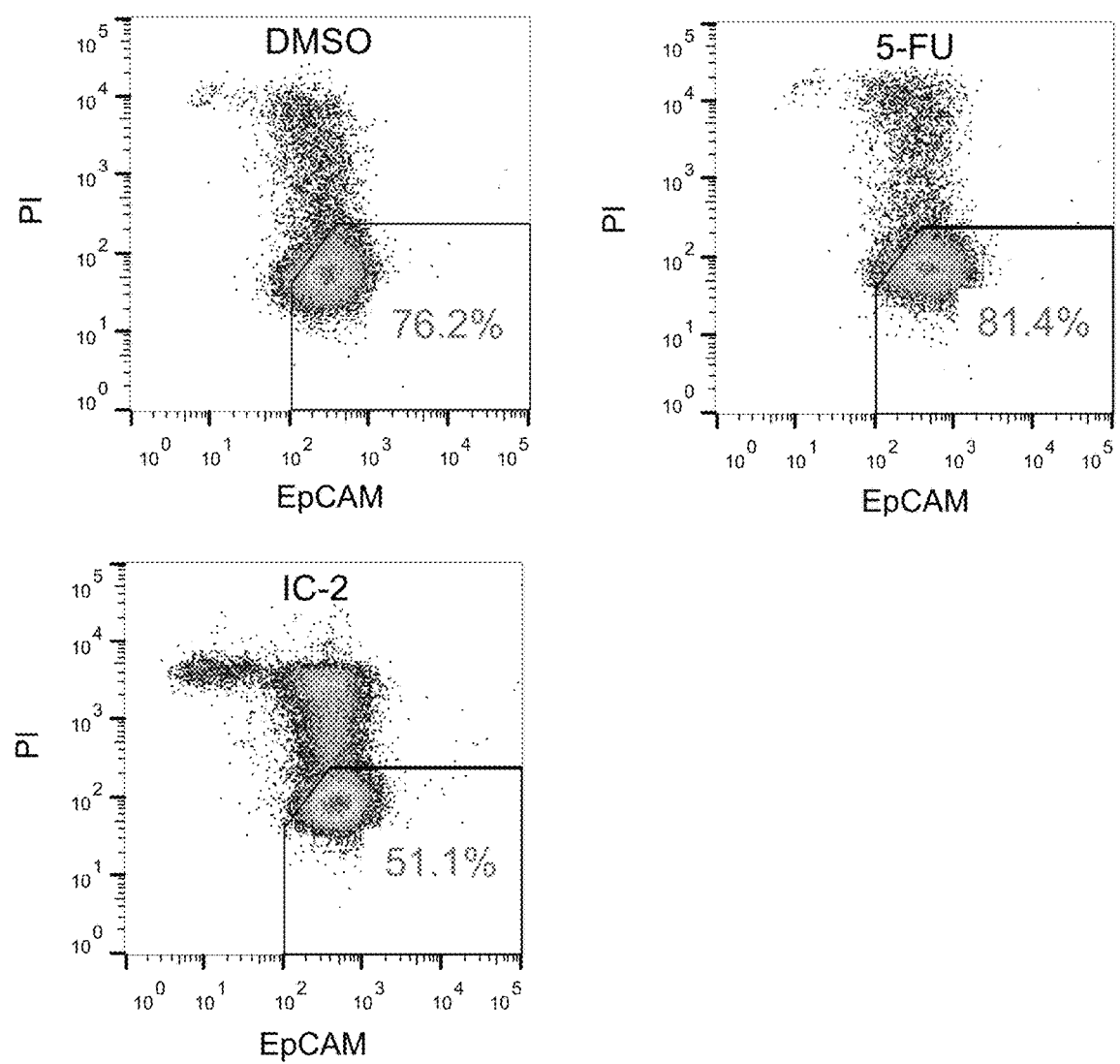
FIG. 12 is graphs showing the results of counting the number of EpCAM-positive cells after cancer stem cells were treated with low-molecular-weight compounds.

The results demonstrated that the proportion of the EpCAM-expressing cells was 76.2% for DMSO, 81.4% for 5-FU, and 51.1% for IC-2 (FIG. 12). That is, IC-2 exerted a superior inhibitory effect on liver cancer stem cells.

<Example 5> Evaluating Inhibitory Effect on Wnt/β-catenin Signaling Pathway

5.1 Establishment of Cell Line Stably Expressing CF4-CMVpro-Luc

First, 30 µg of a pTCF4-CMVpro-Luc was added to $5 \times 10^6$ HuH7 cells and the plasmid was introduced using a Cellject Pro (Thermo, Massachusetts, USA) (at 250 V, 1500 µF). Twenty-four hours after the gene introduction, 2 µg/mL of puromycin was added. Then, the cells were selected while a medium was changed every 3 to 5 days. It was observed that colonies of the pTCF4-CMVpro-Luc-containing HuH7 cells were formed at 20 days after initiation of the selection. A cloning ring, which was manufactured such that an end portion of a blue tip was cut, (the bottom edge of the cloning ring was provided with vaseline), was then used to surround one of the colonies formed. Subsequently, 30 µL of a 0.25% Trypsin/1 mM EDTA solution, which was prepared by diluting a stock solution 5-fold with PBS, was added to detach and collect the cells. After that, 70 µL of DMEM was added and the mixture was plated on a 96-well plate.

Next, the HuH7 cells at 70 to 90% confluency were collected, and the $3.5 \times 10^5$ cells were seeded in each well of a 24-well plate (FALCON). After 24 hours, the cells were collected into a 15-mL tube, centrifuged at 1000 rpm and room temperature for 5 min, washed with 1 mL of 1×PBS (−), and re-centrifuged at 1000 rpm and room temperature for 5 min. The cell mass was resuspended in 375 µL of a Proteinase K buffer. Then, 25 µL of sodium dodecyl sulfate (SDS) and 4 µL of Proteinase K (20 mg/mL) were added thereto. After that, the mixture was incubated overnight at 55° C. to degrade cellular proteins. Next, 400 mL of phenol/chloroform was added, and the mixture was vortexed and then centrifuged at 15000 rpm and 4° C. for 5 min to recover a supernatant. Subsequently, a 2-fold volume of 100% ethanol was added to the supernatant and the mixture was incubated at −80° C. for 30 min. After the sample was centrifuged at 15000 rpm and 4° C. for 20 min, a supernatant was discarded and 500 µL of 70% ethanol was added. The sample was further centrifuged at 15000 rpm and 4° C. for 10 min. Finally, a supernatant was discarded and 20 µL of ultra-pure water was used to dissolve the resulting pellet. One µL of the dissolved pellet was measured by using a spectrophotometer (LMS, Tokyo, Japan) to adjust the DNA content of the sample to 1 ng/µL. Next, a polymerase chain reaction (PCR) was carried out. Primers for a glyceraldehyde-3-phosphate dehydrogenase (GAPDH) locus were used as an internal control. Also, primers for a luciferase region were used.

A PCR was carried out by using rTaq (TOYOBO, Osaka, Japan) to amplify each gene at a 10-µL scale. For the GAPDH, the PCR consisted of: 95° C. for 2 min; 25 cycles (95° C. for 30 sec, 60° C. for 30 sec, and 72° C. for 30 sec); and 72° C. for 5 min. For the luciferase gene, the PCR consisted of: 95° C. for 2 min; 30 cycles (95° C. for 30 sec, 55° C. for 30 sec, and 72° C. for 30 sec); and 72° C. for 5 min.

Next, a luciferase assay was conducted. The HuH7 cells at 70 to 90% confluency were collected, and the $5 \times 10^4$ cells were seeded in each well of a 24-well plate (FALCON). Then, 100 µL of 20% Passive Lysis Buffer (PLB) (PROMEGA, Wisconsin, USA) was added to each well of the 24-well plate at 17 hours after the cell seeding. The plate was shaken at room temperature for 30 min. After that, 50 µL of Luciferase Assay Reagent (LAR) (PROMEGA) was added to each 3.5-ml Röhren tube (SARSTEDT, Numbrecht, German). Subsequently, 10 µL of the cell lysate prepared by using PLB in the 24-well plate was added to the tube, and the luciferase activity was measured by using a MiniLumat LB 9506 (Berthold Technologies, Bad Wildbad, German).

5.2 Luciferase Assay

First, the HuH7 cells that were at 70 to 90% confluency and stably expressed the pTCF4-CMVpro-Luc were collected, and the $1 \times 10^4$ cells were seeded in each well of a 96-well plate (FALCON). After 12 hours, the cells were treated with IC-2, PN3-13, or 5-FU at concentrations indicated in FIG. 13, and further incubated at 37° C. DMSO was used as a control. Two days after the low-molecular weight compound treatment, 100 µL of Steady-Glo (PROMEGA, Wisconsin, USA) was added to each well of a 96-well white plate (Corning Inc., New York, USA) and the mixture was incubated at room temperature for 5 min. Then, a fluorescence plate reader Infinite F500 (TECAN, Zurich, Switzerland) was used to measure luciferase activity.

Figure 13:
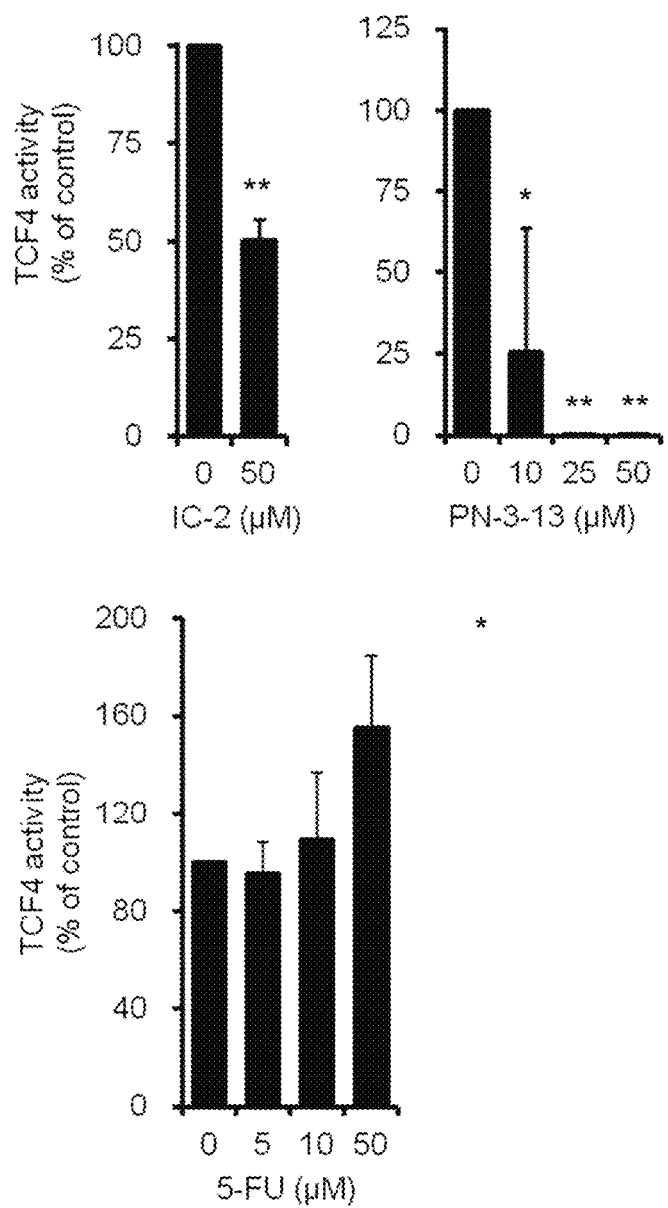
FIG. 13 is graphs showing the results of a luciferase assay.

The results demonstrated that IC-2 and PN-3-13 exerted an inhibitory effect on a Wnt/β-catenin signal (FIG. 13). However, 5-FU exerted no inhibitory effect on a Wnt/β-catenin signal.

<Example 6> Anti-Tumor Effect on Colon Cancer

6.1 Cell Culture

Colon cancer cells (DLD-1, HCT 116, colo 205) were cultured in a DMEM on a 10-cm cell culture dish (TPP Techno Plastic Products AG, Trasadingen, Switzerland) at 5% $CO_2$, 37° C., and a humidity of 100%. The cells at 70-90% confluency were split and washed with PBS (−). Next, 300 μL of Trypsin/EDTA was added to 2 mL of PBS (−) and the cells were incubated with this solution at 37° C. for 5 min to detach the cells. Then, 5 mL of DMEM was used to recover the cells. The recovered cells were centrifuged at 1000 rpm for 3 min to remove a supernatant. Then the cells were suspended in DMEM at 1:4 and subcultured.

6.2 Anti-Tumor Effect

First, $5 \times 10^5$ colon cancer cells (DLD-1, HCT 116, or colo 205) were seeded on a 96-well plate (TPP). After 24 hours, the cells were treated with IC-2, PN3-13, or HC-1 at concentrations indicated in FIGS. 14 to 16. Forty-eight hours after the low-molecular-weight compound treatment, 100 μL of 10% TetraColor ONE (SEIKAGAKU CORPORATION, Tokyo, Japan) was added and the mixture was then incubated at 37° C. After that, absorbance (at a measurement wavelength of 450 nm/a control wavelength of 600 nm) was measured by using a 96-well microplate reader (TECAN, Zurich, Switzerland).

Figure 14:
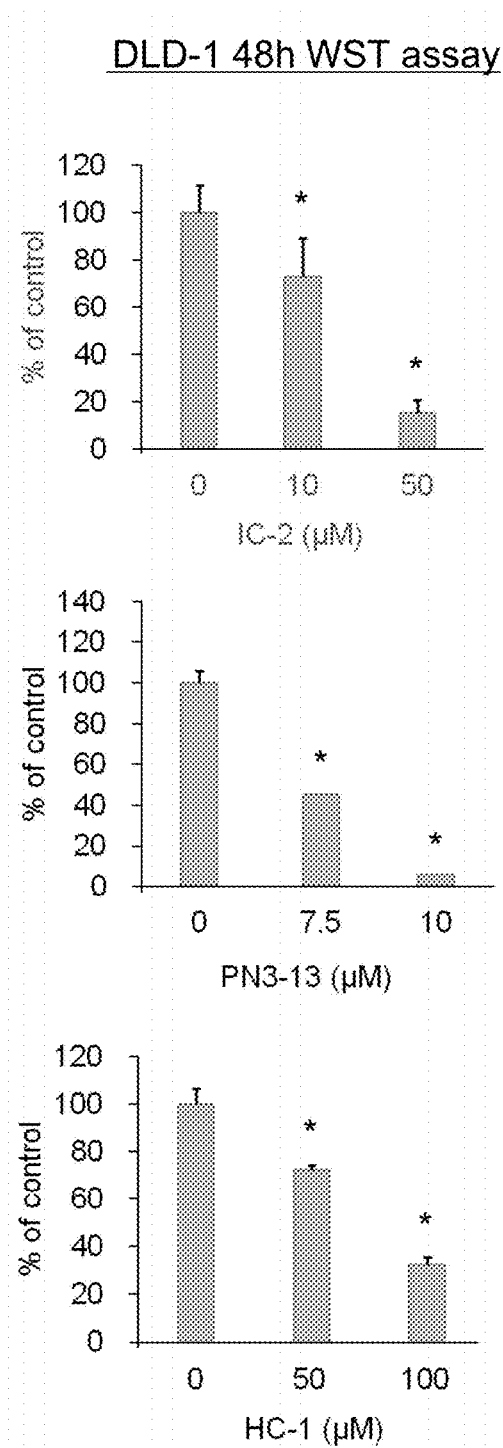
FIG. 14 is graphs showing the results of examining an anti-tumor effect on colon cancer.
Figure 15:
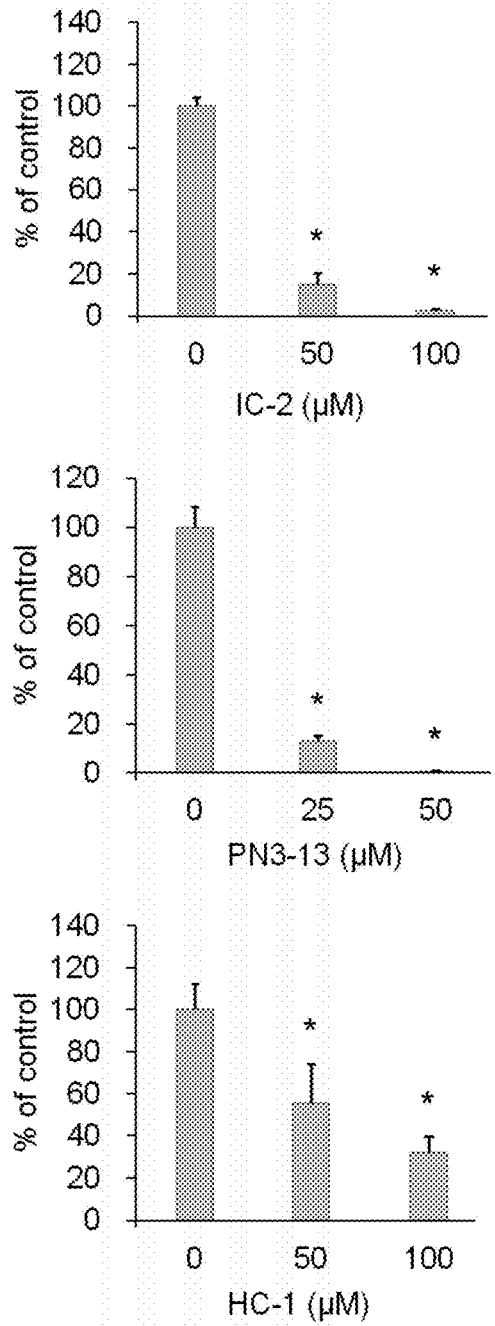
FIG. 15 is graphs showing the results of examining an anti-tumor effect on colon cancer.
Figure 16:
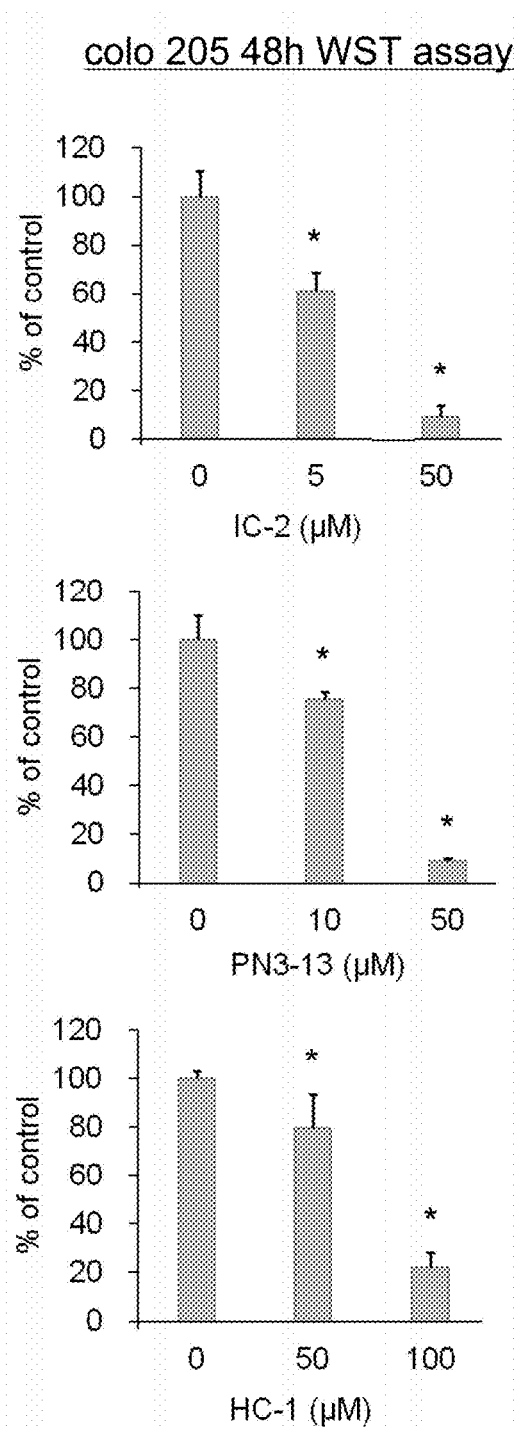
FIG. 16 is graphs showing the results of examining an anti-tumor effect on colon cancer.

The results demonstrated that IC-2, PN3-13, and HC-1 exerted an inhibitory effect on proliferation of the colon cancer cells (FIGS. 14 to 16).

6.3 Evaluation of Sphere Formation Capability

Expression of a cell surface marker CD44 was used as an index to sort DLD-1 cells into the top 5% group and the bottom 5% group. An anti-human CD44 antibody (Abcam Ltd., Cambridge, UK) was used as a primary antibody and an Alexa 488-labeled goat anti-mouse IgG antibody (Life Technologies Corp., Carlsbad, CA, USA) was then used. After that, a MoFlo XDP (Beckman Coulter Inc., Fullerton, CA) was used to analyze and fractionate each group. Next, the 5,000 collected cells were plated on each well of 24-well ultra-low-attachment multiwell plates (Corning Inc., Corning, NY) in 500 μl of a serum-free DMEM/F12 medium containing 20 ng/ml of recombinant human basic fibroblast growth factor (bFGF: Corefront Corporation, Tokyo, Japan), 20 ng/ml of recombinant human epidermal growth factor (Sigma Life Science, St. Louis, United States), B-27 (life technologies), 200 mmol/L of L-glutamine (Invitrogen, Life Technologies Corp., Carlsbad, CA), and 0.6% methyl cellulose (Sigma Life Science). Then, a difference in sphere formation capability was examined. On Day 3, 500 ml of the medium containing the above components was further added. On Day 7, the evaluation was conducted. A phase contrast microscope was used to take photos with respect to 10 visual fields per well. Next, free software Image J was used to count the total number of spheres. Then, the total number was compared between the groups.

Figure 17:
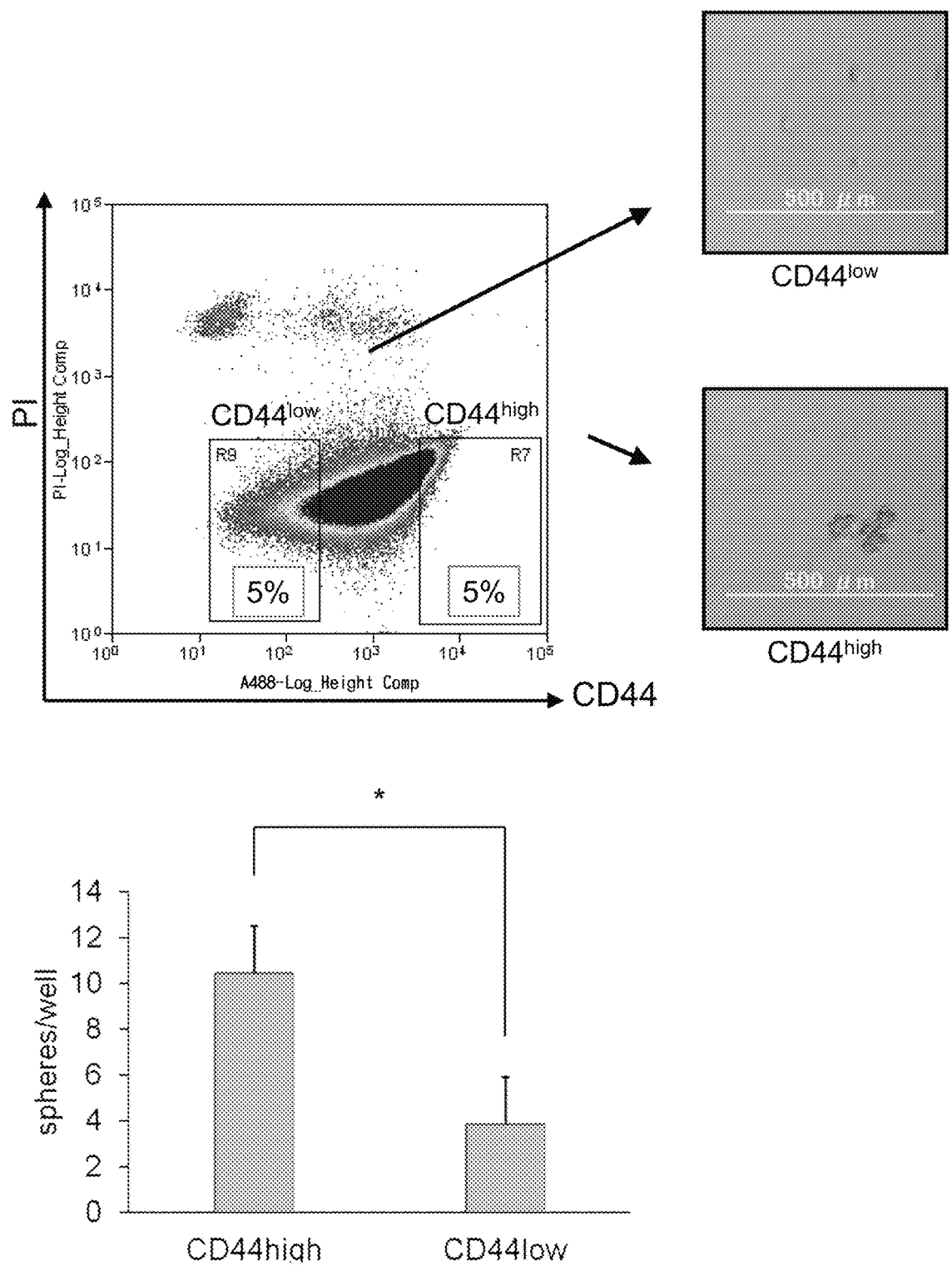
FIG. 17 contains a graph showing the results of testing the sphere formation capability of colon cancer cells.

With respect to DLD-1, the number of spheres formed per well in a cell population expressing CD44 more strongly is significantly higher than that in a cell population expressing CD44 weakly (FIG. 17). This demonstrated that the group expressing CD44 strongly contained a larger number of cells exhibiting sphere formation capability and having cancer stem cell characteristics.

6.4 Inhibitory Effect on Cancer Stem Cells

First, $1 \times 10^6$ DLD-1 cells were seeded on a 10-cm dish. After 24 hours, the cells were treated with 5-FU (0.5, 5 μM) or IC-2 (50 μM). After additional 48 hours, the cells were harvested. An anti-human CD44 antibody (Abcam Ltd., Cambridge, UK) was used as a primary antibody and an Alexa 488-labeled goat anti-mouse IgG antibody (Life Technologies Corp., Carlsbad, CA, USA) was then used. After that, analysis was performed by using a MoFlo XDP (Beckman Coulter Inc., Fullerton, CA).

Figure 18:
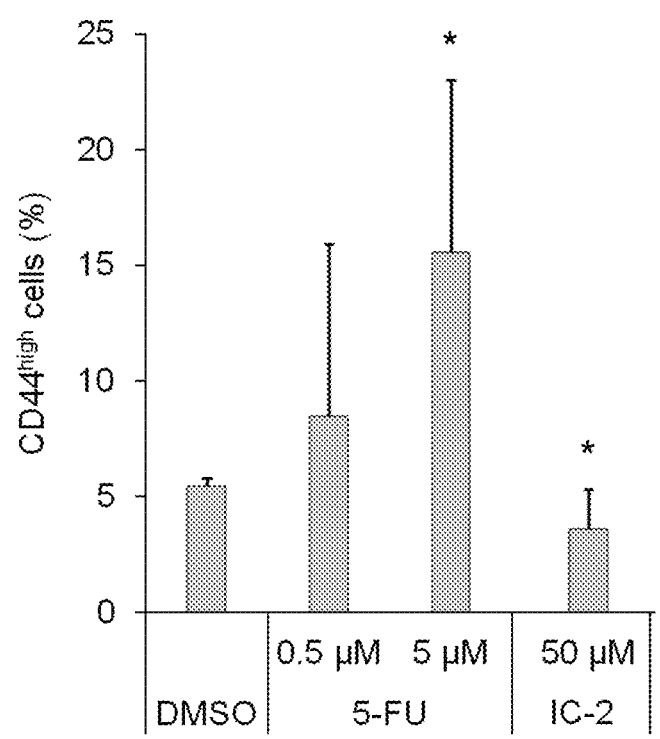
FIG. 18 is a graph showing the results of examining an inhibitory effect on cancer stem cells in colon cancer.

The results demonstrated that the IC-2 treatment significantly decreased the proportion of CD44high cells (cells expressing CD44 strongly) over a control (FIG. 18). That is, IC-2 exerted an inhibitory effect on cancer stem cells. Note that 5-FU rather increased the proportion of the CD44high cells.

6.5 Inhibitory Effect on Wnt/β-catenin Signal

First, $3.34 \times 10^4$ colon cancer cells (DLD-1, HCT 116, or colo 205) were seeded on each well of a 24-well plate. After 24 hours, transfection was carried out by using 1 μL of lipofectamine 2000 (Invitrogen, Life Technologies Corp., Carlsbad, CA), 50 ng of pTCF4-CMVpro-FLuc, and 2.5 ng of pCMVpro-Rluc. After 4 hours, the cells were treated with IC-2, PN3-13, or HC-1 at concentrations indicated in FIGS. 19 to 21. After 48 hours from the low-molecular-weight compound treatment, 100 μL of 20% Passive Lysis Buffer (PROMEGA, Wisconsin, USA) was added to each well of a 24-well plate. The plate was shaken at ordinary temperature for 15 min and was then allowed to stand overnight at −30° C. On the following day, a Dual-Luciferase (a registered trademark) Reporter Assay System (PROMEGA) was used, and luciferase activity was then measured by using a Mini-Lumat LB 9506 (Berthold Technologies, Bad Wildbad, German).

Figure 19:
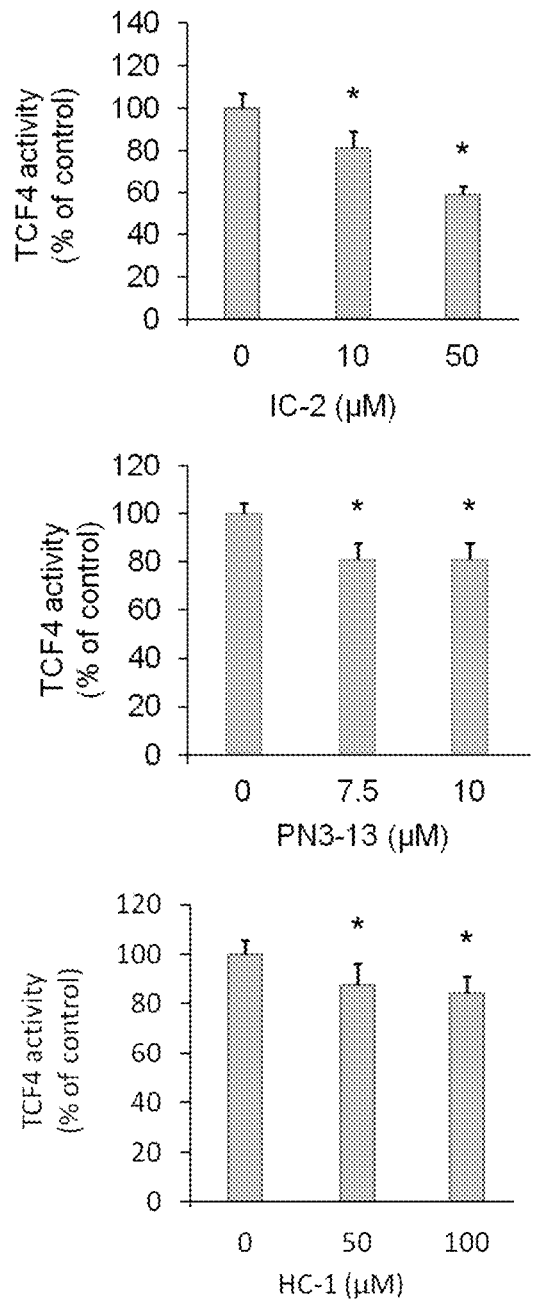
FIG. 19 is graphs showing the results of examining an inhibitory effect on a Wnt/β-catenin signal in colon cancer.

The results demonstrated that IC-2, PN3-13, and HC-1 exerted an inhibitory effect on a Wnt/β-catenin signal in the colon cancer cells (FIGS. 19 to 21).

<Example 7> Anti-Tumor Effect on Squamous Cell Carcinoma

7.1 Cell Culture

HSC2 cells (a squamous cell carcinoma cell line) were cultured in a DMEM on a 10-cm cell culture dish (TPP Techno Plastic Products AG, Trasadingen, Switzerland) at 5% $CO_2$, 37° C., and a humidity of 100%. The cells at 70-90% confluency were to be split and washed with PBS (−). Next, 300 μL of Trypsin/EDTA was added to 2 mL of PBS (−) and the cells were incubated with this solution at 37° C. for 5 min to detach the cells. Then, 5 mL of DMEM was used to recover the cells. The recovered cells were centrifuged at 1000 rpm for 3 min to remove a supernatant. The pelleted cells were suspended in DMEM and subcultured at 1:4.

7.2 Anti-Tumor Effect

Figure 22:
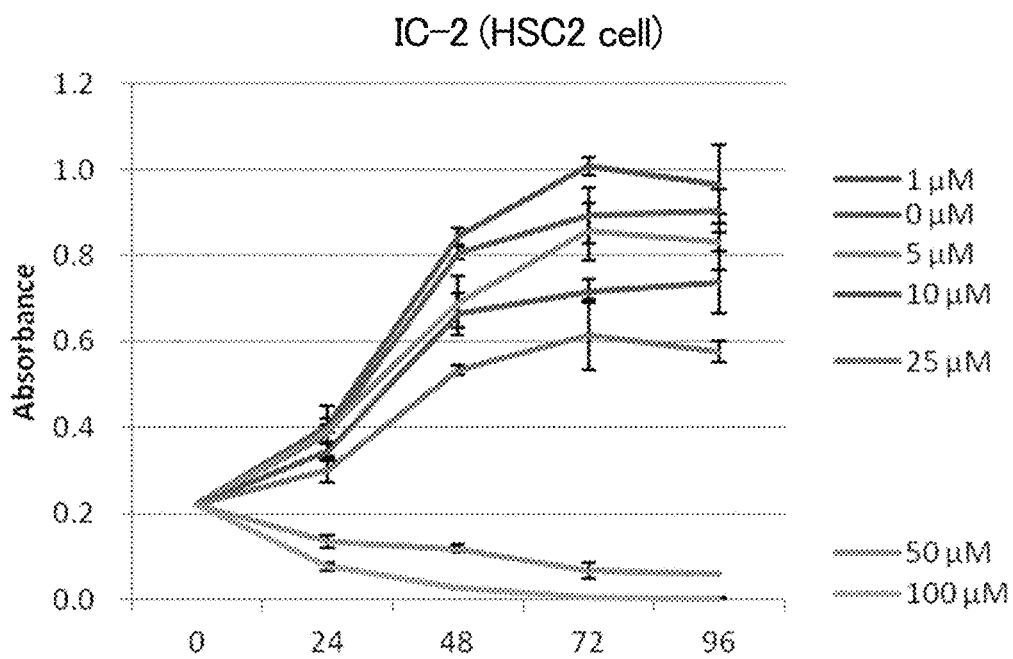
FIG. 22 is a graph showing the results of examining an anti-tumor effect on squamous cell carcinoma.
Figure 23:
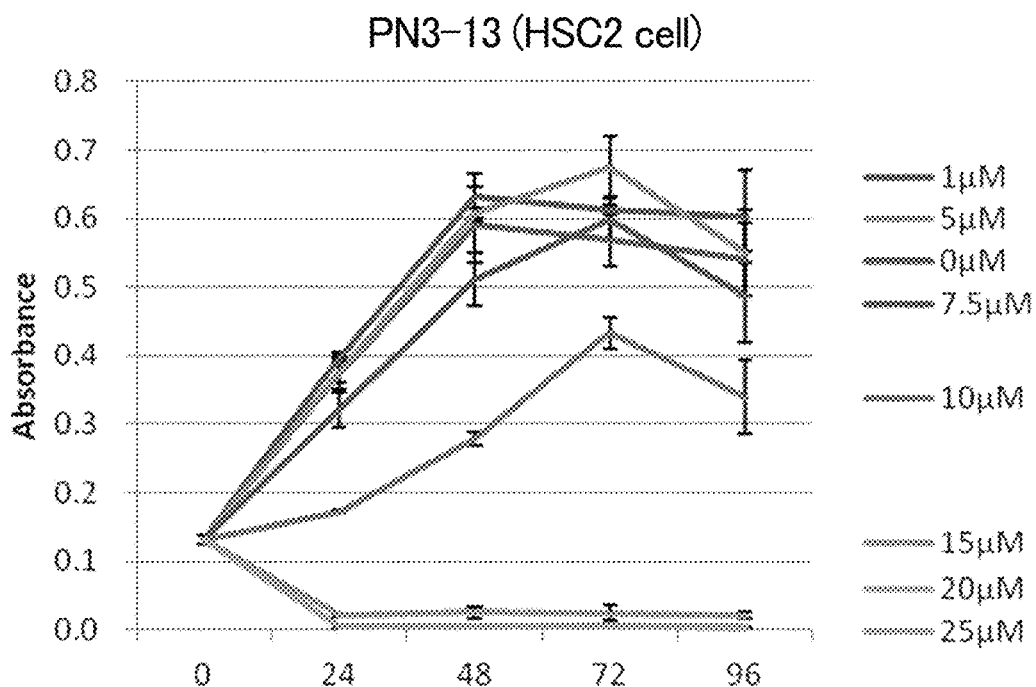
FIG. 23 is a graph showing the results of examining an anti-tumor effect on squamous cell carcinoma.
Figure 24:
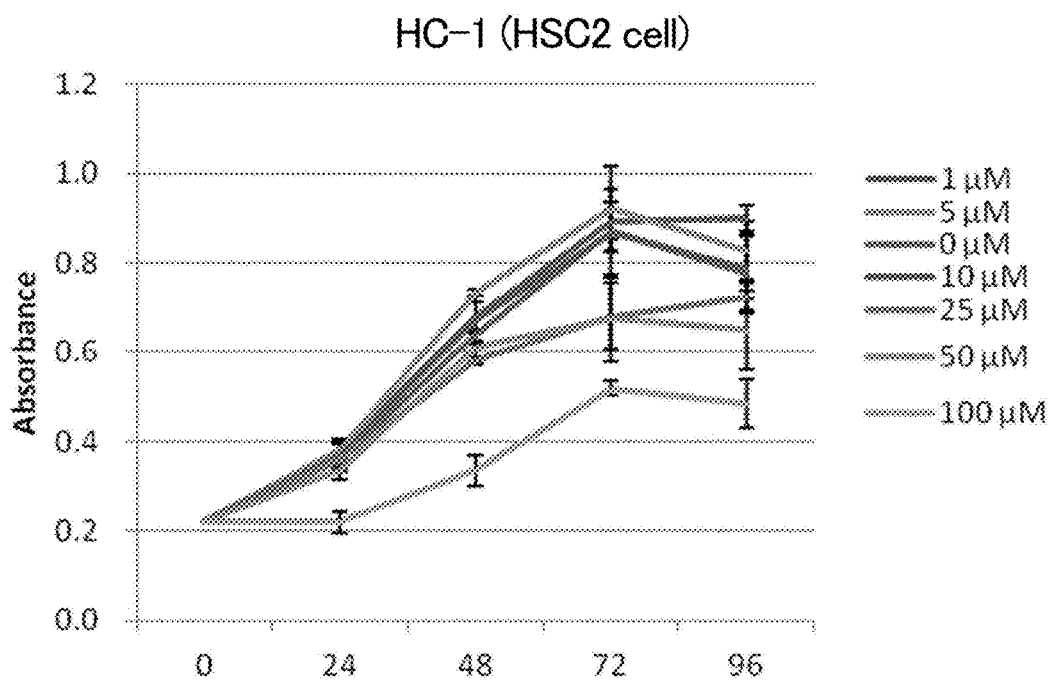
FIG. 24 is a graph showing the results of examining an anti-tumor effect on squamous cell carcinoma.
Figure 25:
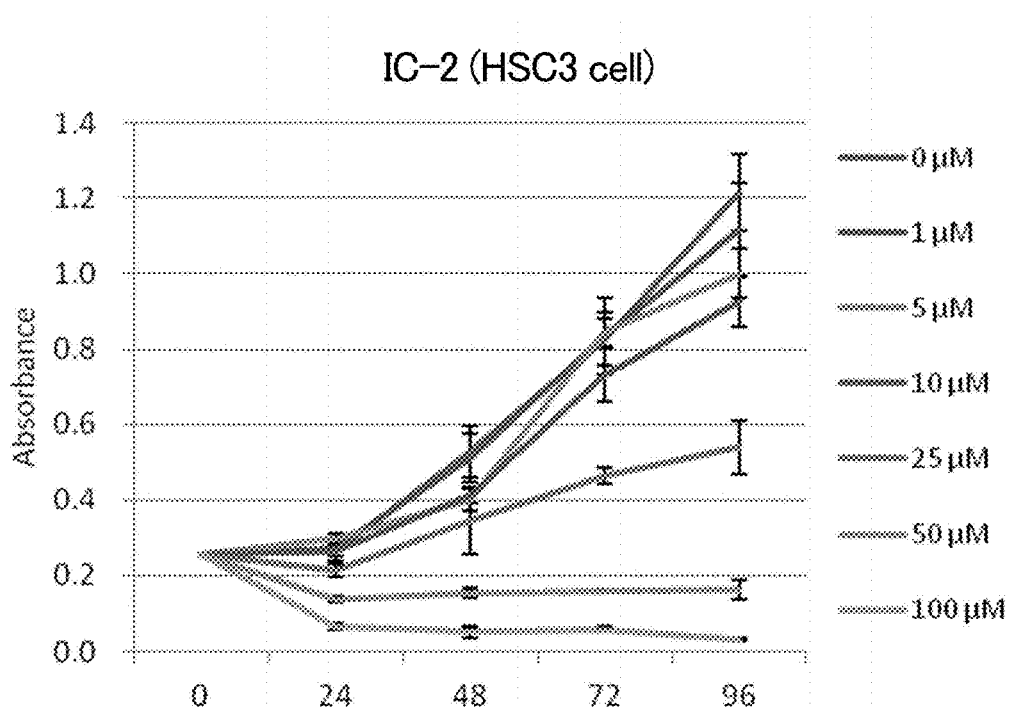
FIG. 25 is a graph showing the results of examining an anti-tumor effect on squamous cell carcinoma.

First, $2.5 \times 10^3$ of HSC2 cells were seeded on each well of a 96-well plate (TPP). After 24 hours, the cells were treated with IC-2, PN3-13, or HC-1 at concentrations and durations indicated in FIGS. 22 to 24. After 48 hours from the low-molecular-weight compound treatment, 100 μL of 10% TetraColor ONE (SEIKAGAKU CORPORATION, Tokyo, Japan) was added and the mixture was then incubated at 37° C. After that, absorbance (at a measurement wavelength of 450 nm/a control wavelength of 600 nm) was measured by a 96-well microplate reader (TECAN, Zurich, Switzerland).

The same procedure was used to investigate an anti-tumor effect of IC-2 on a squamous cell carcinoma cell line HSC3 after culturing.

The results demonstrated that IC-2, PN3-13, and HC-1 exerted inhibitory effects on proliferation of the squamous cell carcinoma cells (FIGS. 22 to 25).

7.3 Inhibitory Effect on Cancer Stem Cells

First, $5 \times 10^5$ of HSC2 cells were plated on a 10-cm dish. After 24 hours, the cells were treated with 5-FU (0.5 µM), IC-2 (25 µM), PN-3-13 (7.5 µM), or HC-1 (50 µM). Also, some of the cells were prepared without low-molecular-weight compound treatment (0 µM). After additional 48 hours, the cells were harvested. An anti-human CD44 antibody (Abcam Ltd., Cambridge, UK) was used as a primary antibody and an Alexa 488-labeled goat anti-mouse IgG antibody (Life Technologies Corp., Carlsbad, CA, USA) was then used. After that, analysis was performed by using a cell sorter, BD bioscience FACS Aria (BD Biosciences, CA, USA). Note that the concentration of each low-molecular-weight compound was determined on the basis of the $IC_{50}$ concentration at 48 hours in a WST assay.

Figure 26:
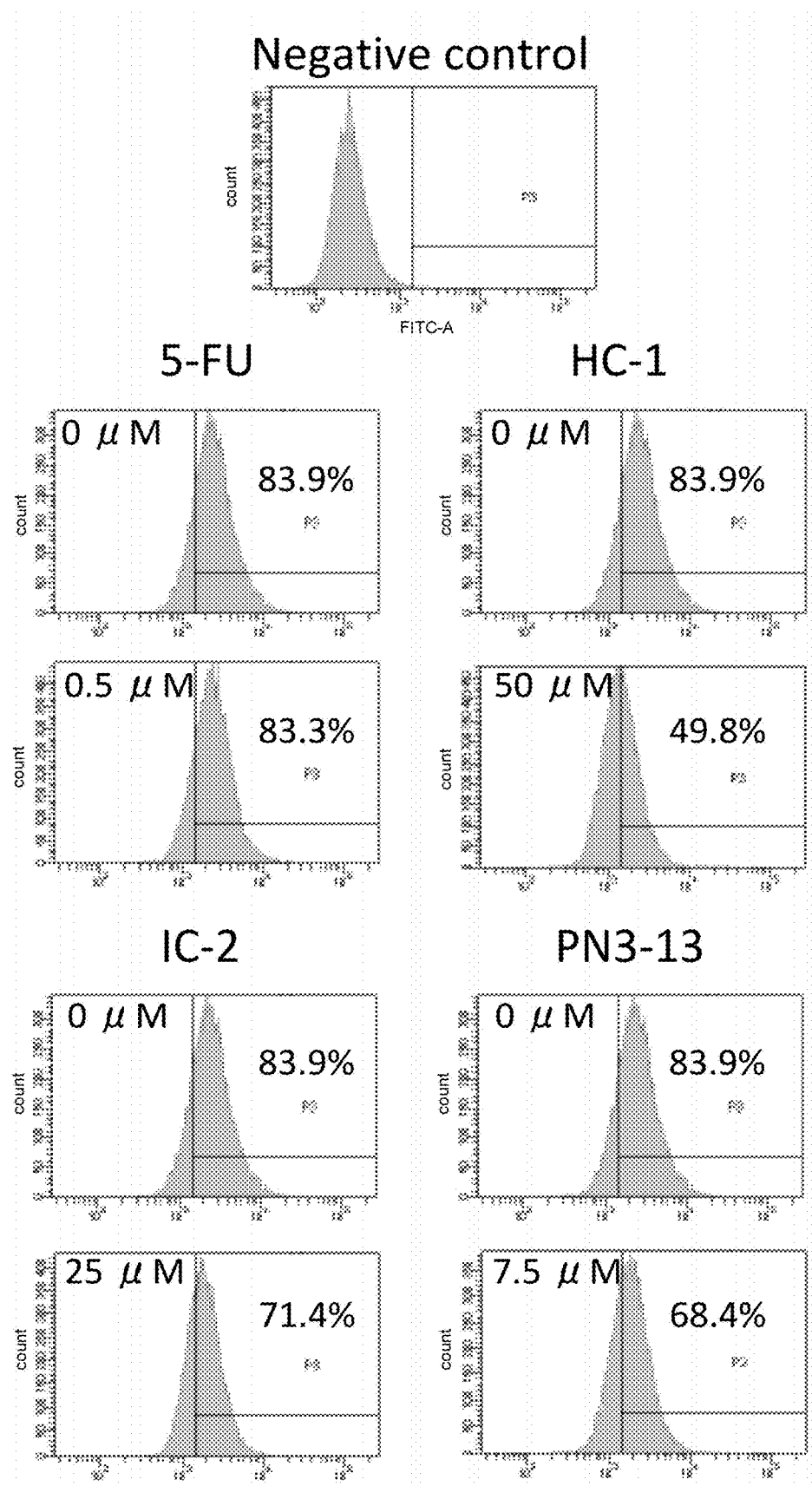
FIG. 26 is histograms showing the results of examining an inhibitory effect on cancer stem cells in squamous cell carcinoma.

The results demonstrated that the proportion of CD44-expressing cells was 83.9% in the case of no low-molecular-weight compound treatment; the proportion was decreased to 71.4% in the case of IC-2 treatment; the proportion was decreased to 68.4% in the case of PN-3-13 treatment; and the proportion was decreased to 49.8% in the case of HC-1 treatment (FIG. 26). That is, IC-2, PN3-13, and HC-1 exerted an inhibitory effect on cancer stem cells. Among them, the effect of HC-1 was remarkable. Note that in the case of 5-FU the proportion was 83.3% and little change was observed.

7.4 Inhibitory Effect on Wnt/β-Catenin Signal

First, $5 \times 10^4$ of HSC2 cells were seeded on each well of a 24-well plate. After 24 hours, transfection was carried out by using 1 µL of lipofectamine 2000 (Invitrogen, Life Technologies Corp., Carlsbad, CA), 50 ng of pTCF4-CMVpro-FLuc, and 2.5 ng of pCMVpro-Rluc. After 4 hours, the cells were treated with IC-2, PN3-13, or HC-1 at concentrations indicated in FIGS. 27 to 29. After 48 hours from the low-molecular-weight compound treatment, 100 µL of 20% Passive Lysis Buffer (PROMEGA, Wisconsin, USA) was added to each well of the 24-well plate. The plate was shaken at ordinary temperature for 15 min and was then allowed to stand overnight at −30° C. On the following day, a Dual-Luciferase (a registered trademark) Reporter Assay System (PROMEGA) was used, and luciferase activity was then measured by using a MiniLumat LB 9506 (Berthold Technologies, Bad Wildbad, German).

Figure 27:
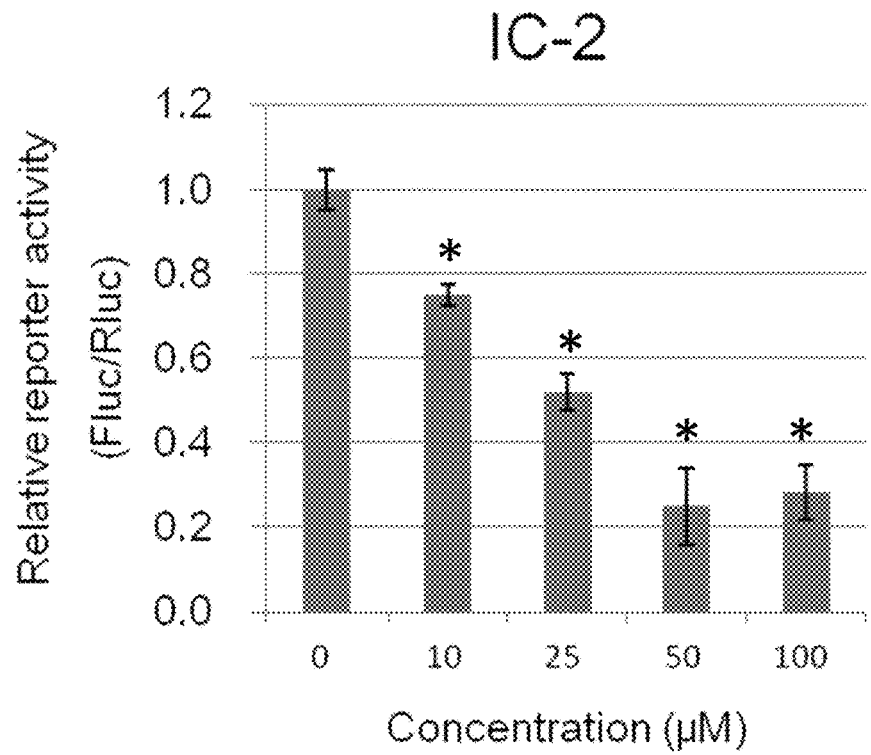
FIG. 27 is a graph showing the results of examining an inhibitory effect on a Wnt/β-catenin signal in colon cancer.
Figure 28:
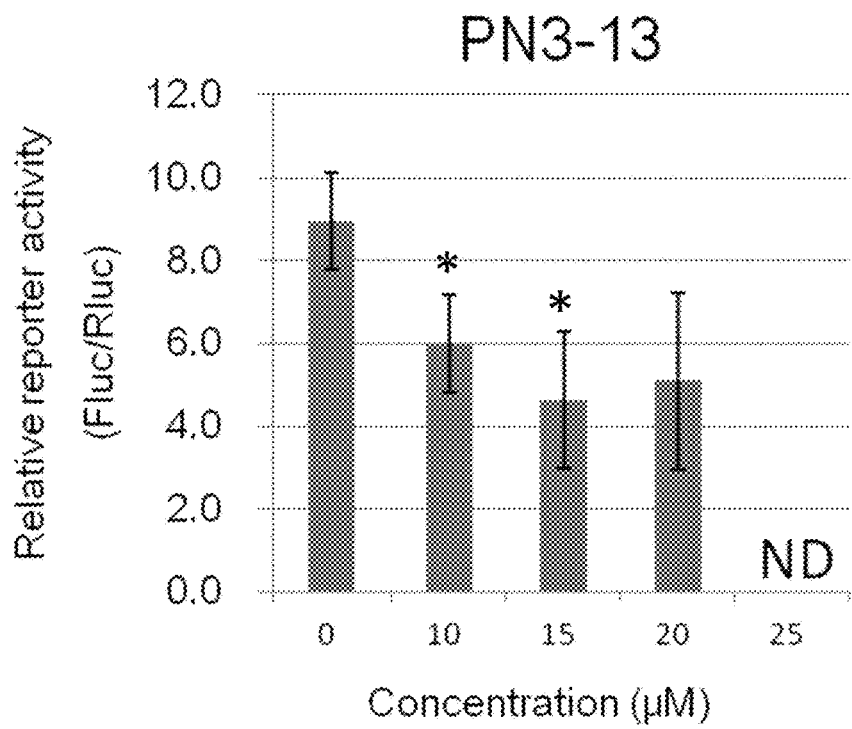
FIG. 28 is a graph showing the results of examining an inhibitory effect on a Wnt/β-catenin signal in colon cancer.
Figure 29:
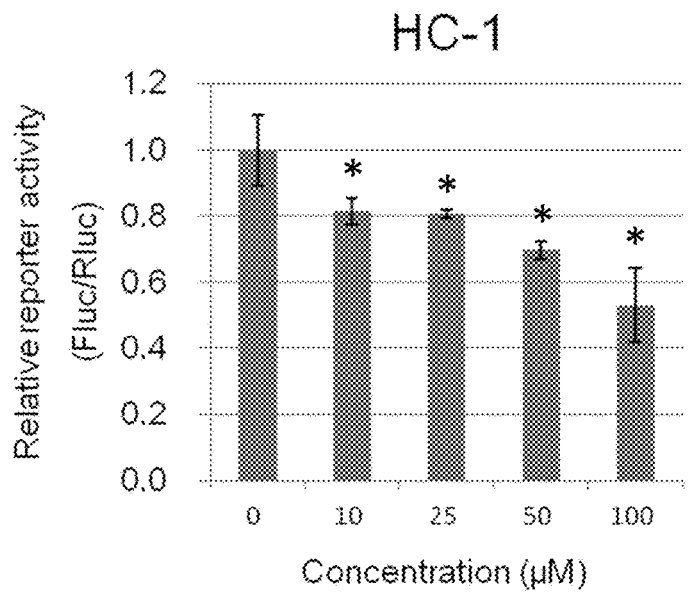
FIG. 29 is a graph showing the results of examining an inhibitory effect on a Wnt/β-catenin signal in colon cancer.
Figure 30:
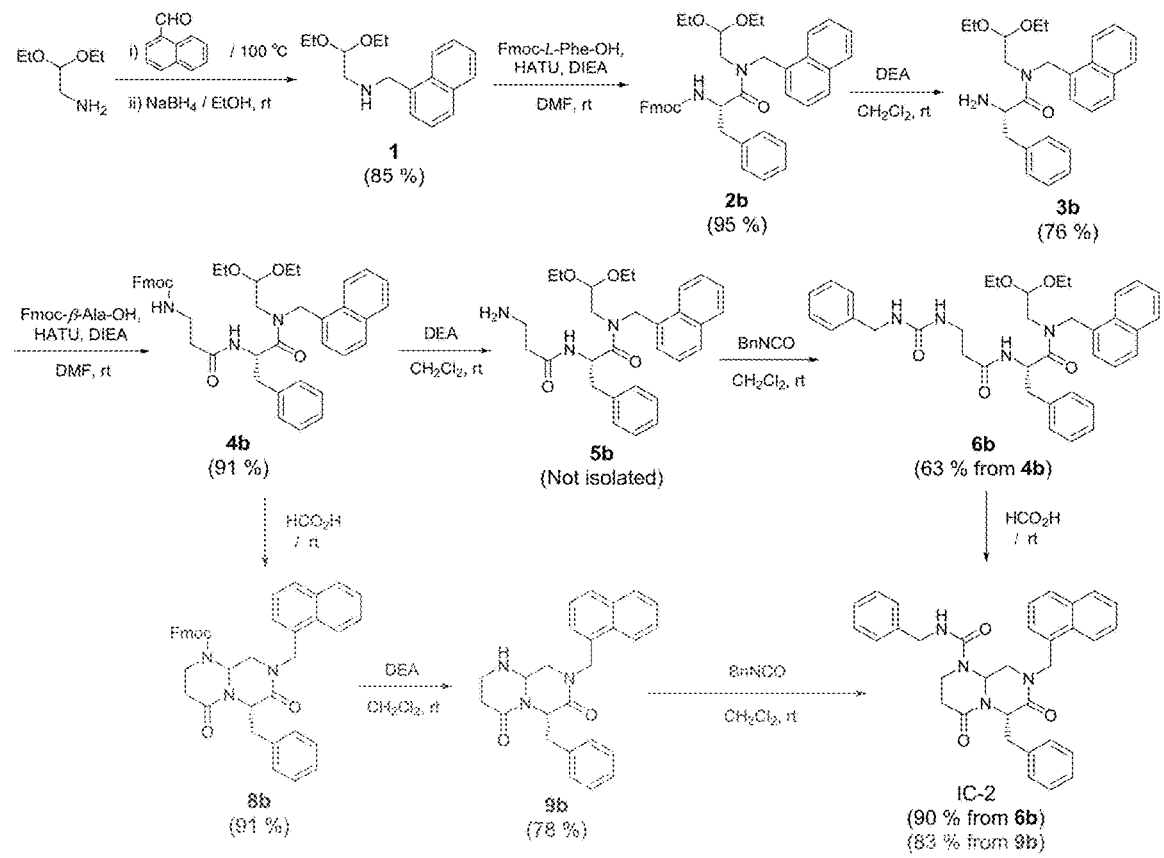
FIG. 30 is a diagram illustrating a synthetic scheme of an IC-2 derivative according to Example 8.

The results demonstrated that IC-2, PN3-13, and HC-1 exerted an inhibitory effect on a Wnt/β-catenin signal in the squamous cell carcinoma cells (FIGS. 27 to 29).

<Example 8> Evaluation of IC-2 Derivatives

8.1 Synthesis

IC-2 derivatives were synthesized in accordance with the schemes designated in FIGS. 30 to 35. The details of the synthesis were illustrated below. FIGS. 36 and 37 show the structures and spectral data of the IC-2 derivatives synthesized.

Compound 1

First, 1-naphtaldehyde (1.6 g, 10 mmol) and 2,2-dietoxy-ethanamine (1.3 g, 10 mmol) were mixed, and the mixture was stirred at 100° C. for from 30 min to 1 h. After allowed to cool, the reaction mixture was mixed with EtOH (25 mL), and the resulting mixture was stirred and made homogeneous. Next, a small amount of $NaBH_4$ (0.38 g, 10 mmol) was gradually added and the mixture was then stirred at room temperature for from 1 h to overnight. After completion of the reaction, EtOH was distilled away while the mixture was concentrated under reduced pressure. (An appropriate amount of) Water was added to the resulting residue, and a product was extracted with AcOEt. A separated organic layer was washed with saturated saline and dried with $Na_2SO_4$. After that, the sample was filtered and concentrated under reduced pressure. The resulting residue was purified by silica gel column chromatography (AcOEt/hexane=5/1) to yield compound 1 (2.3 g, 8.5 mmol, 85%) as colorless transparent liquid.

Compound 2b

HATU (0.76 g, 2.0 mmol) and diisopropylethylamine (DIEA) (0.26 g, 2.0 mmol) were added to a dry-DMF solution (7 mL) containing Fmoc-L-Phe-OH (0.54 g, 2.0 mmol), and the mixture was stirred at room temperature for 30 min. The compound 1 (0.54 g, 2.0 mmol) was added to the reaction mixture and then stirred overnight at room temperature. After completion of the reaction, water (20 mL) was added. Then, a product was extracted with AcOEt. A separated organic layer was washed twice with saturated saline and dried with $Na_2SO_4$. After that, the sample was filtered and concentrated under reduced pressure. The resulting residue was purified by silica gel column chromatography (AcOEt/hexane=½) to yield compound 2b (1.2 g, 1.9 mmol, 95%) as a colorless solid.

Compound 3b

Diethylamine (DEA) (10 mL) was added to a $CH_2Cl_2$ solution (20 mL) containing the compound 2b (1.1 g, 1.7 mmol), and the mixture was stirred at room temperature for 3 h. After completion of the reaction, $CH_2Cl_2$ and excessive DEA were distilled away while the mixture was concentrated under reduced pressure. The resulting residue was purified by silica gel column chromatography (AcOEt/EtOH=5/1) to yield compound 3b (0.55 g, 1.3 mmol, 76%) as colorless, transparent, viscous liquid.

Compound 4b

HATU (3.3 g, 8.7 mmol) and DIEA (1.1 g, 8.5 mmol) were added to a dry-DMF solution (15 mL) containing Fmoc-β-Ala-OH (2.5 g, 8.0 mmol), and the mixture was stirred at room temperature for 30 min. The compound 3b (3.3 g, 7.8 mmol) was added to the reaction mixture and then stirred overnight at room temperature. After completion of the reaction, water (30 mL) was added. Then, a product was extracted with AcOEt. A separated organic layer was washed twice with saturated saline and dried with $Na_2SO_4$. After that, the sample was filtered and concentrated under reduced pressure. The resulting residue was purified by silica gel column chromatography (AcOEt/hexane=3/1) to yield compound 4b (5.1 g, 7.1 mmol, 91%) as a colorless solid.

Compound 6b

DEA (6 mL) was added to a $CH_2Cl_2$ solution (10 mL) containing the compound 4b (2.8 g, 3.9 mmol), and the mixture was stirred at room temperature for from 3 to 4 h. $CH_2Cl_2$ and excessive DEA were distilled away while the mixture was concentrated under reduced pressure. (An appropriate amount of) $CH_2Cl_2$ was added to the resulting residue and the mixture was made a homogeneous solution. After that, the sample was again concentrated under reduced pressure. After this procedure was repeated twice, $CH_2Cl_2$ (10 mL) was added to the resulting residue. The mixture was stirred and made homogeneous. Then, benzyl isocyanate (0.78 g, 5.9 mmol) was added and the resulting mixture was stirred overnight at room temperature. After completion of the reaction, $CH_2Cl_2$ was distilled away while the mixture was concentrated under reduced pressure. The resulting residue was purified by silica gel column chromatography (AcOEt/EtOH=30/1) to yield compound 6b (1.5 g, 2.4 mmol, 62%) as a colorless solid.

Compound 6b-R

Figure 31:
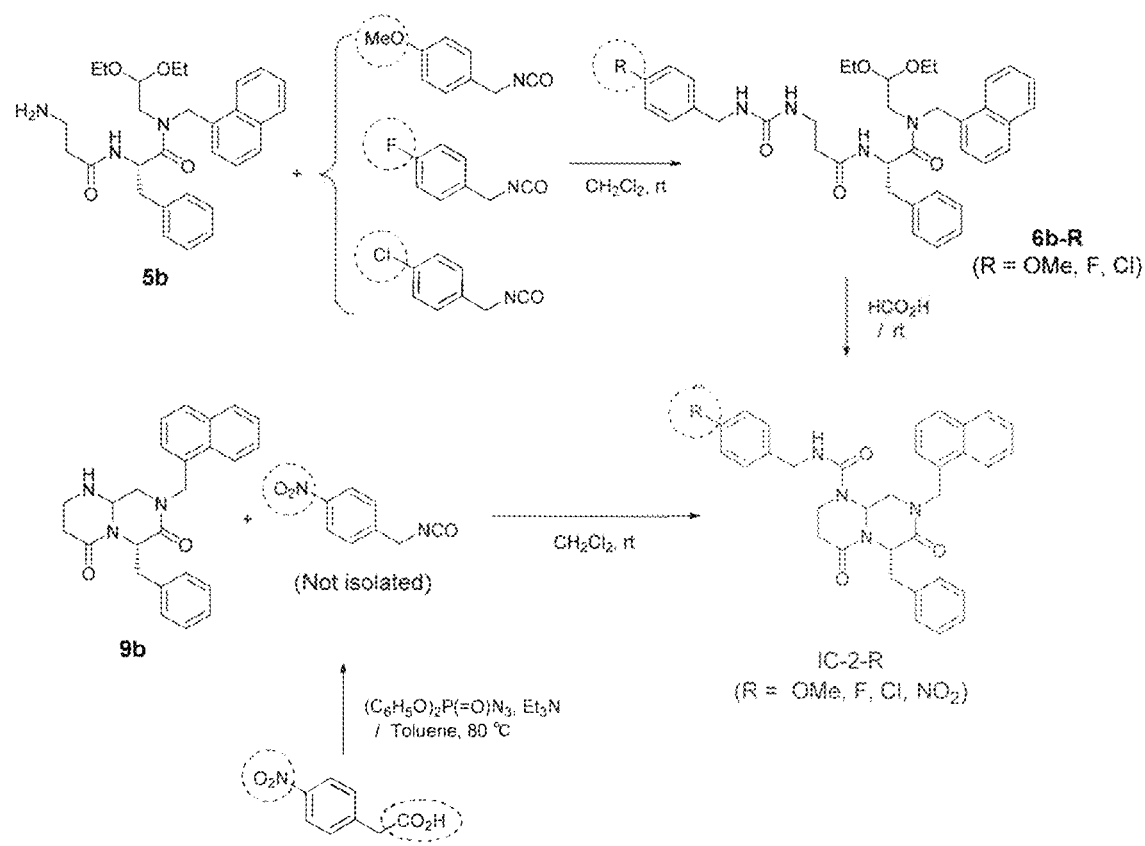
FIG. 31 is a diagram illustrating a synthetic scheme of an IC-2 derivative according to Example 8.
Figure 32:
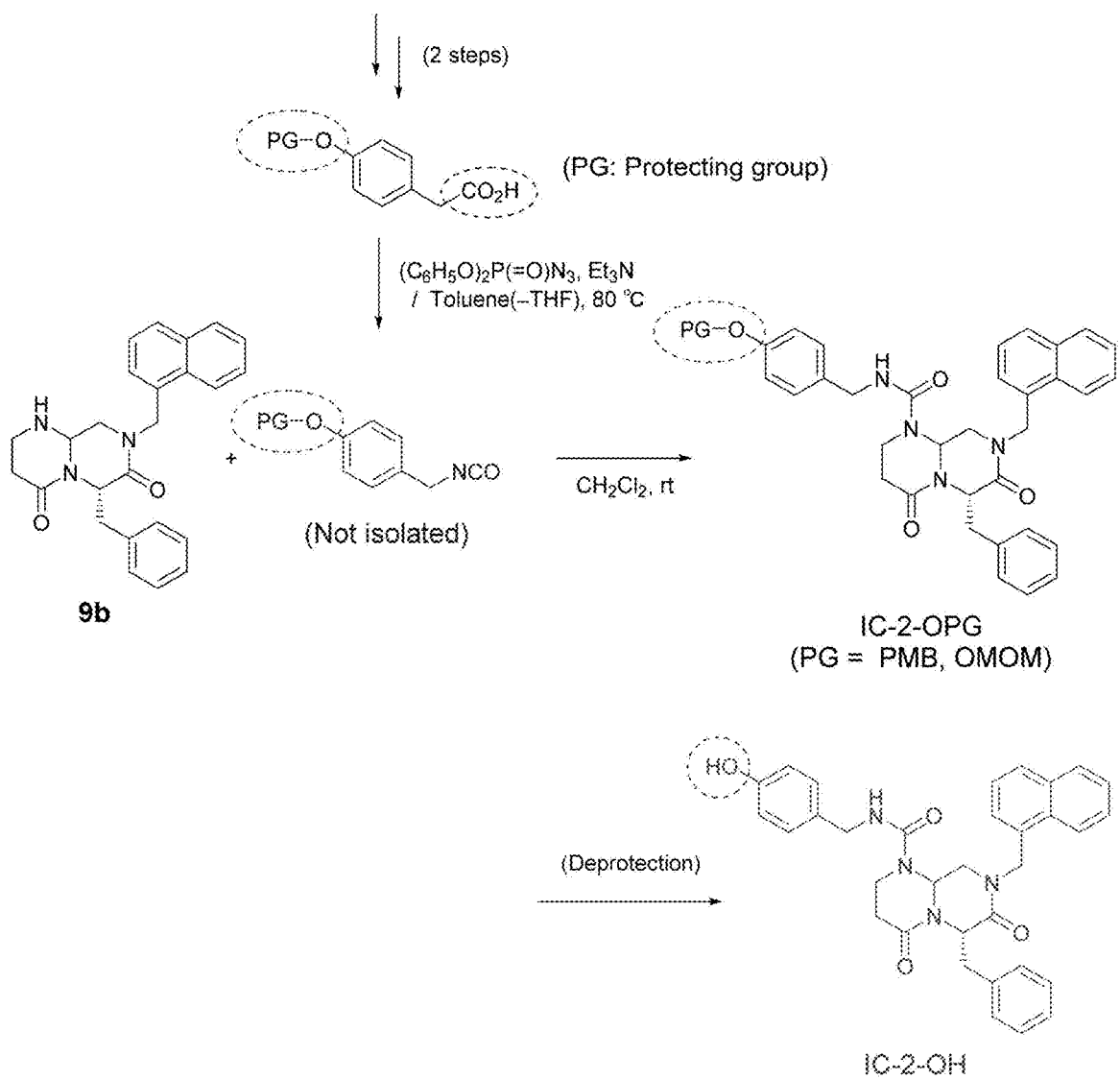
FIG. 32 is a diagram illustrating a synthetic scheme of an IC-2 derivative according to Example 8.
Figure 33:
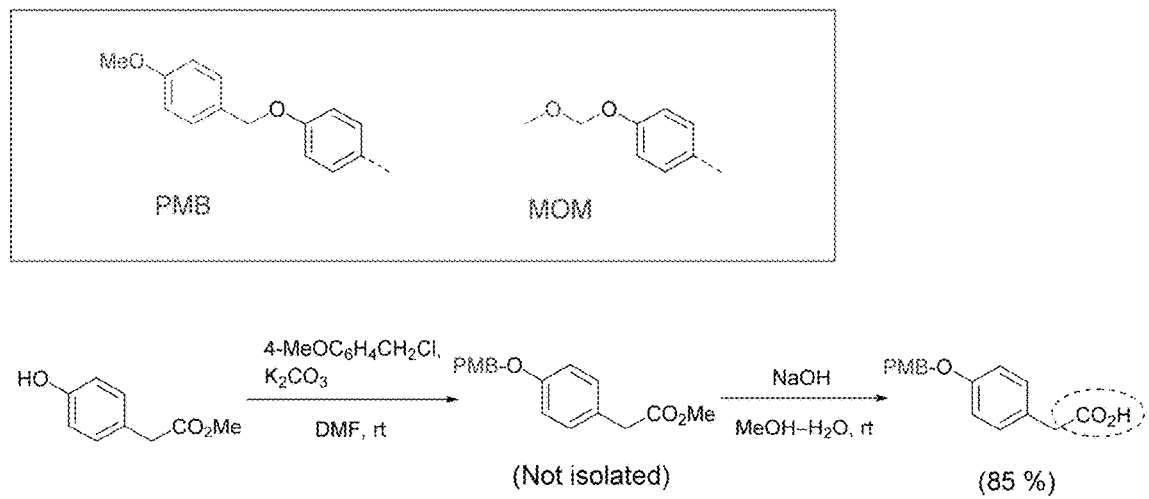
FIG. 33 is a diagram illustrating a synthetic scheme of IC-2 derivatives according to Example 8.
Figure 34:
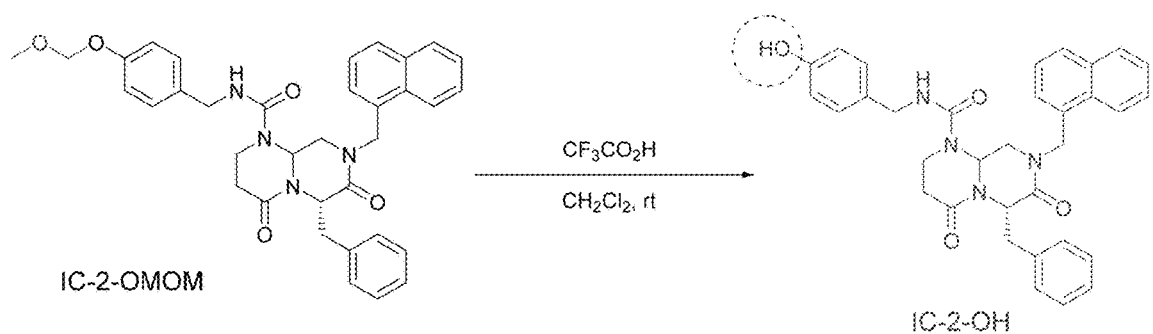
FIG. 34 is a diagram illustrating a synthetic scheme of an IC-2 derivative according to Example 8.
Figure 35:
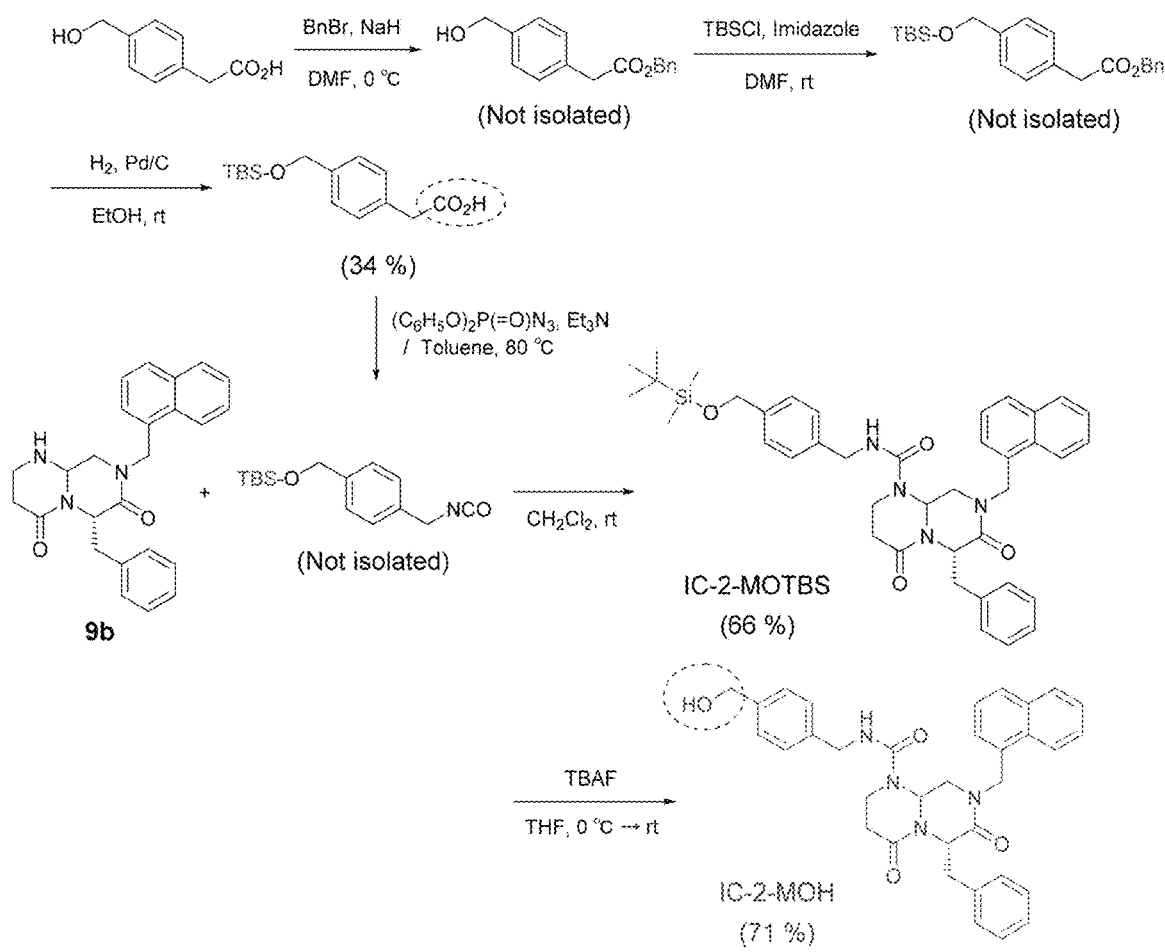
FIG. 35 is a diagram illustrating a synthetic scheme of an IC-2 derivative according to Example 8.

Compound 6b-R (a substituent R=OMe, Cl, or F) was synthesized in accordance with the scheme designated in FIG. 31.

Compound 8b

Formic acid (10 mL) was added to the compound 4b (1.6 g, 2.3 mmol), and the mixture was stirred overnight at room temperature. After completion of the reaction, formic acid was distilled away while the mixture was concentrated under reduced pressure. The resulting residue was purified by silica gel column chromatography (AcOEt/hexane=4/1) to yield compound 8b (1.3 g, 2.1 mmol, 91%) as a colorless solid.

Compound 9b

Diethylamine (1.3 g, 18 mmol, 1.8 mL) was added to a $CH_2Cl_2$ solution (5.5 mL) containing the compound 8b (1.1 g, 1.8 mmol), and the mixture was stirred at room temperature for 3 h. After completion of the reaction, $CH_2Cl_2$ was distilled away while the mixture was concentrated under reduced pressure. The resulting residue was purified by silica gel column chromatography (AcOEt/EtOH=7/1) to yield compound 9b (0.57 g, 1.4 mmol, 78%) as a colorless solid.

IC-2 (Synthesized from Compound 6b)

Formic acid (8 mL, 0.21 mol) was added to the compound 6b (1.3 g, 2.1 mmol), and the mixture was stirred overnight at room temperature. After completion of the reaction, formic acid was distilled away while the mixture was concentrated under reduced pressure. The resulting residue was purified by silica gel column chromatography (AcOEt/EtOH=30/1) to yield IC-2 (1.0 g, 1.9 mmol, 90%) as a colorless solid.

IC-2-R

Compound IC-2-R (a substituent R=OMe, Cl, F, or $NO_2$) was synthesized in accordance with the scheme designated in FIG. 31.

IC-2 (Synthesized from Compound 9b)

Benzyl isocyanate (1.4 g, 11 mmol) was added to a $CH_2Cl_2$ solution (10 mL) containing the compound 9b (3.3 g, 8.3 mmol), and the mixture was stirred overnight at room temperature. After completion of the reaction, $CH_2Cl_2$ was distilled away while the mixture was concentrated under reduced pressure. The resulting residue was purified by silica gel column chromatography (AcOEt/EtOH=30/1) to yield IC-2 (3.7 g, 6.9 mmol, 83%) as a colorless solid.

4-(4-Methoxybenzyloxy)phenylacetic acid $K_2CO_3$ (4.4 g, 32 mmol) and 4-methoxybenzyl chloride (1.3 g, 8 mmol) were added to a dry-DMF solution (20 mL) containing methyl 4-hydroxyphenylacetate (2.7 g, 16 mmol), and the mixture was stirred at room temperature for 24 h. The reaction mixture was injected into ice-cold water (30 mL) and a product was then extracted with EtOAc. A separated organic layer was washed with saturated saline and dried with $Na_2SO_4$. After that, the sample was filtered and concentrated under reduced pressure. MeOH (24 mL) and THF (8 mL) were added to the resulting residue, and the mixture was stirred and made homogeneous. Next, a NaOH aqueous solution (0.96 g, 24 mmol, 6 mL) was slowly added, and the mixture was stirred at room temperature for 2 h. An organic solvent was distilled away while the mixture was concentrated under reduced pressure. Then, water (50 mL) was added and the mixture was made acidic with 1 M sulfuric acid. Subsequently, ethyl acetate and THF were used to extract a product. An organic layer was washed twice with saturated saline and dried with $Na_2SO_4$. After that, the sample was filtered and concentrated under reduced pressure. The resulting residue was recrystallized EtOAc-THF) to (using give pure 4-(4-methoxybenxyloxy)phenylacetic acid (1.8 g, 6.8 mmol, 85%).

4-Methoxymethoxyphenylacetic acid

DIEA (3.9 g, 30 mmol) was added to a $CH_2Cl_2$ solution (15 mL) containing methyl 4-hydroxyphenylacetate (2.5 g, 15 mmol). While the mixture was cooled in an ice water bath, chloromethyl methyl ether (1.8 g, 23 mmol) was added. The mixture was stirred at that temperature for 10 min. Then, the temperature was returned to room temperature, and the mixture was further stirred overnight. $CH_2Cl_2$ and excessive chloromethyl methyl ether were removed while the mixture was concentrated under reduced pressure. After that, MeOH (25 mL) was added and the mixture was stirred and made homogeneous. Following that, a KOH aqueous solution (3.0 g, 45 mmol, 5 mL) was added, and the mixture was stirred at room temperature for 1.5 h. Water (20 mL) was added to the reaction mixture and an aqueous layer was separated. Thereafter, a saturated $NH_4Cl$ aqueous solution (20 mL) was added to adjust by using a diluted sulfuric acid a pH to about 4. EtOAc was then added thereto to separate an organic layer. After that, the organic layer was washed with saturated saline and dried with $Na_2SO_4$. The resulting sample was filtered, concentrated under reduced pressure, and dried under reduced pressure to give 4-methoxymethoxyphenylacetic acid (2.2 g, 11 mmol, 76%).

Benzyl 4-hydroxyphenylacetate

NaH (60% in oil, 0.88 g, 22 mmol) was added to a dry-DMF solution (20 mL) containing 4-hydroxyphenylacetic acid (3.0 g, 20 mmol) that was cooled under an Ar atmosphere in an ice water bath. The mixture was stirred at that temperature for 30 min. Next, benzyl bromide (6.8 g, 40 mmol) was added in several portions over 30 min. The mixture was stirred for 3 h while cooled in an ice water bath, and further stirred overnight at room temperature. Then, water (20 mL) and EtOAc (20 mL) were added to the reaction mixture and well stirred. After that, an organic layer was separated, washed with 5%-NaHCO$_3$ aqueous solution and saturated saline, and dried with Na$_2$SO$_4$. After the sample was filtered and concentrated under reduced pressure, hexane was added to the resulting solid. Subsequently, suction filtration was carried out and the resulting solid was dried under reduced pressure to give benzyl 4-hydroxyphenylacetate (3.4 g, 14 mmol, 70%).

4-(tert-Butyldimethylsiloxymethyl)phenylacetic acid

NaH (60% in oil, 0.44 g, 11 mmol) was added to a dry-DMF solution (10 mL) containing 4-hydroxymethylphenylacetic acid (1.7 g, 10 mmol) that was cooled under an Ar atmosphere in an ice water bath. After the mixture was stirred at that temperature for 30 min, benzyl bromide (3.4 g, 20 mmol) was added in several portions over 30 min. The mixture was stirred for 2 h while cooled in an ice water bath, and further stirred overnight at room temperature. Then, water (20 mL) and AcOEt (20 mL) were added to the reaction mixture and well mixed. After that, an organic layer was separated, washed with 5%-NaHCO$_3$ aqueous solution and saturated saline, and dried with Na$_2$SO$_4$. After filtration, AcOEt was distilled away while the sample was concentrated under reduced pressure. The sample was further distilled under reduced pressure to distill excessive benzyl bromide away. Dry DMF (10 mL) was added to the resulting residue and the mixture was stirred and made homogeneous. Then, tert-butyldimethylsilyl chloride (2.0 g, 13 mmol) and imidazole (1.4 g, 20 mmol) were added, and the mixture was stirred at room temperature for 2 h. Water (20 mL) was added to the reaction mixture, and a product was then extracted with AcOEt. A separated organic layer was washed with saturated saline and dried with Na$_2$SO$_4$. After the sample was filtered and concentrated under reduced pressure, EtOH (15 mL) was added to the resulting residue. The mixture was stirred and made homogeneous, followed by addition of 5%-Pd/C (1.1 g). Meanwhile, the inside of the system is replaced with H$_2$. After the sample was stirred at room temperature for 4 h, Pd/C was removed by filtration that uses a double layer filter paper. After a filtrate was concentrated under reduced pressure, the residue was subject to silica gel column chromatography (AcOEt/hexane=½) to give 4-(tert-butyldimethylsiloxymethyl)phenylacetic acid (0.95 g, 3.4 mmol, 34%).

IC-2-OMOM

Diphenylphosphoryl azide (0.83 g, 3 mmol) and Et$_3$N (0.36 g, 3.6 mmol) were added to a toluene solution (10 mL) containing 4-methoxymethoxyphenylacetic acid (0.59 g, 3 mmol), and the mixture was stirred at 80° C. for 2 h. After the mixture was allowed to cool, hexane (15 mL) was added and the mixture was stirred for a certain time. Next, a supernatant was collected by decantation. Hexane (7 mL) was again added to the residue, and the mixture was stirred for a certain time. Then, a supernatant was collected by decantation, and this operation was repeated one more time. The collected supernatant was concentrated under reduced pressure. After that, CH$_2$Cl$_2$ (8 mL) was added to the residue and the mixture was made homogeneous. Subsequently, compound 9b (0.40 g, 1 mmol) was added thereto. After the mixture was stirred overnight at room temperature, an organic solvent was distilled away while the mixture was concentrated under reduced pressure. The resulting residue was subject to silica gel column chromatography (AcOEt) to give IC-2-OMOM (0.50 g, 0.85 mmol, 84%).

IC-2-NO2

The same protocol as for IC-2-OMOM and 4-nitrophenylacetic acid were used for the manipulation. In the protocol, however, the step of collecting a supernatant by adding hexane was omitted. After the sample was allowed to cool, CH$_2$Cl$_2$ and the compound 9b were added directly to the reaction mixture. Silica gel column chromatography was conducted at AcOEt/EtOH=8/1. The yield was 24%.

IC-2-OPMB

The same protocol as for IC-2-OMOM and 4-(4-methoxybenzyloxy)phenylacetic acid were used for the manipulation. In this regard, however, addition of only toluene failed to convert 4-(4-methoxybenzyloxy)phenylacetic acid to a homogeneous solution. Thus, dry-THF (5 mL) was also added. Silica gel column chromatography was conducted at AcOEt/EtOH=30/1. The yield was 93%.

IC-2-MOTBS

The same protocol as for IC-2-OMOM and 4-(tert-butyldimethylsiloxymethyl)phenylacetic acid were used for the manipulation. Silica gel column chromatography was conducted by using AcOEt. The yield was 66%.

IC-2-OH

CF3CO$_2$H (1.1 mL, 14 mmol) was added to a CH$_2$Cl$_2$ solution (3 mL) containing IC-2-OMOM (0.44 g, 0.74 mmol), and the mixture was stirred at room temperature for 1 h. The reaction mixture was slowly injected into 5%-NaHCO$_3$ aqueous solution (40 mL), and a product was extracted by using AcOEt. A separated organic layer was washed with saturated saline and dried with Na$_2$SO$_4$. Then, the sample was filtered and concentrated under reduced pressure. The resulting residue was purified by silica gel column chromatography (AcOEt/EtOH=30/1) to give IC-2-OH (0.16 g, 0.29 mmol, 39%).

IC-2-MOH

To a dry-THF solution (8 mL) containing IC-2-MOTBS (0.51 g, 0.75 mmol) was added a TBAF-containing THE solution (1 M, 1.5 mL, 1.5 mmol) cooled with ice water. After stirred at that temperature for 10 min, the mixture was stirred at room temperature for 1.5 h. Water (20 mL) was added to the reaction mixture, and a product was then extracted with AcOEt. A separated organic layer was washed with saturated saline and dried with Na$_2$SO$_4$. Then, the sample was filtered and concentrated under reduced pressure. The resulting residue was purified by silica gel column chromatography (AcOEt/EtOH=10/1) to give IC-2-MOH (0.30 g, 0.53 mmol, 71%).

8.2 Inhibitory Effect on Wnt/β-catenin Signal

First, the HuH7 cells that were at 70 to 90% confluency and stably expressed the pTCF4-CMVpro-Luc were collected, and the $1 \times 10^4$ cells were seeded in each well of a 96-well plate (FALCON). After 24 hours, the cells were treated with IC-2 derivatives (IC-2-OMe, IC-2-F, IC-2-C$_1$, or IC-2-NO$_2$) at concentrations indicated in FIGS. 38 and 39, and further incubated at 37° C. DMSO was used as a control. Four days after the low-molecular-weight compound treatment, 100 µL of Steady-Glo (PROMEGA, Wisconsin, USA) was added to each well of a 96-well white plate (Corning Inc., New York, USA) and the mixture was incubated at room temperature for 5 min. Then, a fluorescence plate reader Infinite F500 (TECAN, Zurich, Switzerland) was used to measure luciferase activity.

Figure 38:
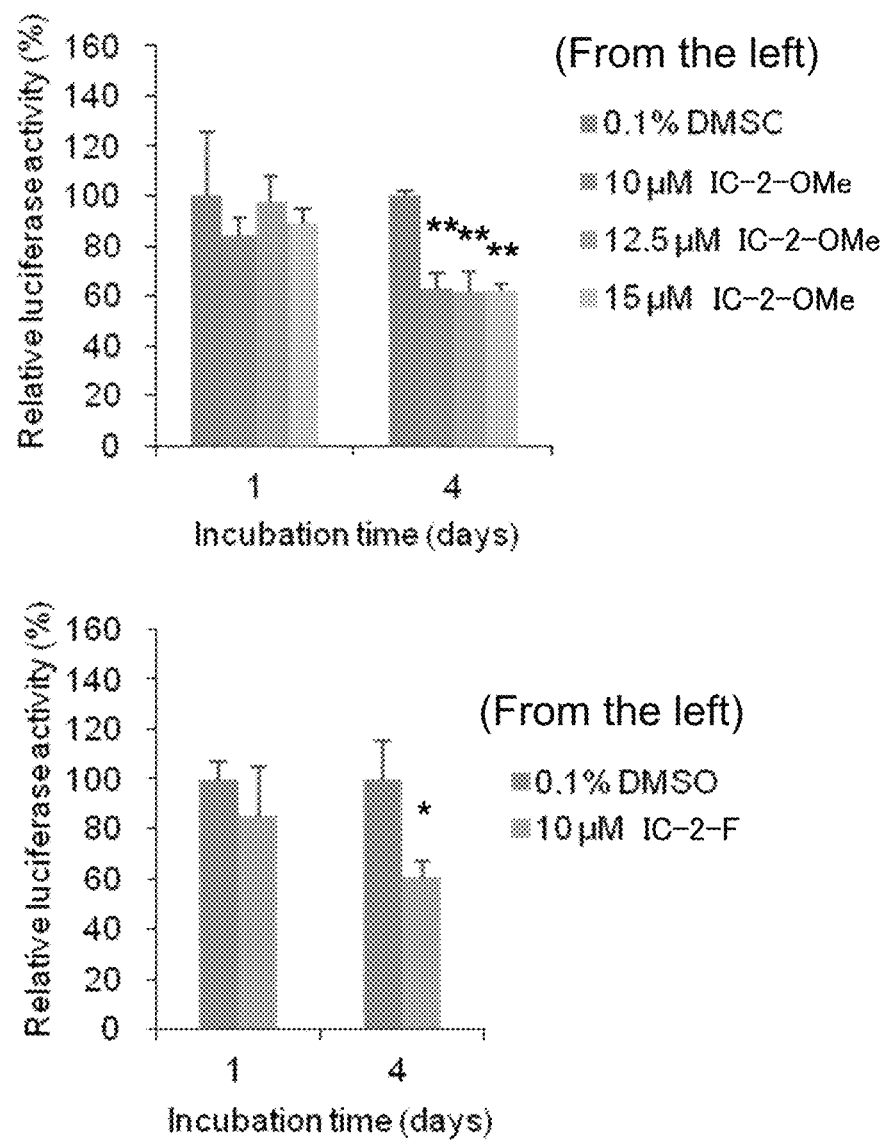
FIG. 38 is graphs showing the results of examining an inhibitory effect of IC-2 derivatives on a Wnt/β-catenin signal.
Figure 39:
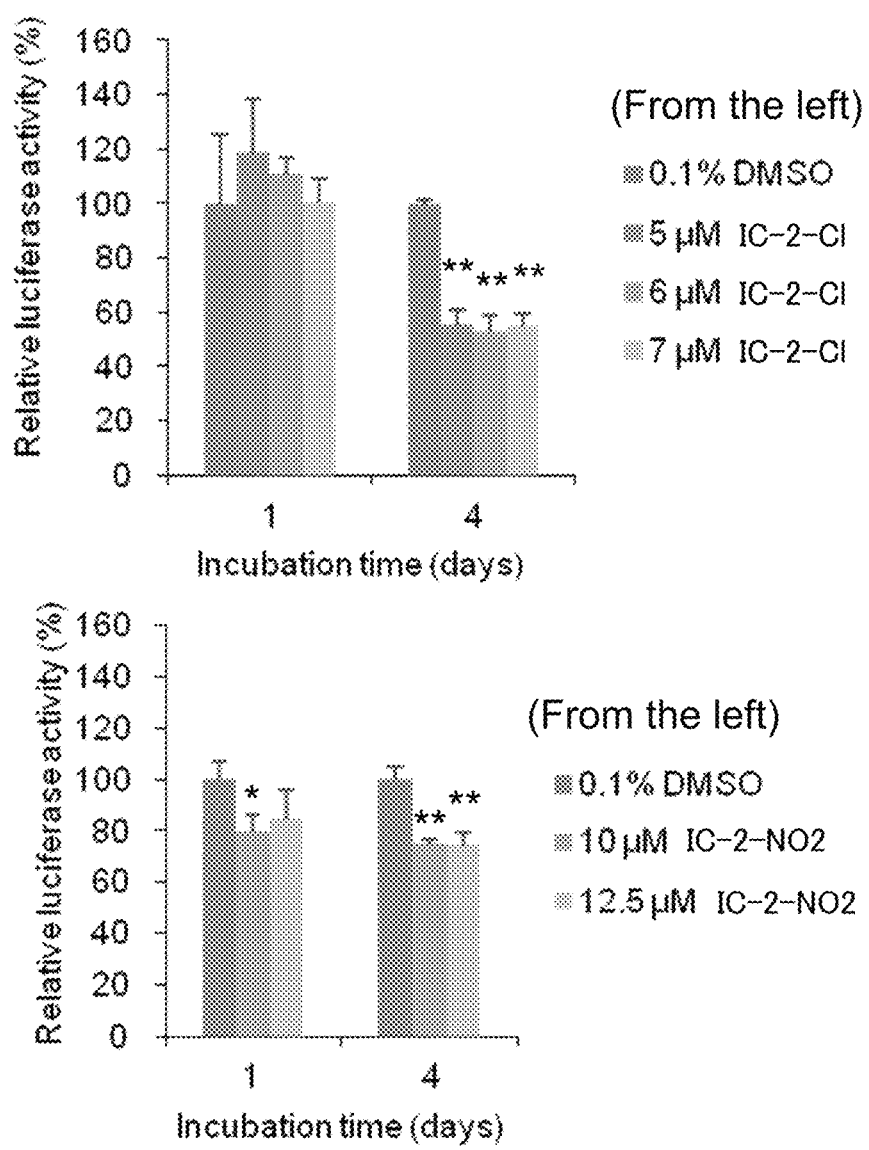
FIG. 39 is graphs showing the results of examining an inhibitory effect of IC-2 derivatives on a Wnt/β-catenin signal.

The results demonstrated that the IC-2 derivatives exerted an inhibitory effect on a Wnt/β-catenin signal (FIGS. 38 and 39).

<Example 9> Inhibition of Fibrosis

9.1 Cell Culture Conditions

A human liver stellate cell line (LX-2 cells) was maintained and cultured in a DMEM containing 10% FBS. The cells used for experiments were suspended in a DMEM containing 1% FBS and plated. The cell density was at about $2.0 \times 10^5$ cell/cm$^2$.

9.2 Concentrations of Low-Molecular-Weight Compound Used

IC-2:0, 15, 20, 25 µM; PN-3-13:0, 5.5, 6.0, 6.5 µM; HC-1:0, 12, 16, 20 µM.

9.3 Luciferase Assay

Figure 40:
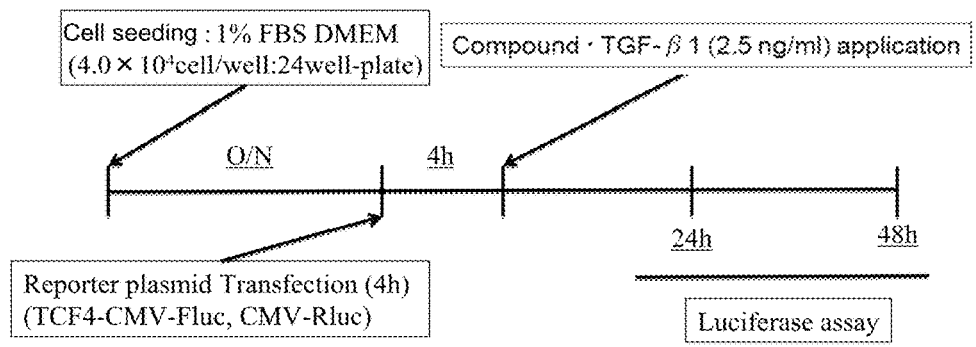
FIG. 40 is a diagram illustrating a protocol of a luciferase assay according to the Examples.

A luciferase assay was used to investigate an inhibitory effect of each low-molecular-weight compound on a Wnt/β-catenin signal. The luciferase assay was conducted under conditions indicated in FIG. 40 and the following sections 9.3.1 to 9.3.2. FIG. 40 illustrates a protocol when the cells were treated with a low-molecular-weight compound+TGFβ. Substantially the same experiment was carried out when the cells were treated with a low-molecular-weight compound alone or a low-molecular weight compound+Wnt3a. Note that TGFβ or Wnt3a was added so as to increase the intensity of a Wnt/β-catenin signal.

9.3.1 Sample Recovery

First, 5× Passive Lysis Buffer was diluted 5-fold with MilliQ water. The lysis buffer was added at 100 µl/well and the plate was shaken for 20 min. The lysate was frozen at −30° C. overnight.

9.3.2 Measurement

The sample frozen a day before, LARII, a Stop&Glo buffer, and a Stop&Glo substrate (materials other than the sample were shaded) were incubated at room temperature for about 1 h. A Stop&Glo solution (49 µl of the Stop&Glo buffer and 1 µl of the Stop&Glo substrate) was prepared for the number of the samples+1. Next, 50 µl of the LARII was dispensed into a 3.5-ml tube. Then, 10 µl of the sample was added and the tube was set in a measurement instrument. After completion of the first assay, 50 µl of the Stop&Glo solution was added and the tube was again set in the measurement instrument for another assay.

9.3.3 Results

Figure 41:
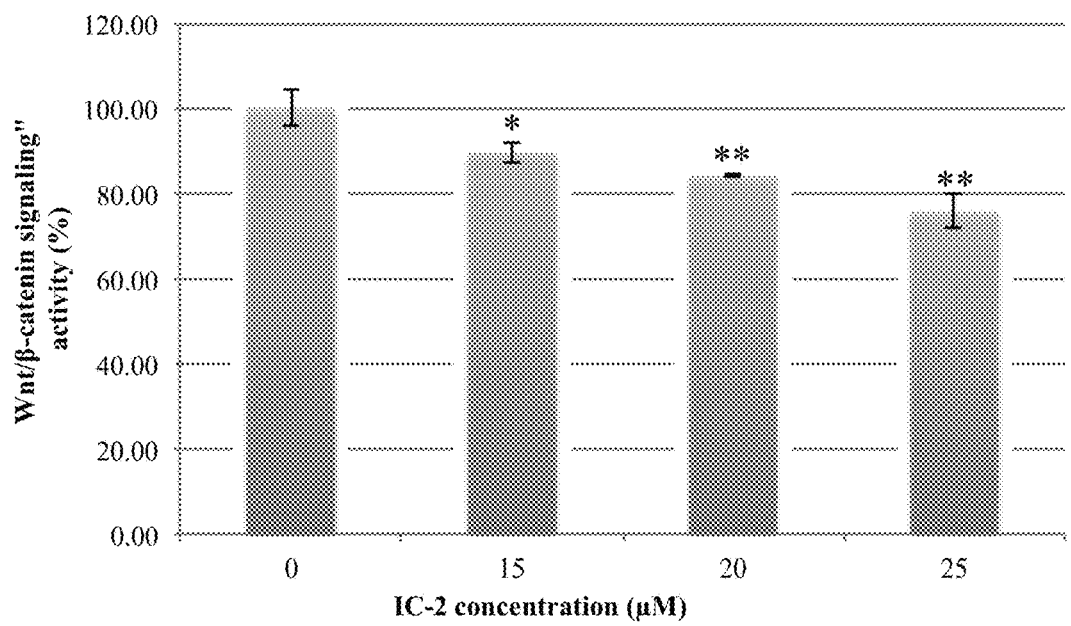
FIG. 41 is a graph showing the results of a luciferase assay performed at 24 h after liver stellate cells were treated with IC-2.
Figure 42:
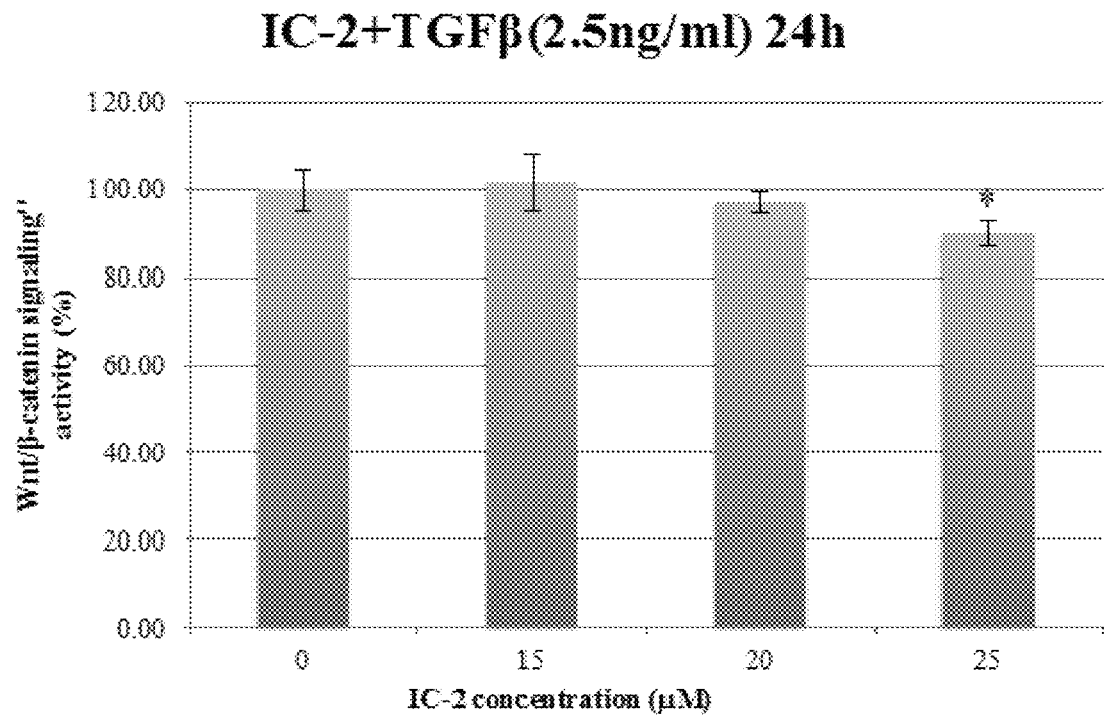
FIG. 42 is a graph showing the results of a luciferase assay performed at 24 h after liver stellate cells were treated with IC-2+TGFβ.
Figure 43:
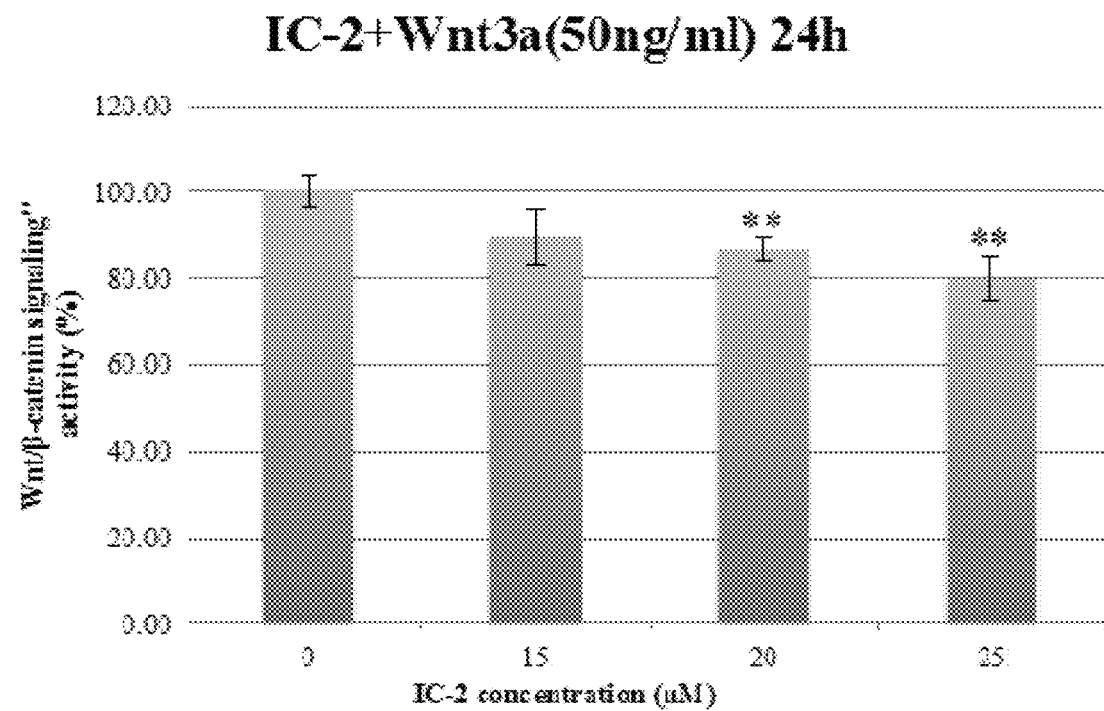

FIGS. 41 to 43 show the results of the luciferase assay at 24 hours after the IC-2 treatment. The treatment using any of IC-2 alone, IC-2+TGFβ, and IC-2+Wnt3a resulted in inhibition of a Wnt/β-catenin signal in the LX-2 cells.

Figure 44:
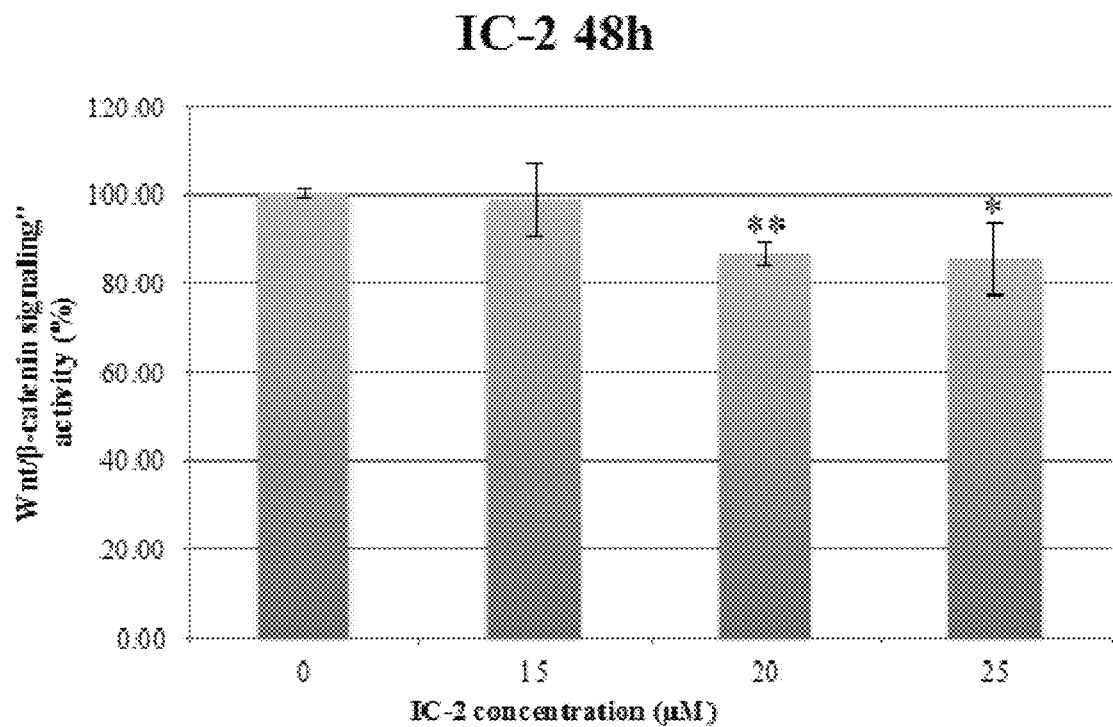
FIG. 44 is a graph showing the results of a luciferase assay performed at 48 h after liver stellate cells were treated with IC-2.
Figure 45:
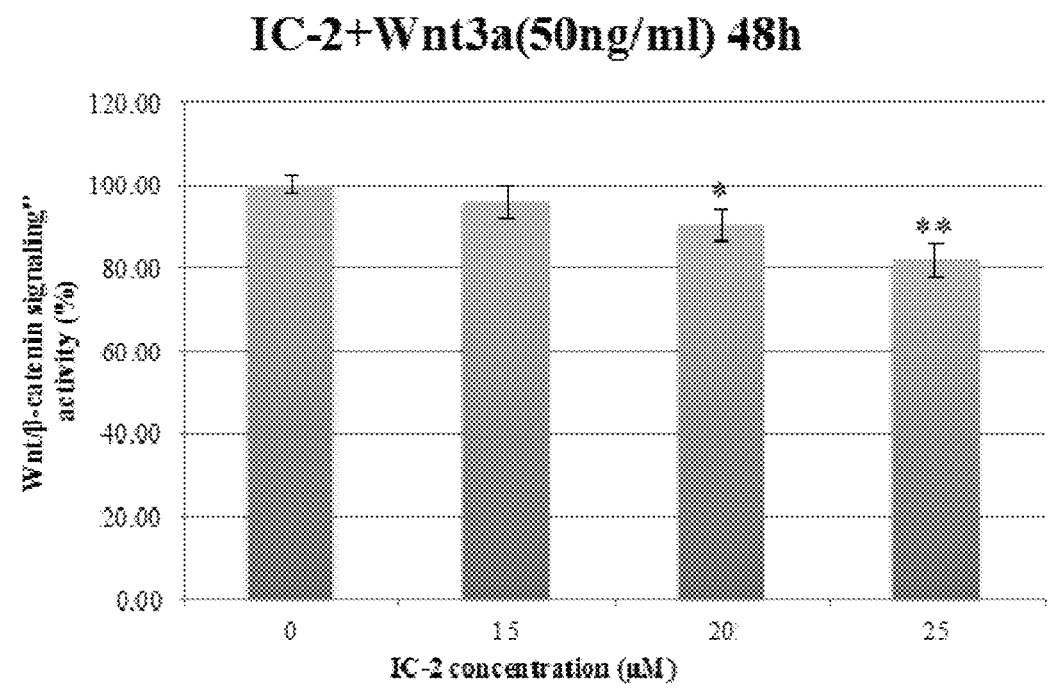
FIG. 45 is a graph showing the results of a luciferase assay performed at 48 h after liver stellate cells were treated with IC-2+TGFβ.
Figure 46:
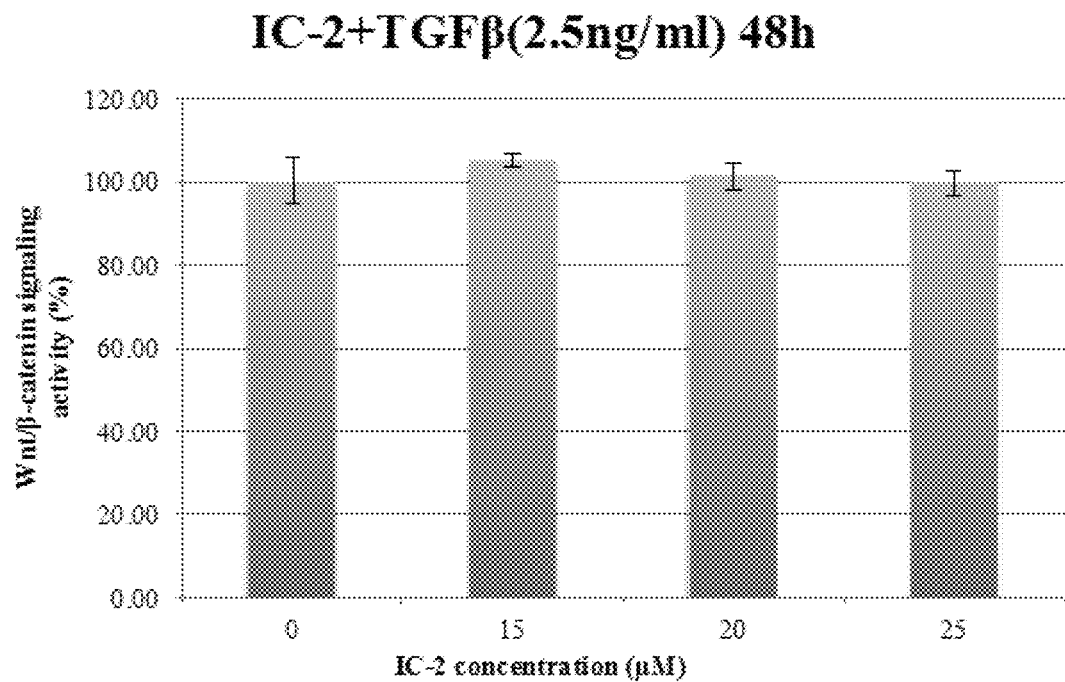

FIGS. 44 to 46 show the results of the luciferase assay at 48 hours after the IC-2 treatment. The treatment using IC-2 alone or IC-2+TGFβ resulted in inhibition of a Wnt/β-catenin signal in the LX-2 cells.

Figure 47:
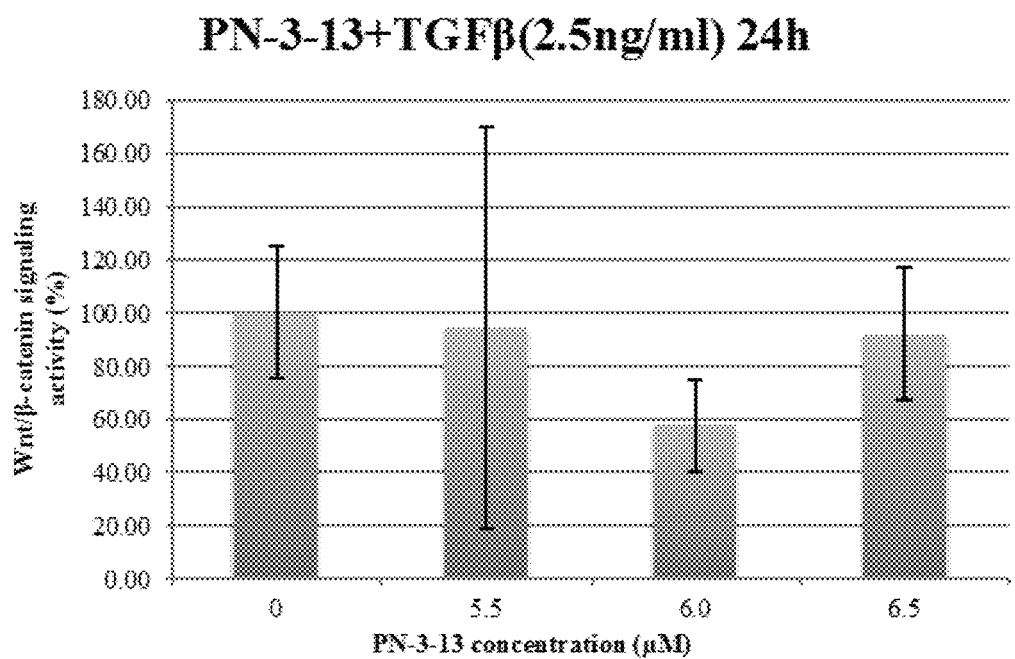
FIG. 47 is a graph showing the results of a luciferase assay performed at 24 h after liver stellate cells were treated with PN3-13+TGFβ.
Figure 48:
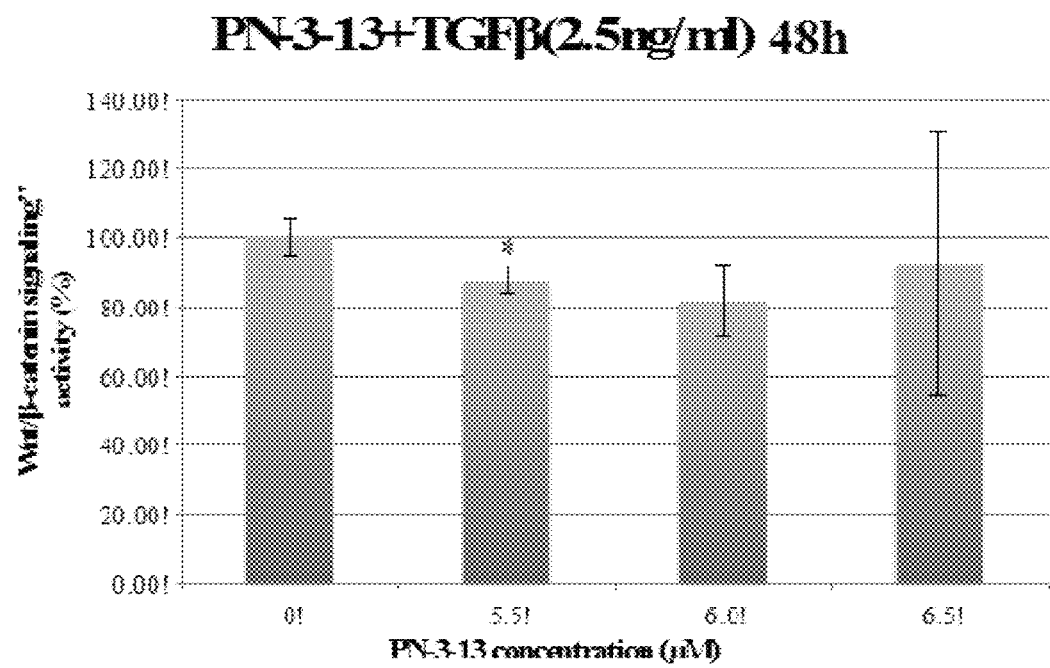
FIG. 48 is a graph showing the results of a luciferase assay performed at 48 h after liver stellate cells were treated with PN3-13+TGFβ.

FIGS. 47 and 48 show the results of the luciferase assay at 24 or 48 hours after the PN3-13 treatment. The treatment using PN3-13+TGFβ resulted in concentration-dependent inhibition of a Wnt/β-catenin signal in the LX-2 cells.

Figure 49:
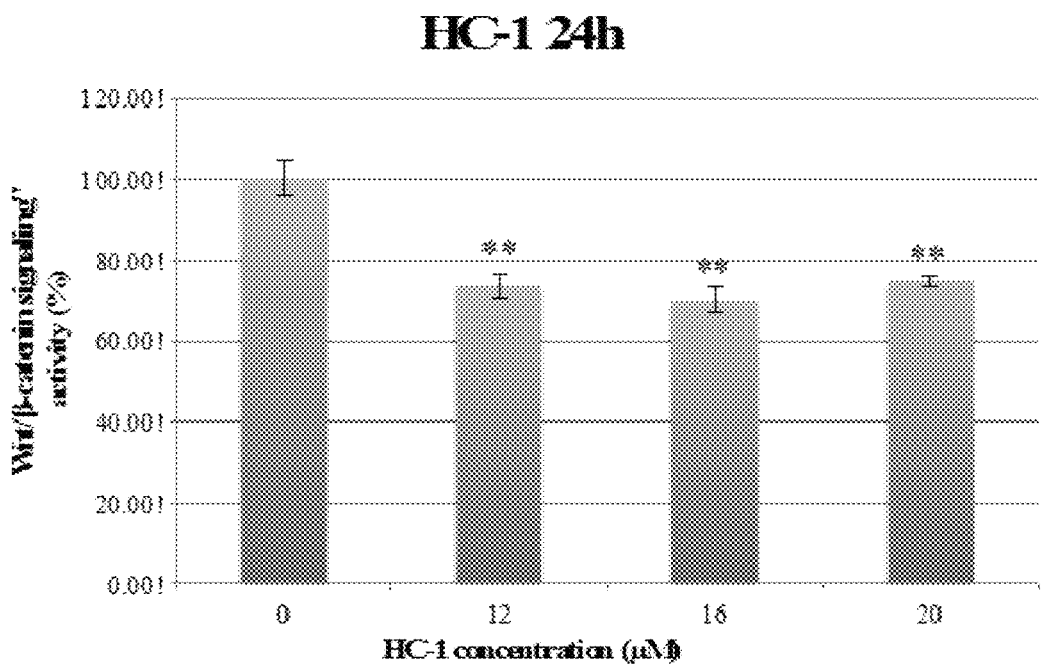
FIG. 49 is a graph showing the results of a luciferase assay performed at 24 h after liver stellate cells were treated with HC-1.
Figure 50:
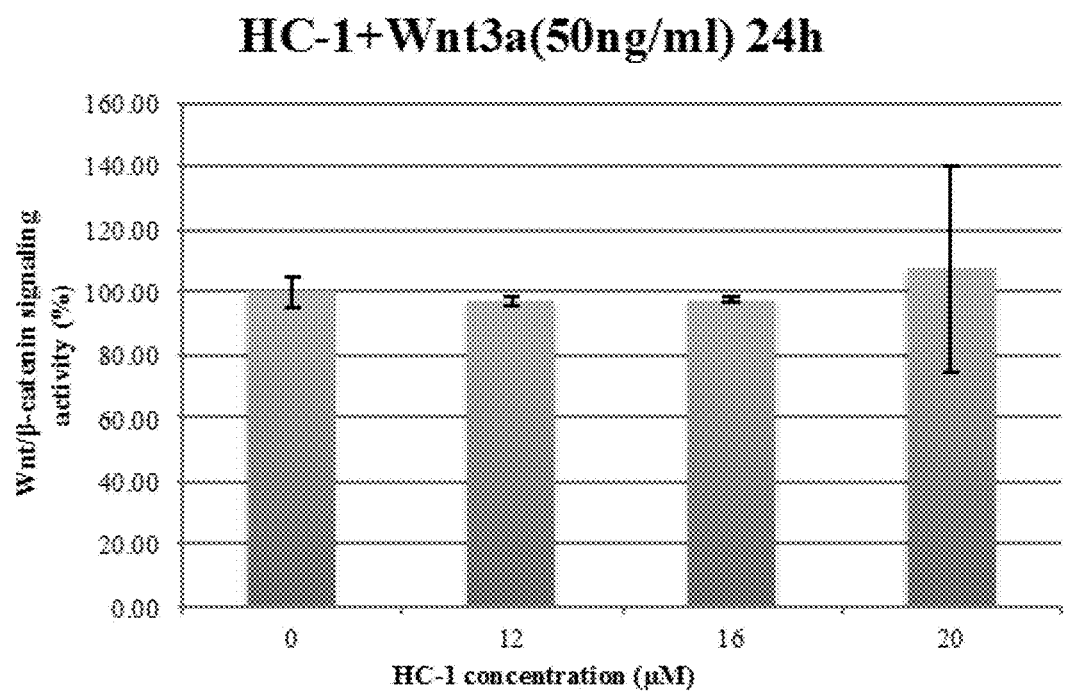
Figure 51:
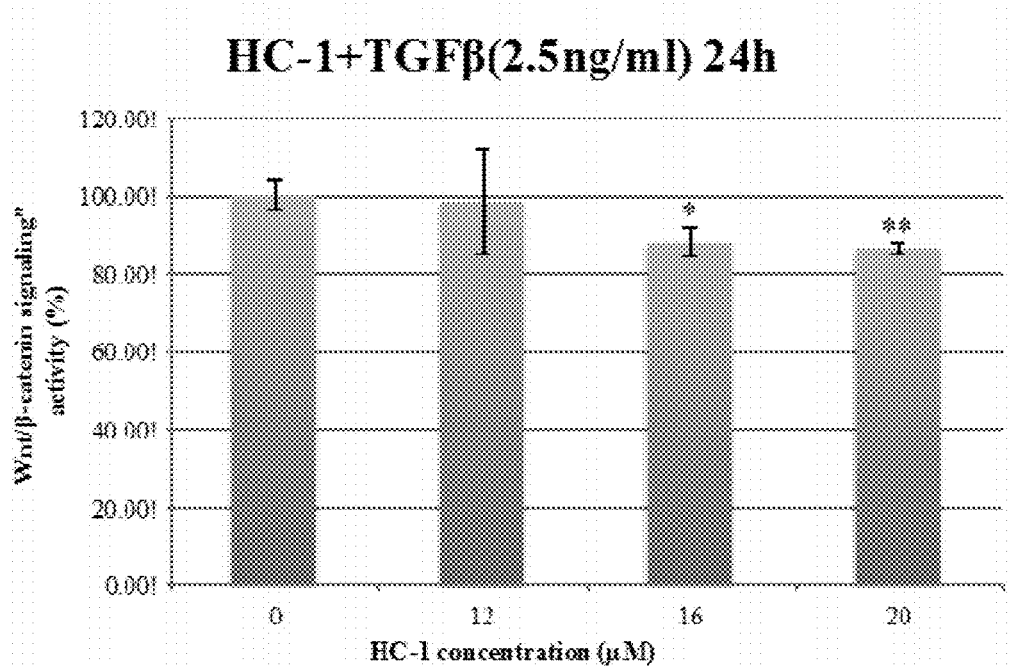
FIG. 51 is a graph showing the results of a luciferase assay performed at 24 h after liver stellate cells were treated with HC-1+TGFβ.

FIGS. 49 to 51 show the results of the luciferase assay at 24 hours after the HC-1 treatment. The treatment using HC-1 alone or HC-1+TGFβ resulted in inhibition of a Wnt/β-catenin signal in the LX-2 cells.

Figure 52:
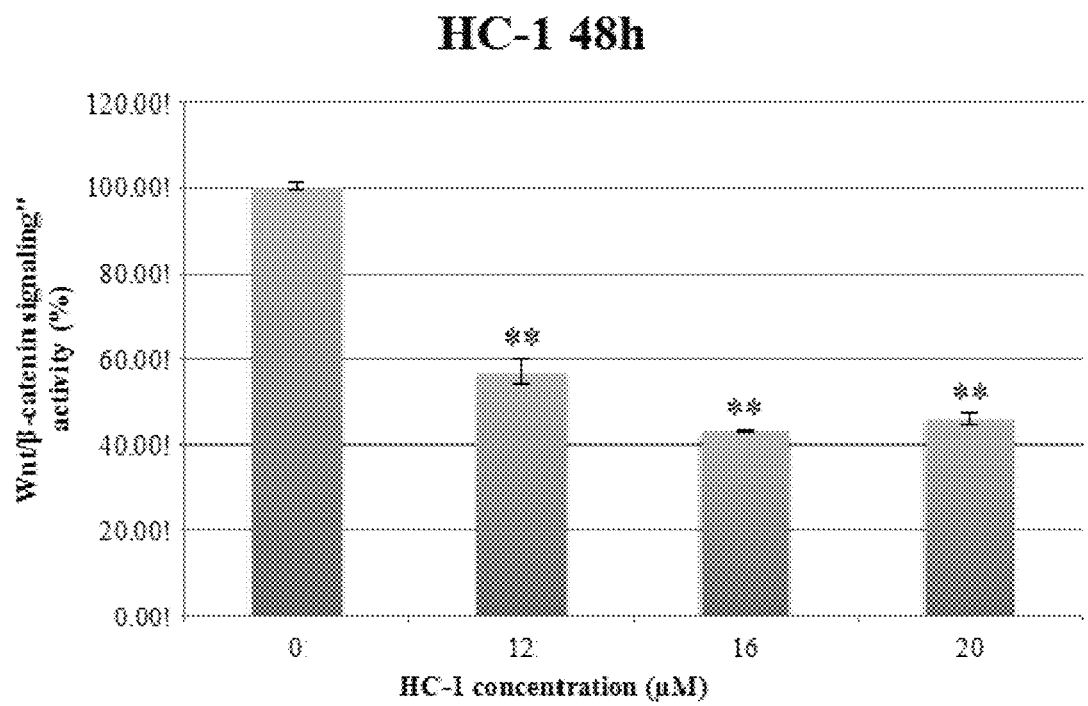
FIG. 52 is a graph showing the results of a luciferase assay performed at 48 h after liver stellate cells were treated with HC-1.
Figure 53:
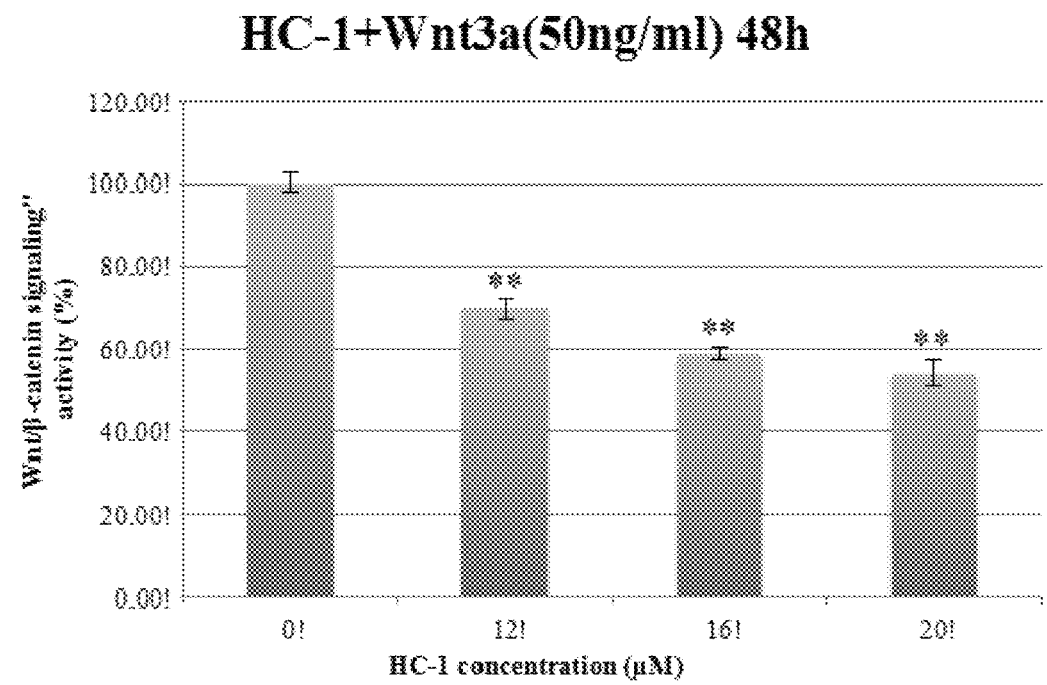
Figure 54:
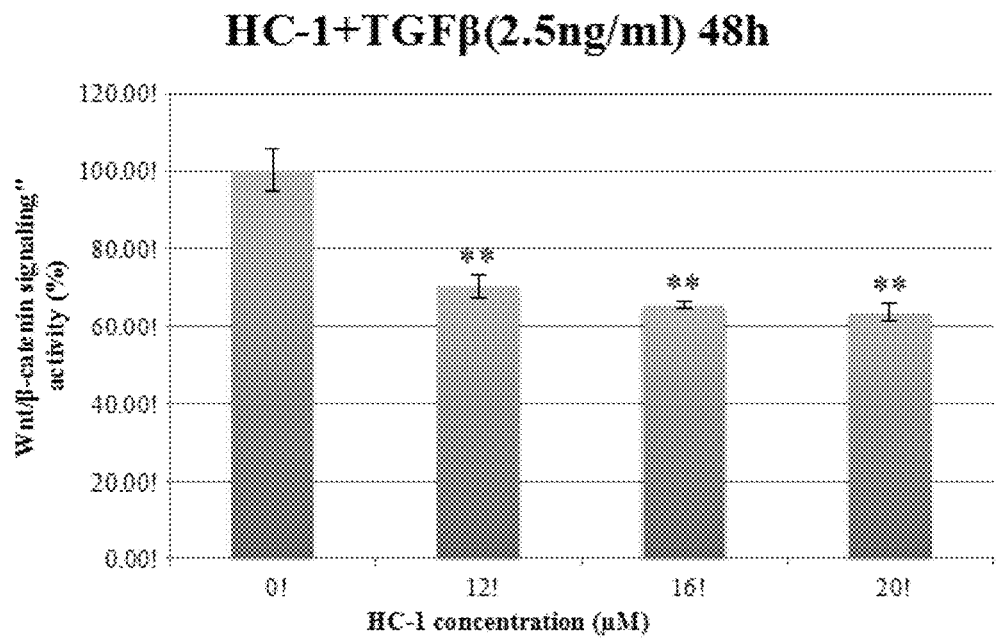
FIG. 54 is a graph showing the results of a luciferase assay performed at 48 h after liver stellate cells were treated with HC-1+TGFβ.

FIGS. 52 to 54 show the results of the luciferase assay at 48 hours after the HC-1 treatment. The treatment using any of HC-1 alone, HC-1+TGFβ, and HC-1+Wnt3a resulted in inhibition of a Wnt/β-catenin signal in the LX-2 cells.

9.4 Real-Time PCR

Figure 55:
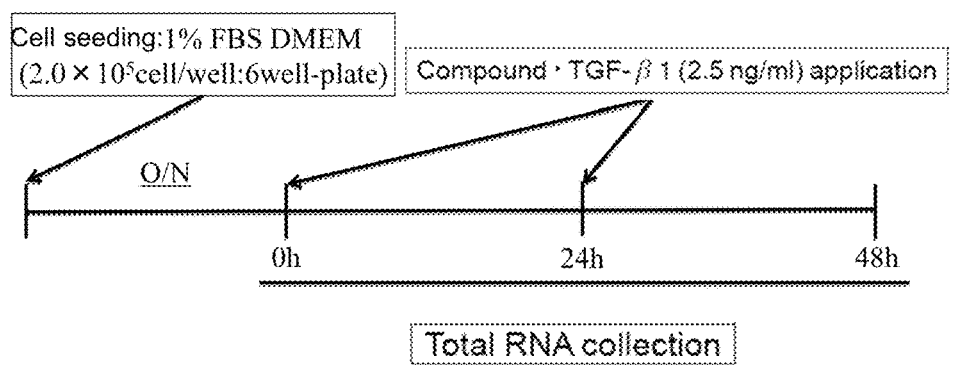
FIG. 55 is a diagram illustrating a protocol of a real-time PCR according to the Examples.

A real-time PCR was carried out to examine an inhibitory effect of each low-molecular-weight compound on fibrosis. The real-time PCR was conducted under conditions indicated in FIG. 55 and the following sections 9.4.1 to 9.4.2. Note that TGFβ, α-SMA, and COL1A1 are fibrosis markers.

9.4.1 Sample Preparation

A pre-Mix was prepared by using MilliQ water: 5.2 L/sample, MgCl$_2$: 0.8 µl/sample, 10 M primer F: 0.5 µl, 10 µM primer R: 0.5 µl, and LightCycler FastStart DNA Master SYBER Green I (1a+1b): 1.0 µM/sample. Next, 8 µL of the pre-Mix was pipetted into each well. Then, 2 µL of the sample was added thereto.

9.4.2 PCR Reaction Temperatures

GAPDH
 95° C.: 10 min-> [95° C.: 10 sec->60° C.: 10 sec->72° C.: 10 sec]×35 cycles.
α-SMA
 95° C.: 10 min-> [95° C.: 10 sec->56° C.: 5 sec->72° C.: 10 sec]×40 cycles.
COL1A1
 95° C.: 10 min-> [95° C.: 10 sec->58° C.: 5 sec->72° C.: 10 sec]×40 cycles.
TGFβ
 95° C.: 10 min-> [95° C.: 1 sec->56° C.: 5 sec->72° C.: 10 sec]×40 cycles.

9.4.3 Results

Figure 56:
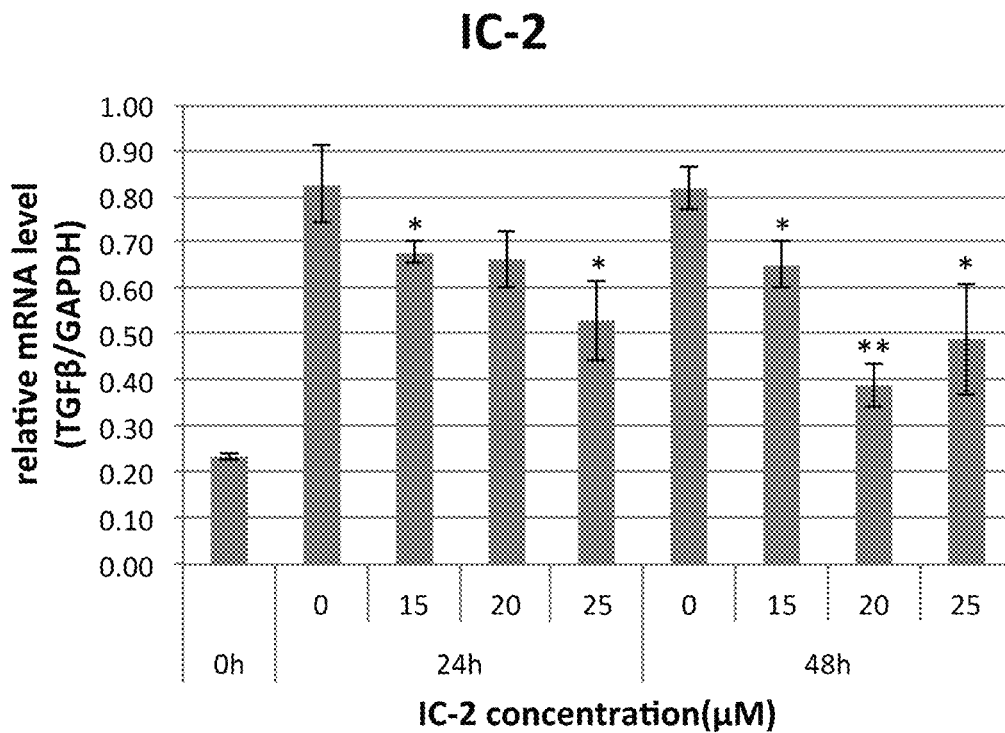
FIG. 56 is a graph showing the results of checking the amount of expression of TGFβ after liver stellate cells were treated with IC-2+TGFβ.
Figure 57:
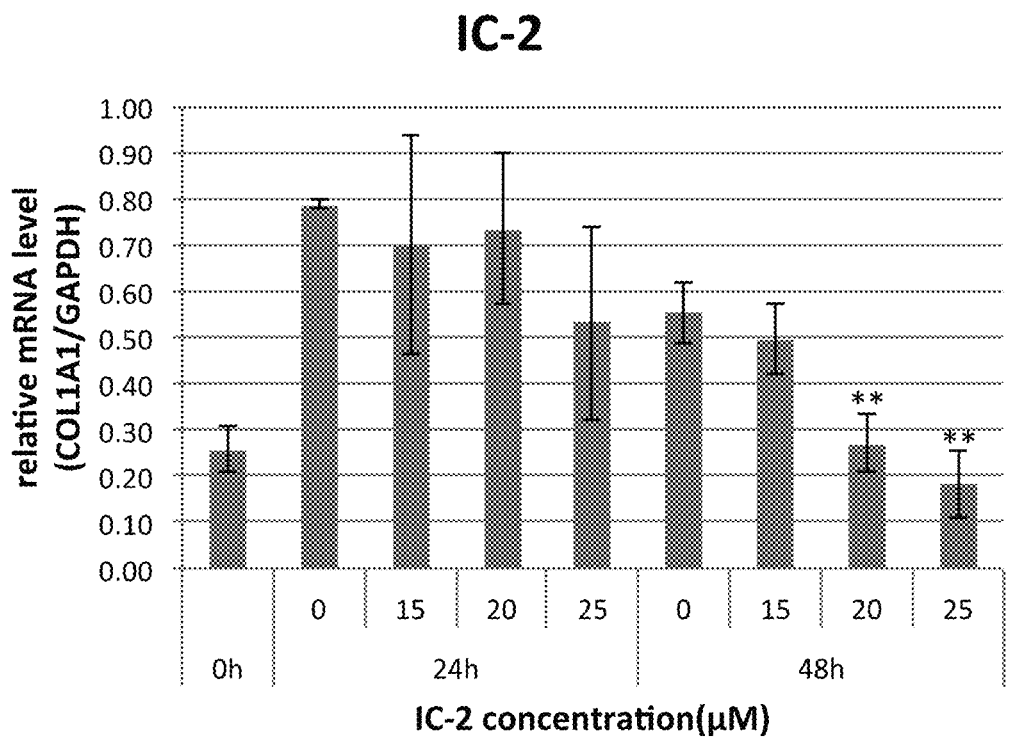
FIG. 57 is a graph showing the results of checking the amount of expression of COL1A1 after liver stellate cells were treated with IC-2+TGFβ.
Figure 58:
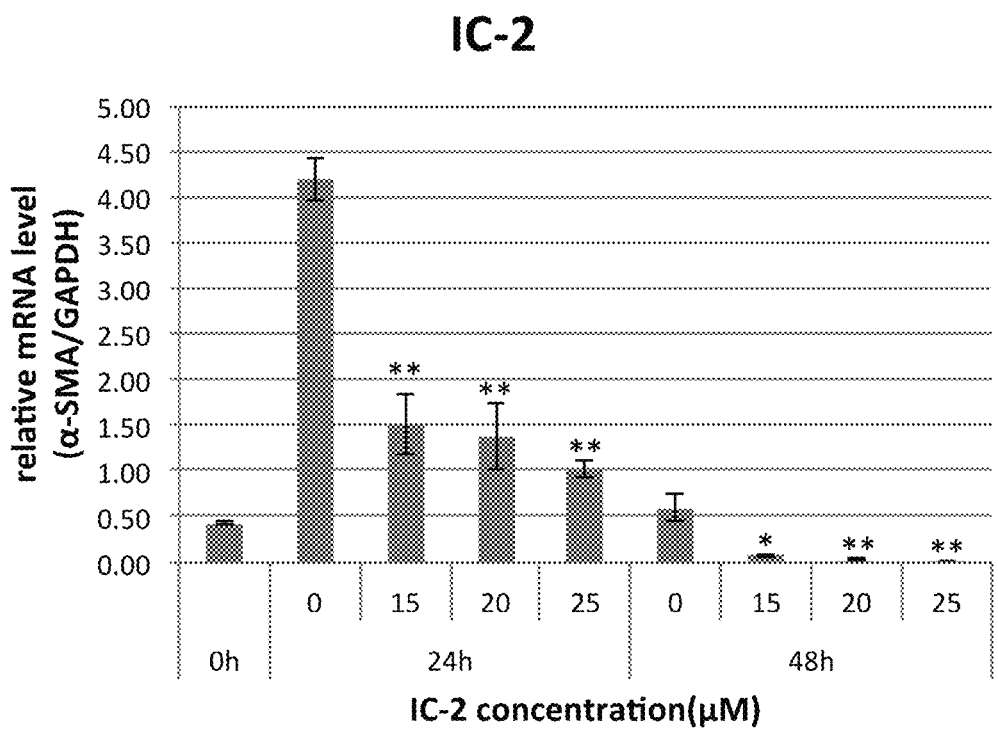
FIG. 58 is a graph showing the results of checking the amount of expression of α-SMA after liver stellate cells were treated with IC-2+TGFβ.

FIGS. 56 to 58 show the results of the real-time PCR at 24 or 48 hours after the IC-2+TGFβ treatment. As the concentration of IC-2 increased, the level of expression of each of the fibrosis markers decreased. The level of expression of α-SMA, in particular, was remarkably reduced.

Figure 59:
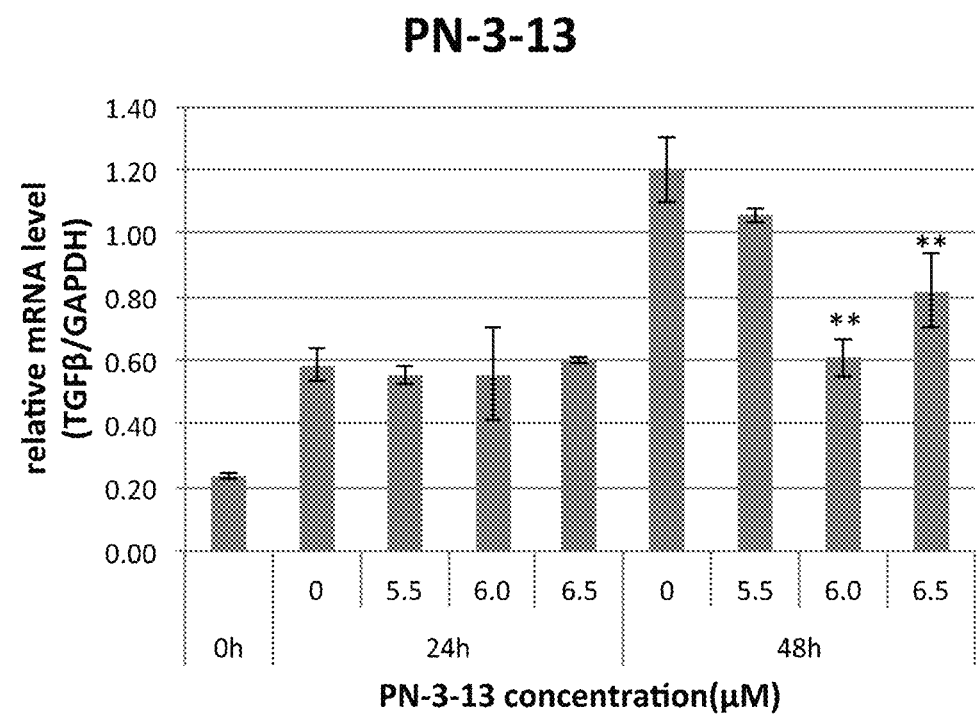
FIG. 59 is a graph showing the results of checking the amount of expression of TGFβ after liver stellate cells were treated with PN3-13+TGFβ.
Figure 60:
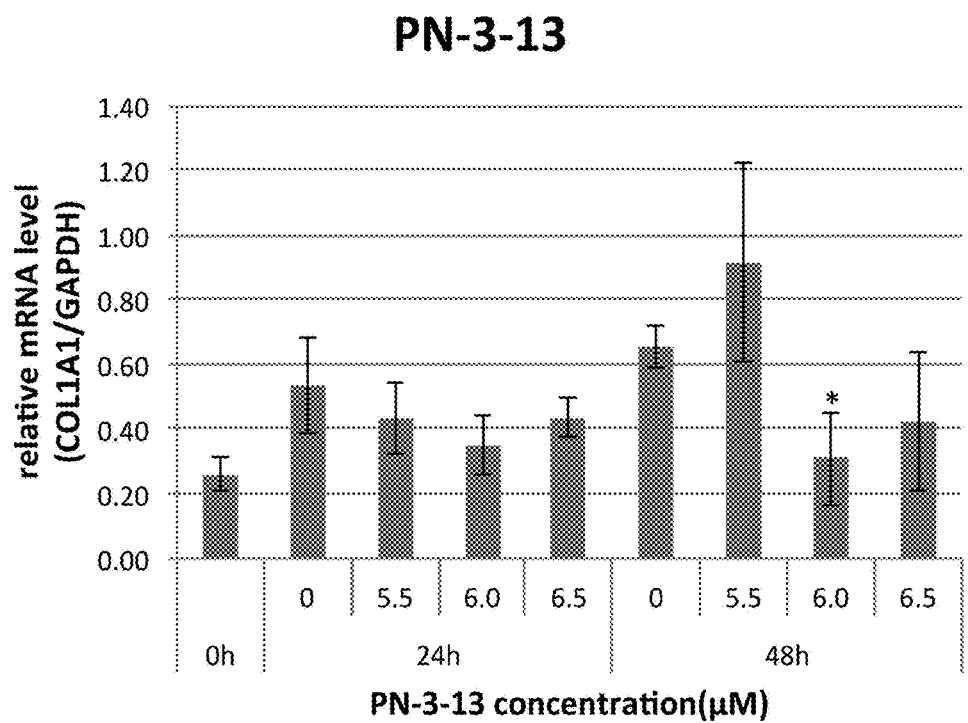
FIG. 60 is a graph showing the results of checking the amount of expression of COLIA1 after liver stellate cells were treated with PN3-13+TGFβ.
Figure 61:
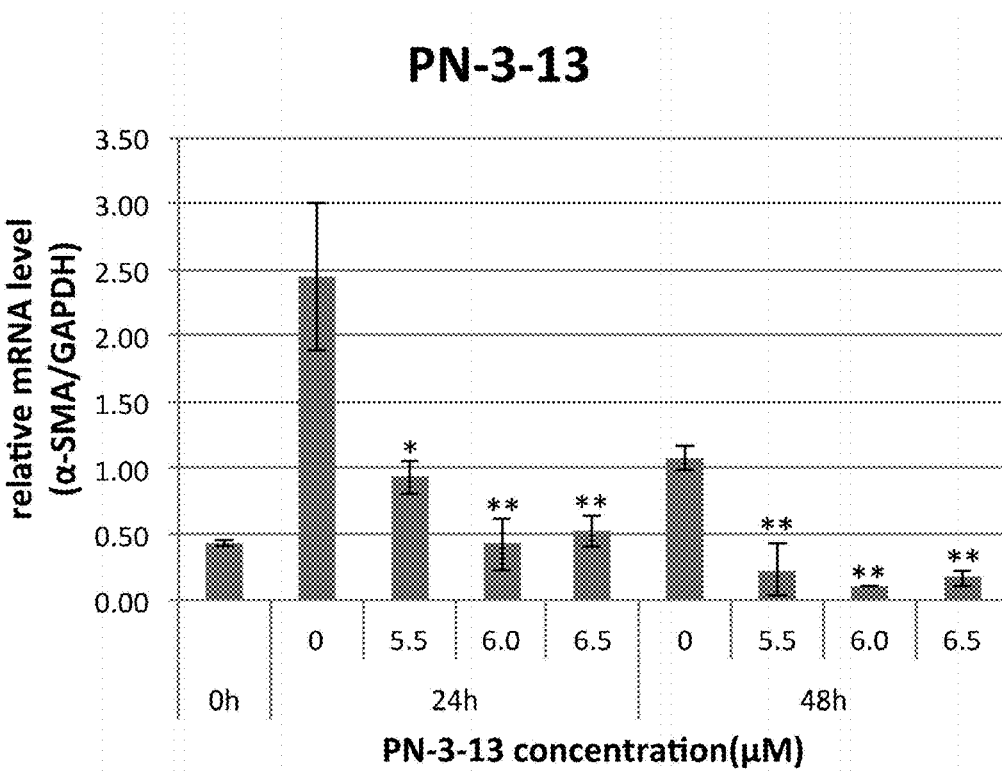
FIG. 61 is a graph showing the results of checking the amount of expression of α-SMA after liver stellate cells were treated with PN3-13+TGFβ.

FIGS. 59 to 61 show the results of the real-time PCR at 24 or 48 hours after the PN3-13+TGFβ treatment. As the concentration of PN3-13 increased, the level of expression of each of the fibrosis markers decreased except the case of the level of TGFβ at 24 hours after the treatment. The level of expression of α-SMA, in particular, was remarkably reduced.

Figure 62:
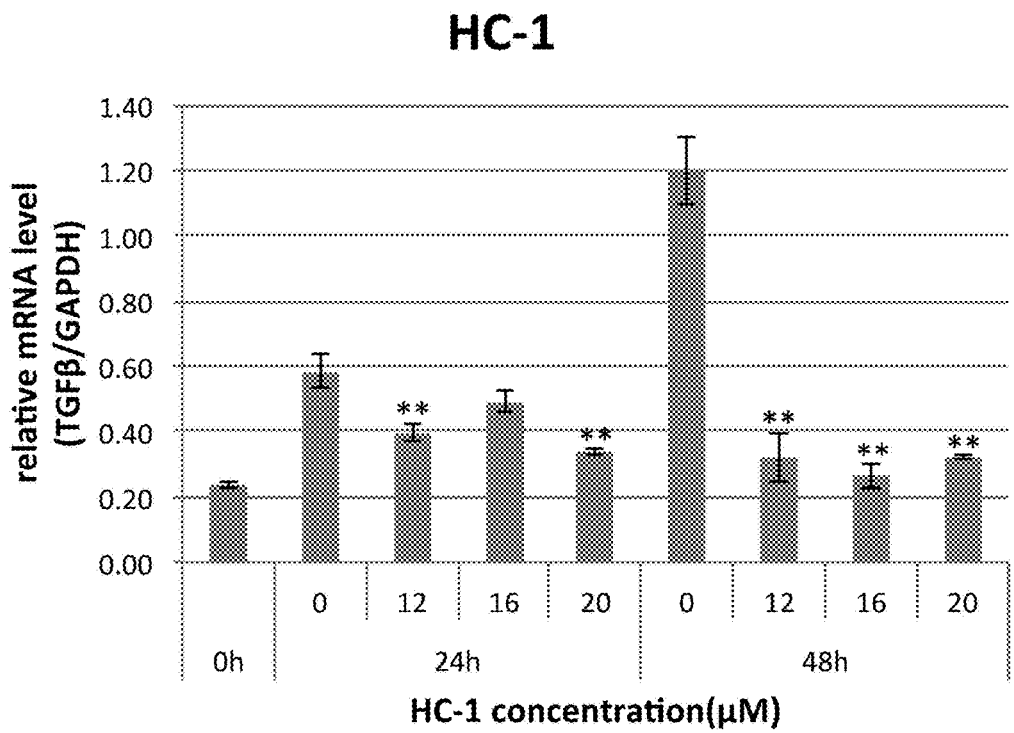
FIG. 62 is a graph showing the results of checking the amount of expression of TGFβ after liver stellate cells were treated with HC-1+TGFβ.
Figure 63:
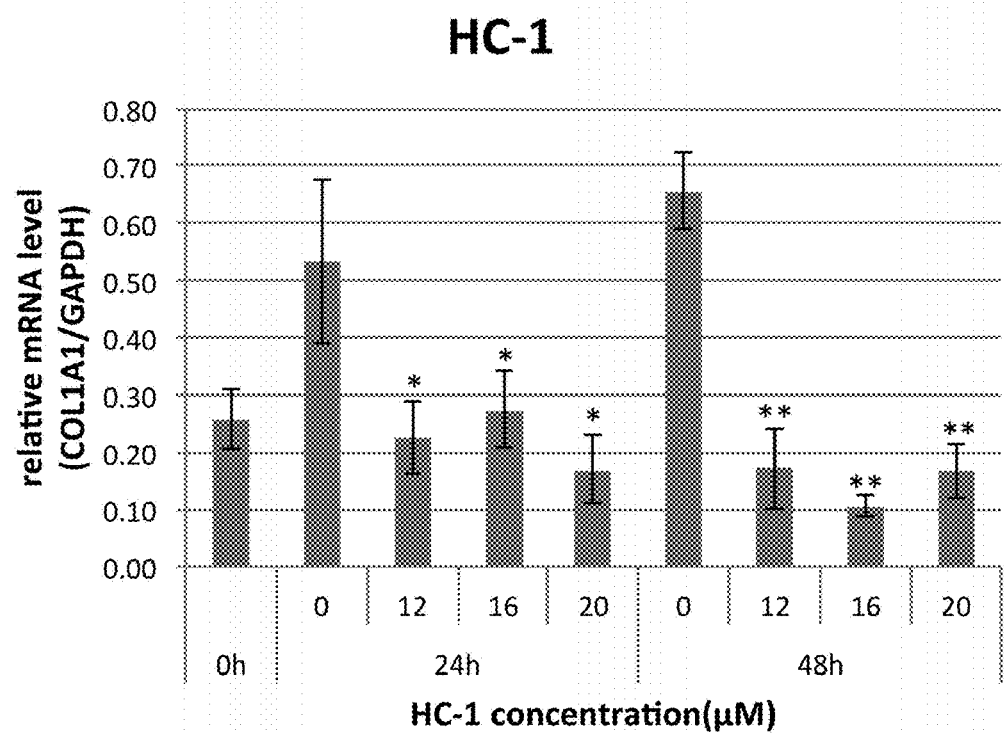
FIG. 63 is a graph showing the results of checking the amount of expression of COL1A1 after liver stellate cells were treated with HC-1+TGFβ.
Figure 64:
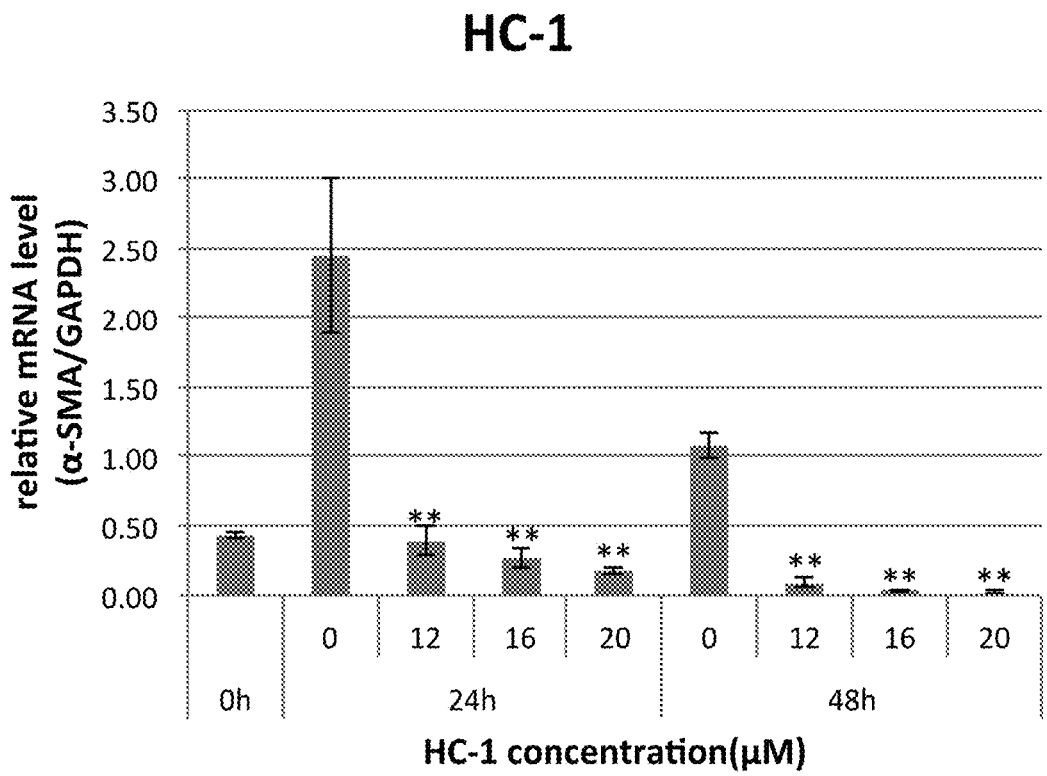
FIG. 64 is a graph showing the results of checking the amount of expression of α-SMA after liver stellate cells were treated with HC-1+TGFβ.

FIGS. 62 to 64 show the results of the real-time PCR at 24 or 48 hours after the HC-1+TGFβ treatment. As the concentration of HC-1 increased, the level of expression of each of the fibrosis markers decreased. The level of expression of α-SMA, in particular, was remarkably reduced.

<Example 10> Liver Disease Model Mice Were Used to Evaluate Effect of Treating Fibrosis 10.1 Experimental Animals and Rearing Conditions First, 7-week-old $C_{57}BL/6$ male mice (Japan SLC, Shizuoka, Japan) were subject to 1-week preparatory rearing. Among them, healthy mice were used. The mice were housed in an animal cage at a room temperature of 22±1° C. and a humidity of 50±5% throughout the preparatory rearing and experimental period and were given ad libitum access to food and water.

10.2 Method for Inducing Liver Fibrosis and Method for Administering Drug

A microsyringe (ITO CORPORATION, Shizuoka, Japan) was used to intraperitoneally administer carbon tetrachloride ($CCl_4$: Wako Pure Chemical Industries, Ltd., Osaka, Japan) at 0.2 ml/kg, 3 times a week, for 4, 6, or 8 weeks. Carbon tetrachloride was dissolved into cone oil (Wako Pure Chemical Industries, Ltd.) at a concentration of 10%. The resulting solution was used. After this carbon tetrachloride solution was administered for 4 weeks, the mice were divided into a vehicle administration group, a glycyrrhizin administration group, an ICG-001 administration group, and an IC-2 administration group. Then, a microsyringe was used to intraperitoneally administer, 3 times a week for 4 weeks, carbon tetrachloride and a drug solution prepared in accordance with the following process. Note that the carbon tetrachloride and the drug solution were alternately administered with one-day interval.

Glycyrrhizin (TOKYO CHEMICAL INDUSTRY CO., LTD., Tokyo, Japan) was dissolved in physiological saline. The solution was prepared at a concentration of 30 mg/ml while the pH was adjusted to 7.0 with 4 M NaOH liquid. IC-2 and ICG-001 (AdooQ BioScience, California, USA) were each dissolved in a WellSolve (Celeste Corporation, Tokyo, Japan) at a concentration of 40 mg/ml and 10 mg/ml, respectively. Next, the mixture was heated for 10 min in a hot water bath at 60° C. and was then completely dissolved. A 9-fold volume of physiological saline was added to the WellSolve solution in which the above drugs had each been dissolved. Next, a required amount of the drug solution was weighed so that glycyrrhizin, IC-2, and ICG-001 were administered at 150 mg/kg, 10.6 or 21.2 mg/kg, and 5 mg/kg, respectively. For the IC-2 and ICG-001, a WellSolve and physiological saline were mixed at 1:9 to prepare each solution. For the glycyrrhizin, physiological saline was added. The volume of each solution was adjusted to 200 µl. In addition, a solution in which a WellSolve and physiological saline were mixed at 1:9 was prepared as a vehicle. Note that an IC-2 dosage was determined on the basis of an effective concentration in vitro.

10.3 Removal of Liver

Four weeks after the carbon tetrachloride administration, a 1-mL disposable syringe with a 27-G needle was used to intraperitoneally administer, to 5 mice, a systemic anesthetic Somnopentyl (Kyoritsuseiyaku Corporation, Tokyo, Japan) at 1 µl/g body weight. Then, anesthesia was induced. After the anesthesia induction, a 1-mL syringe with a 27-G needle was used to collect whole blood from inferior vena cava and the whole liver was removed. In addition, 8 weeks after the carbon tetrachloride administration, 8 mice of each group received the same operation as above. About 1-cm cuboidal tissue sections were cut out from the removed liver and were impregnated in 4% paraformaldehyde (Nacalai Tesque, Kyoto, Japan) for histological analysis. The rest liver tissue was cut into small pieces by using a surgical instrument. The pieces were instantly frozen in liquid nitrogen and then stored in a deep freezer at −80° C. until use in experiments.

10.4 Quantification of Hydroxyproline

The frozen live tissue pieces as prepared by the above procedure were further dissected at a wet weight of 50 mg by using a surgical instrument. Next, 500 µl of ultrapure water was added and the mixture was homogenized with a polytron homogenizer. The homogenized solution was once frozen in liquid nitrogen and thawed at room temperature. Then, a sonicator BioRupture (COSMO BIO co., ltd., Tokyo, Japan) was used to perform sonication for 15 min at a total of 30 cycles, each cycle including 15 sec in an ice water bath and 15 sec of cooling. An equivalent volume of 12 N concentrated hydrochloric acid was added to 100 µl of the resulting sonicated solution and the mixture was subject to hydrolysis for 16 h in a block incubator (IKA, Staufen, Germany) set at 120° C. The rest sonicated solution was used for measuring the amount of protein in the solution. After the hydrolysis, the solution was cooled to room temperature, followed by repeated pipetting and grinding the hydrolysis product into fine pieces. The sample was then centrifuged at 3000 rpm for 5 min. After the centrifugation, 10 µl of a supernatant was placed in a 1.5-mL tube. Then, a cooling evaporator (SAKUMA Corporation, Tokyo, Japan) was used to eliminate hydrochloric acid. Subsequently, a hydroxyproline quantification kit (BioVision, California, USA) was used to quantify the content of hydroxyproline. To the hydrochloric acid-free hydrolysis lysate was added 100 µl of a chloramine T solution, and the mixture was well mixed using a vortex and was allowed to stand for 25 min. After that, 100 µl of a DMAB solution was added and the mixture was reacted for 90 min in a hot water bath at 60° C. After cooling at room temperature, the reaction solution was transferred to a 96-well plate. Subsequently, absorbance at 560 nm was measured by using a microplate reader (TECAN, Zurich, Switzerland). The content of hydroxyproline was calculated from the obtained absorbance in accordance with a standard curve.

The amount of protein in the lysate was determined by the Bradford method using a protein assay dye reagent concentrate (Bio-Rad, California, USA). The lysate was centrifuged at 15000 rpm and 4° C. for 10 min, and 1 µl of the resulting supernatant was placed in a well of a 96-well plate. Next, 200 µl of the protein assay dye reagent concentrate, which was diluted 5-fold with ultrapure water, was added to the well and the mixture was stirred and then allowed to stand for 15 min. Subsequently, absorbance at 595 nm was measured by a microplate reader (TECAN). The amount of protein per µl of lysate was calculated from the obtained absorbance in accordance with a standard curve. Finally, the content of hydroxyproline per mass of protein was determined to evaluate the level of fibrosis.

10.5 Sirius Red Staining

The liver tissue piece, which was cut out by using the above procedure, was fixed in 4% paraformaldehyde at room temperature for 16 hours. After paraffin embedding, tissue sections were prepared by using a microtome. Next, a Picosirius Red Stain Kit (Polysciences, Pennsylvania, USA) was used to stain collagen fibers by using a Sirius red dye in accordance with an attached instruction. Then, an inverted fluorescence phase contrast microscope BZ-9000 (KEYENCE CORPORATION, Tokyo, Japan) was used to take 10 photos of a light field image (at 100× magnification) per tissue section. Finally, a fibrosis-positive area ratio, which was determined as the ratio of the area of fiber, which was stained red, to the tissue area in each captured image, was quantified.

10.6 Results

Figure 65:
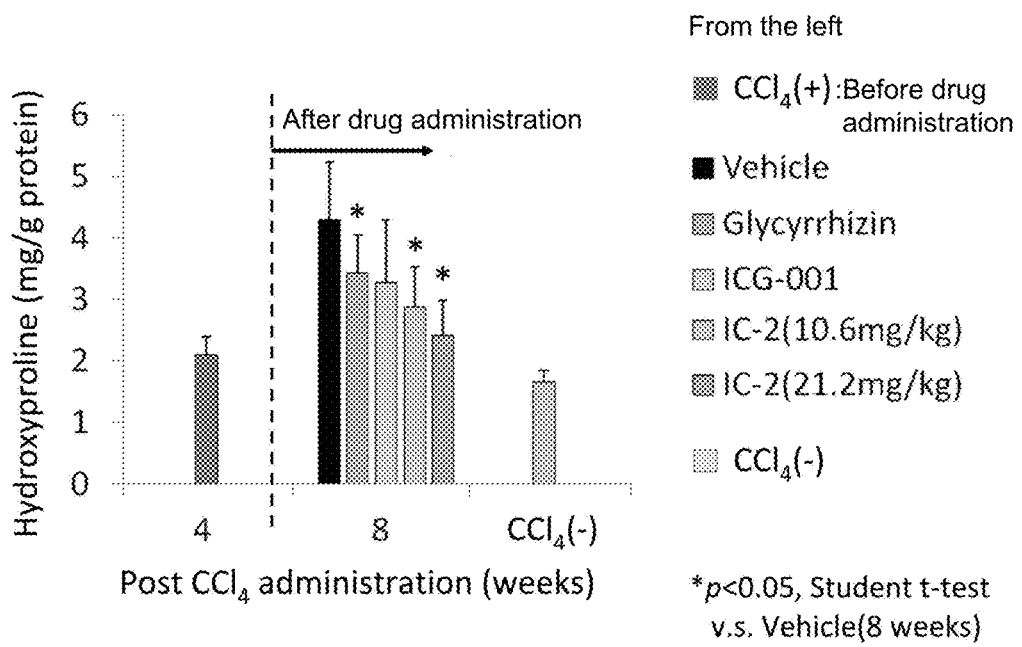
FIG. 65 is a graph showing the results of determining the content of hydroxyproline in liver disease model mice after IC-2 administration.

FIG. 65 shows the results of quantifying the content of hydroxyproline. When compared with the vehicle administration group, the glycyrrhizin administration group (positive control) had a reduced content of hydroxyproline. In the IC-2 administration group, a large decrease was observed.

Figure 66:
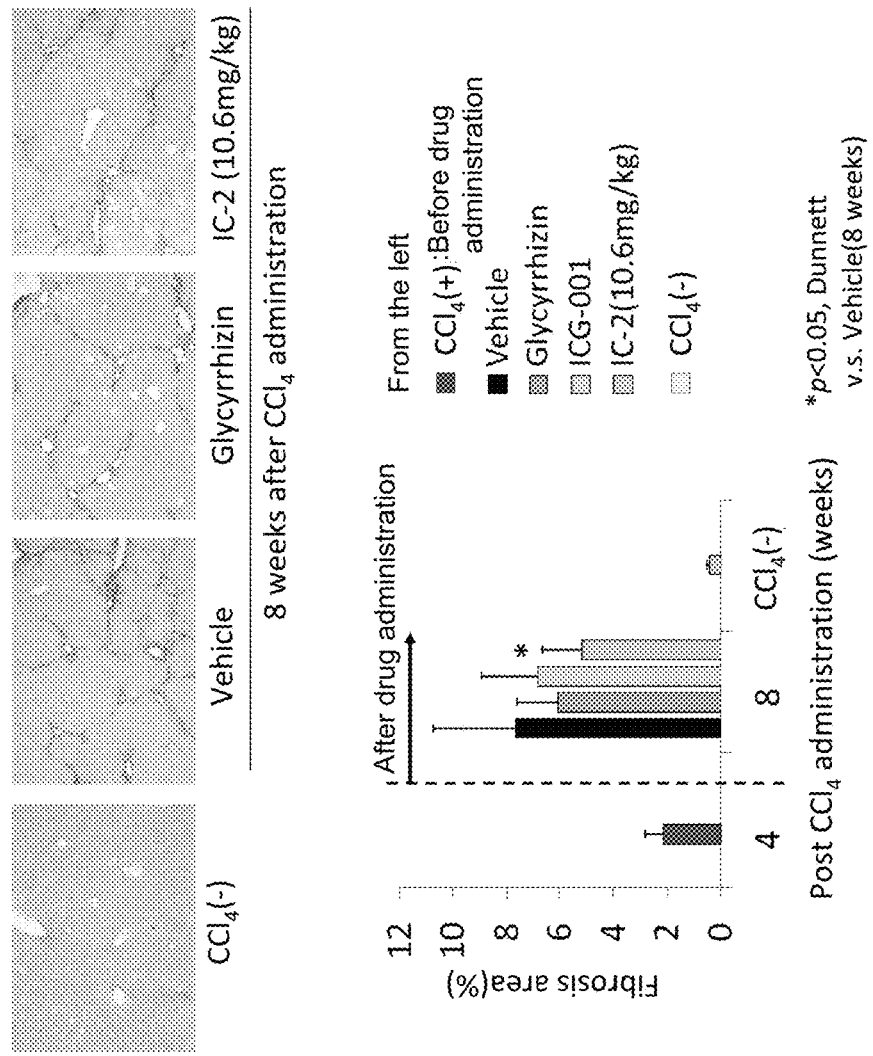
FIG. 66 contains a graph showing the results of quantifying the area of fibrosis in liver disease model mice after IC-2 administration.

FIG. 66 shows the results of quantifying the fibrosis area by using the Sirius red staining. In comparison with the vehicle group, a decrease in the fibrosis area was detected in the IC-2 administration group.

DISCUSSION

As described above, it was demonstrated that use of IC-2, etc., inhibited proliferation of cancer cells and cancer stem cells. Cancer stem cells are known to cause relapse and metastasis of malignant tumors. IC-2, etc., which can inhibit proliferation of cancer stem cells, can thus be said to be a very promising compound as an active ingredient in a therapeutic drug for malignant tumors. Besides, IC-2, etc., also exerted an inhibitory effect on fibrosis, which is likely to cause the occurrence of cancer.

Hereinabove, the present invention has been described based on the Examples. These Examples are absolutely examples. It should be understood by those skilled in the art that various modifications are allowed, and those modifications are also within the scope of the present invention.

The invention claimed is:

1. A method of treating a malignant liver tumor, comprising the step of administering to a subject a compound of formula (3), a salt thereof, or a solvate thereof:

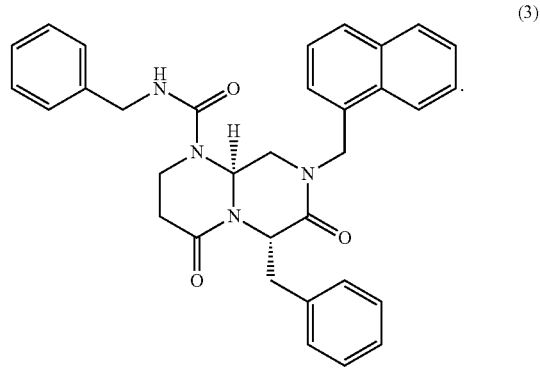 [SMILES: O=C1[C@H](Cc2ccccc2)N2C(=O)CCN(C(=O)NCc3ccccc3)[C@H]2CN1Cc1cccc2ccccc12]

(3)

2. The method of treating malignant liver tumor according to claim 1, wherein the administering inhibits a liver cancer stem cell.

3. The method of treating malignant liver tumor according to claim 2, wherein the liver cancer stem cell expresses a cancer stem cell marker.

4. The method of treating malignant liver tumor according to claim 3, wherein the cancer stem cell marker is CD44, CD99 CD133, or EpCAM.

5. The method of treating malignant liver tumor according to claim 1, wherein the patient needs treatment of a malignant liver tumor.

6. The method of treating liver malignant tumor according to claim 1, wherein the patient is determined or diagnosed as having a significantly larger number of cancer stem cells in a tissue than healthy individuals.

* * * * *